(12) United States Patent
Adie et al.

(10) Patent No.: US 12,133,711 B2
(45) Date of Patent: Nov. 5, 2024

(54) RESOLUTION-ENHANCED OPTICAL COHERENT TOMOGRAPHY

(71) Applicant: Cornell University, Ithaca, NY (US)

(72) Inventors: Steven G. Adie, Ithaca, NY (US); Nichaluk Leartprapun, Ithaca, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 0 days.

(21) Appl. No.: 18/274,963

(22) PCT Filed: Jan. 28, 2022

(86) PCT No.: PCT/US2022/070426
§ 371 (c)(1),
(2) Date: Jul. 28, 2023

(87) PCT Pub. No.: WO2022/165526
PCT Pub. Date: Aug. 4, 2022

(65) Prior Publication Data
US 2024/0041327 A1    Feb. 8, 2024

Related U.S. Application Data

(60) Provisional application No. 63/142,911, filed on Jan. 28, 2021.

(51) Int. Cl.
*A61B 5/00* (2006.01)
*G06T 5/50* (2006.01)

(52) U.S. Cl.
CPC .......... *A61B 5/0066* (2013.01); *A61B 5/7203* (2013.01); *A61B 5/7257* (2013.01); *G06T 5/50* (2013.01)

(58) Field of Classification Search
CPC .... A61B 5/0066; A61B 5/7203; A61B 5/7257
See application file for complete search history.

(56) References Cited

U.S. PATENT DOCUMENTS

| 2008/0193034 A1 | 8/2008 | Wang |
| 2013/0039559 A1 | 2/2013 | Grass et al. |
| 2016/0341539 A1 | 11/2016 | Adie et al. |

(Continued)

OTHER PUBLICATIONS

PCT/US2022/070426 International Search Report and Written Opinion dated Apr. 5, 2022, 7 pages.

*Primary Examiner* — Joel F Brutus
(74) *Attorney, Agent, or Firm* — Cozen O'Connor

(57) ABSTRACT

Methods, systems, and devices for generating resolution-enhanced space-domain image of a target sample based on optical coherent tomography (OCT) imaging technologies are disclosed. In an aspect, a system includes a processing platform comprising one or more processing devices operatively coupled to one or more memory devices. The processing platform is configured to acquire a plurality of related sets of optical coherence tomography (OCT) image data for a target object volume, reconstruct space-domain OCT images for each of the plurality of sets of OCT image data, coherently average the reconstructed space-domain OCT images to suppress noise or enhance a signal-to-noise ratio, and computationally expand a spatial bandwidth of the coherent-averaged OCT image data via deconvolution.

22 Claims, 64 Drawing Sheets

(56) References Cited

U.S. PATENT DOCUMENTS

| | | |
|---|---|---|
| 2017/0020387 A1* | 1/2017 | Fingler ................ G02B 6/0005 |
| 2017/0201328 A1* | 7/2017 | Hugi ....................... G01J 3/433 |
| 2017/0241765 A1 | 8/2017 | Adie et al. |
| 2017/0290515 A1* | 10/2017 | Butte ................... A61B 5/0071 |
| 2019/0056214 A1* | 2/2019 | Everett .................. A61B 3/152 |
| 2021/0003382 A1 | 1/2021 | Adie et al. |

* cited by examiner

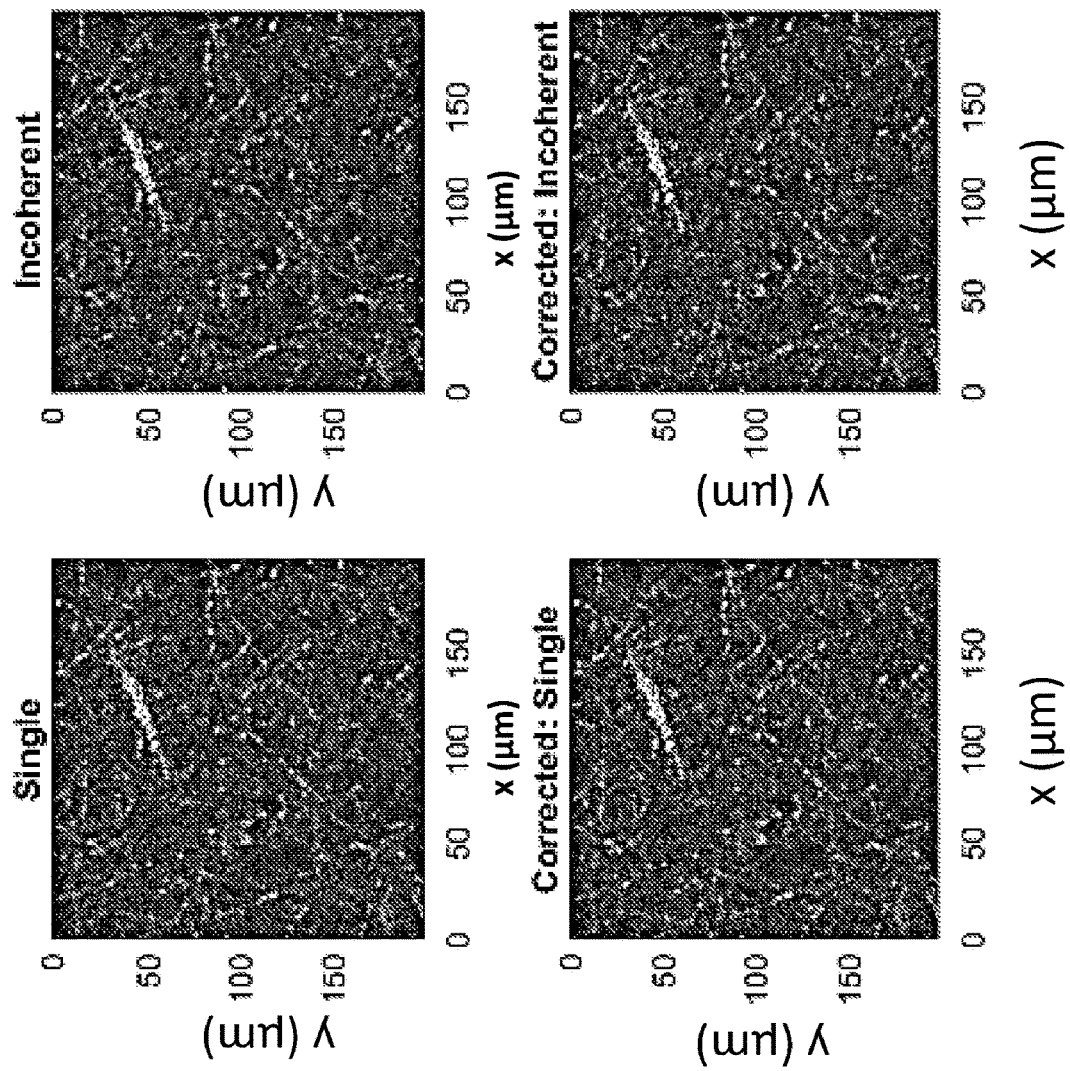

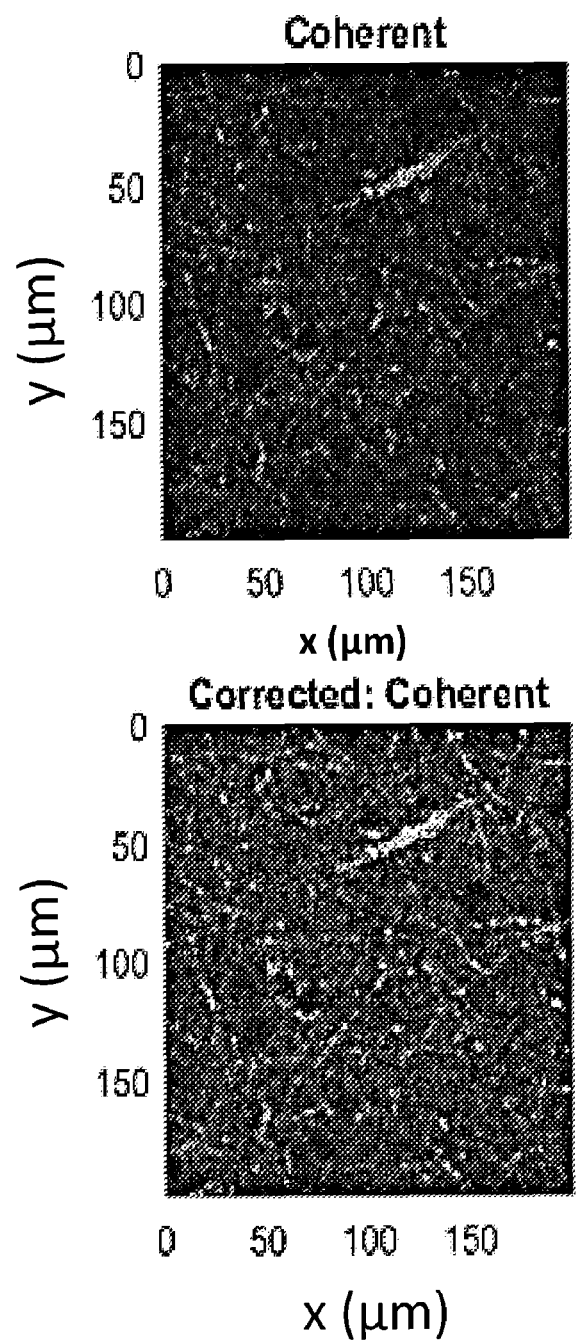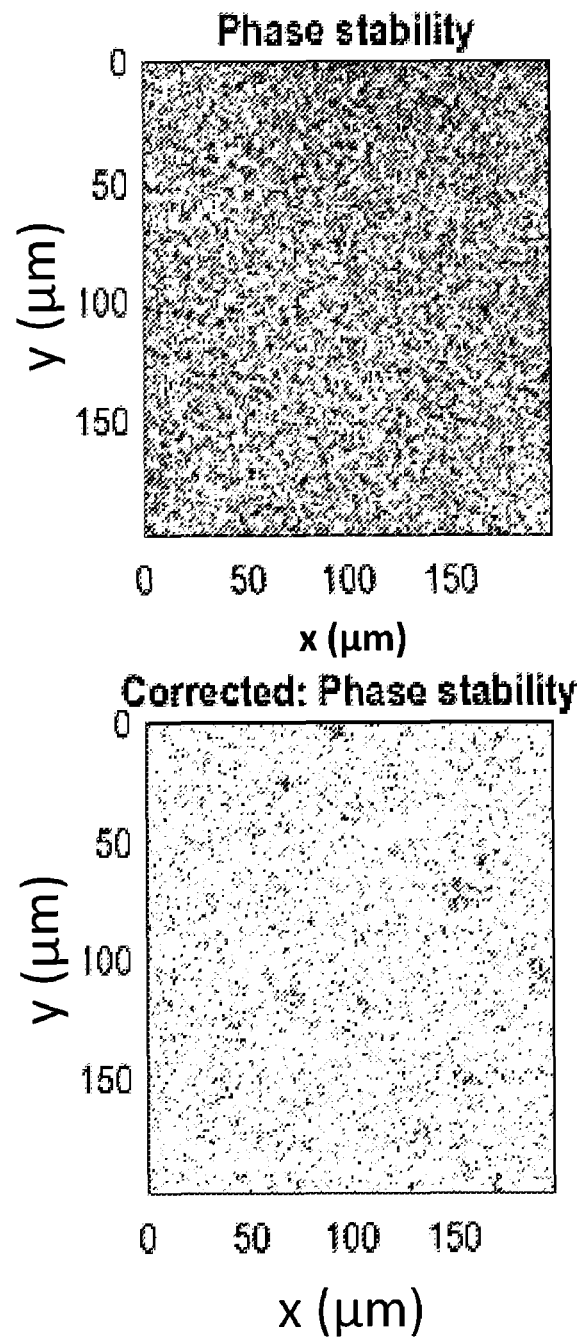
FIG. 21C
FIG. 21D

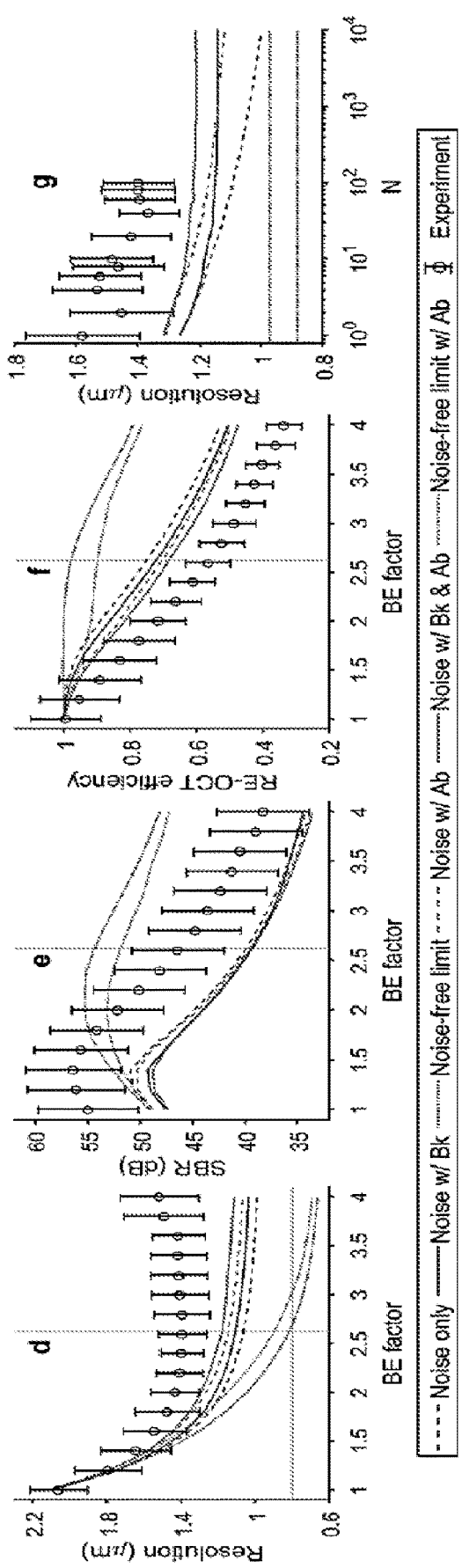

Resolution-enhanced OCT

Traditional OCT

*En face* OCT image of collagen gel
FOV 180 μm × 180 μm

RESOLUTION-ENHANCED OPTICAL COHERENT TOMOGRAPHY

PRIORITY CLAIM AND CROSS-REFERENCE TO RELATED APPLICATION

This application claims priority to and benefits of U.S. Provisional Application No. 63/142,911, filed on Jan. 28, 2021, the disclosure of which is hereby incorporated by reference herein in its entirety.

TECHNICAL FIELD

This patent document relates to optical imaging techniques.

BACKGROUND

Optical coherence tomography (OCT) is a noninvasive imaging technology used to obtain high resolution cross-sectional images of the sample. Resolution-enhanced optical coherent tomography (RE-OCT) is an approach that allows one to improve the resolution of traditional OCT images acquired by a beam-scanned OCT system, without any modification to the optical system itself.

SUMMARY

The technology disclosed in this patent document can be used to construct optical coherent tomography (OCT) systems that can enhance the OCT image resolution.

In one aspect, the disclosed technology can be implemented to provide a system that includes a processing platform comprising one or more processing devices operatively coupled to one or more memory devices, the processing platform being configured to acquire a plurality of related sets of optical coherence tomography (OCT) image data for a target object volume, reconstruct space-domain OCT images for each of the plurality of sets of OCT image data, coherently average the reconstructed space-domain OCT images to suppress noise or enhance a signal-to-noise ratio, and computationally expand a spatial bandwidth of the coherent-averaged OCT image data via deconvolution.

In another aspect, the disclosed technology can be implemented to provide computer program product comprising a non-transitory processor-readable storage medium having stored therein an instruction set for execution by at least one processing device of a processing platform to cause the at least one processing device to perform acts comprising acquiring a plurality of related sets of optical coherence tomography (OCT) image data for a target object volume, reconstructing space-domain OCT images for each of the plurality of sets of OCT image data, coherently averaging the reconstructed space-domain OCT images to suppress noise or enhance a signal-to-noise ratio, and expanding a spatial bandwidth of the coherent-averaged OCT image data via deconvolution.

In another aspect, the disclosed technology can be implemented to provide a method for optically measuring a target sample based on optical coherent tomography (OCT) imaging to include operating an OCT device to successively acquire multiple volumes of OCT images from the target sample, performing a reconstruction operation on each volume of the OCT images in a space domain to generate reconstructed volumes of the OCT images, generating phase-registered volumes of the OCT images by registering the reconstructed volumes of the OCT images such that structures of interest in the target sample are phase-registered, generating coherent-averaged volumes of the OCT images by coherently averaging the phase-registered volumes of the OCT images, and performing a computational operation to expand a spatial bandwidth of the coherent-averaged OCT volumes using a magnitude-based deconvolution procedure.

In another aspect, the disclosed technology can be implemented to provide an optical coherent tomography (OCT) imaging method including operating an OCT device to successively acquire multiple volumes of OCT images from a target sample, performing a noise suppression operation by using a coherent averaging process on the multiple volumes of OCT images to generate multiple coherent-averaged OCT volumes, and generating resolution-enhanced OCT volumes by performing a computational bandwidth expansion operation to expand a spatial bandwidth of the multiple coherent-averaged OCT volumes.

The above and other aspects and implementations of the disclosed technology are described in more detail in the drawings, the description and the claims.

BRIEF DESCRIPTION OF THE DRAWINGS

FIGS. 21A-21C show that coherent average in unstable sample requires 3D image registration and phase drift correction.

FIGS. 27A-27G show RE-OCT with 100 acquisitions and ×2.4 bandwidth expansion (BE) in silicone phantom.

DETAILED DESCRIPTION

Optical Coherent Tomography (OCT) imaging is based on optical interference of a reference optical beam and a probe or sampling optical beam that interacts with a target such as a tissue to obtain imaging information and to extract one or more properties of the target. OCT cam be implemented in the time-domain OCT or spectral or frequency domain OCT. OCT devices can be used to provide non-invasive and label-free optical imaging of tissues and other objects or structures at a high resolution and can be implemented to provide optical imaging on the cellular scale.

Figure 31:
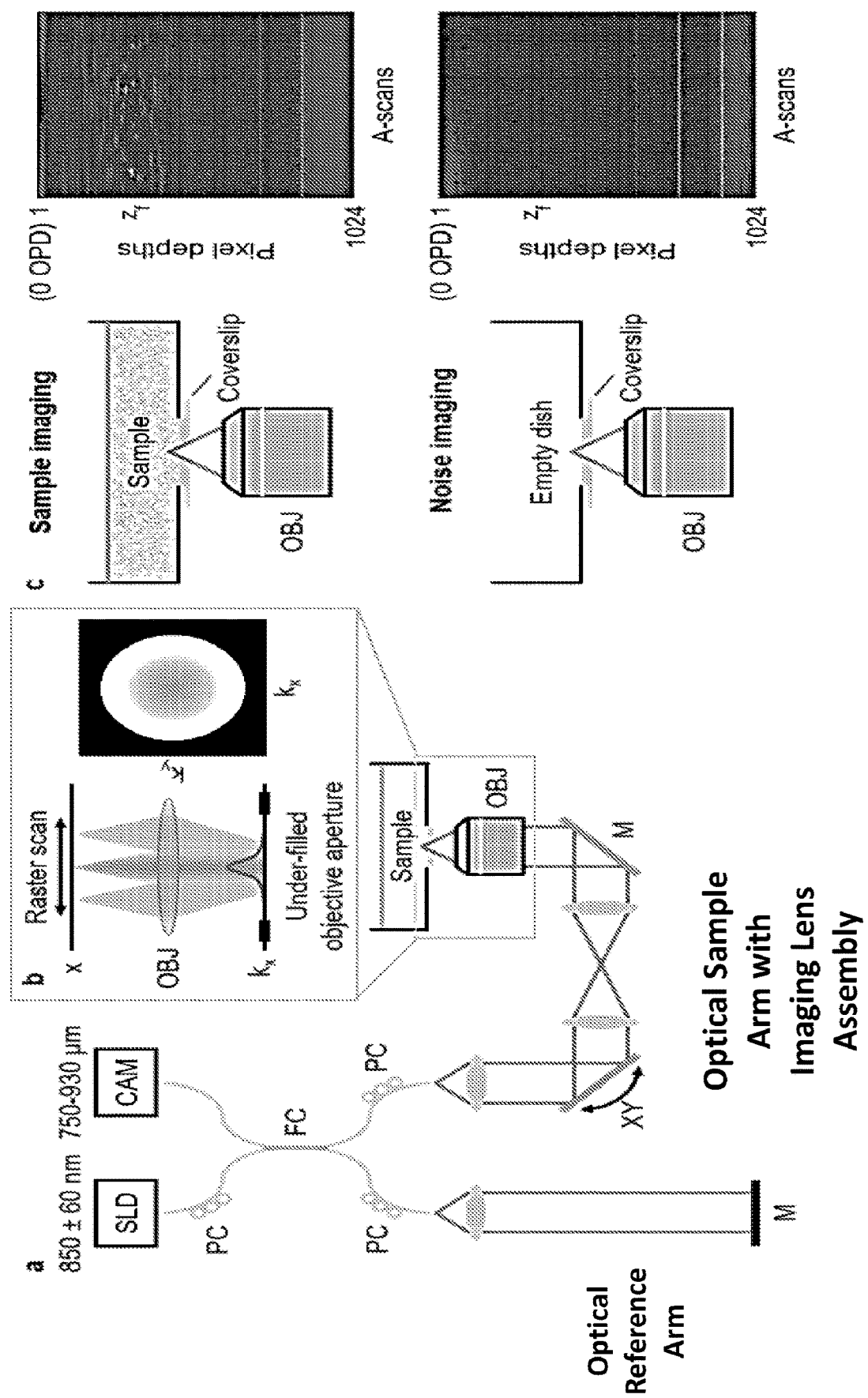
FIG. 31 shows an experimental setup.

An OCT system can be configured to include two optical arms: a reference arm that provides an optical reference signal and a sample arm with a sample to be measured. The probe light from a light source is split into a sampling beam for going into the sample arm to interact with the same and a reference beam which propagates into the reference arm as the reference signal. In some implementations, the two optical arms may spatially overlap to share a common optical path where, for example, the reference arm signal may be generated from a reflector that is placed in a common-path with the sample arm light path. The light source may be a coherent or partially coherent source. In various implementations, it is desirable that the light from the light source has a low temporal coherence where the coherence between one moment in time of a wave with another moment of time in the same wave decreases significantly over a time difference between the two moments in time and a sufficient spatial coherence which is, at a given moment in time, the coherence or partial coherence between light signals from two different locations on a wavefront. The sampling beam returned from the sample arm and the reference signal returned from the reference arm or common-path reflector in the sample arm are brought to overlap with each other to optically interfere for the OCT detection and processing. FIG. 31 shows an example.

The disclosed technology in this patent document can be used to construct optical coherent tomography (OCT) systems that can enhance the OCT image resolution by performing a coherent-average noise suppression operation and a computational bandwidth expansion operation. For example, the resolution enhancement via computational bandwidth expansion can be accomplished by expanding the spatial bandwidth of an acquired image via a magnitude-based deconvolution by reshaping magnitude spectrum via multiplication by a magnitude mask.

Resolution-enhanced optical coherent tomography (RE-OCT) disclosed in this patent document acquires multiple repeated OCT volumes of the sample successively and processes the acquired image data to improve the resolution of traditional OCT images acquired by a beam-scanned OCT system. In various implementations, the disclosed Resolution-enhanced optical coherent tomography (RE-OCT) can be used in various OCT systems with similar or different optical designs. RE-OCT can produce an OCT image with a resolution superior to that of the native focal-plane resolution of the optical system (i.e., hardware optics) if the sample can be repeatedly imaged many times. The optical system of the OCT system should be designed to underfill the objective lens aperture. Various OCT systems that implement telecentric beam-scanning to acquire volumetric images are such OCT systems and thus can be used to implement the disclosed Resolution-enhanced optical coherent tomography (RE-OCT). RE-OCT takes advantage of this common optical design of an OCT system and accomplish resolution enhancement via an efficient image computational procedure (complex averaging and magnitude-based deconvolution) that does not require any computationally intensive numerical optimization or separate calibration steps.

RE-OCT offers the flexibility to modify the resolution of the image without any potential drawbacks that may come with making hardware modifications to the optics. For instance, a traditional way to acquire images with better resolutions is to simply use a different objective lens with higher numerical aperture (NA). However, the use of the higher-NA objective lens is typically accompanied by a hardware tradeoff: a shorter working distance and a reduced field-of-view.

The resolution and image quality in OCT can be enhanced using the following approaches. In some implementations, optical coherence refraction tomography (OCRT) is an approach that enhances the resolution of OCT image along either the transverse or the axial dimension, whichever is poor. The final image will have isotropic resolution, matching that of the superior dimension. It is particularly applicable in a typical low-NA OCT system in which the transverse resolution can be several times poorer than the axial resolution. However, OCRT requires the sample to be acquired multiple times, at multiple angles spanning 360 degrees (i.e., sample must be rotated and must support imaging from multiple orientation). The image reconstruction algorithm also requires a numerical optimization procedure over multiple iteration on TensorFlow.

In some implementations, Lucy-Richardson deconvolution algorithm can be applied to OCT. Lucy-Richardson deconvolution algorithm is a commonly used procedure for image deblurring/enhancement. It is based on calculating the maximum-likelihood solution for recovering an undistorted image that has been blurred by a known point spread function (PSF) via an iterative optimization procedure. When applied to OCT, images are acquired from a separate 'calibration sample' in order to estimate the PSF of the OCT system. The estimated PSF is then used in the optimization procedure to enhance the image of the actual sample of interest.

The technology disclosed in this patent document can be implemented in some embodiments to enhance the OCT image resolution using a coherent-average noise suppression and a computational bandwidth expansion (BE).

In an implementation of the disclosed technology, RE-OCT can offer flexibility to modify the resolution of OCT images by acquiring the image as usual repeatedly, without modifying either the hardware optical system or the setup in which the sample is imaged.

In another implementation of the disclosed technology, RE-OCT can support the resolution enhancement via a simple magnitude-based deconvolution procedure, which traditionally amplifies noise in the image, while maintaining adequate contrast in the final image. Some embodiments of the disclosed technology can be used to navigate the traditional tradeoff between resolution and signal-to-noise ratio (SNR) by suppressing noise with coherent average before performing the deconvolution to enhance resolution.

In another implementation of the disclosed technology, RE-OCT can offer flexibility to select the desired optimal resolution and contrast of the final image by adjusting how many OCT volumes to average and how much to computationally expand the bandwidth. In one example, RE-OCT can choose to prioritize resolution enhancement (by expanding the bandwidth by a large factor) if high contrast is not desired, or if the sample generates strong high-contrast signal to begin with. In another example, RE-OCT can choose to 'slightly' enhance both resolution and contrast simultaneously by expanding the bandwidth with only a small factor.

In some implementations, RE-OCT procedure can include acquiring multiple OCT volumes successively, in the standard way that the sample of interest is usually imaged by the OCT system.

In some implementations, RE-OCT procedure can include reconstructing the space-domain OCT images of the individual volumes, using any reconstruction algorithm that is usually implemented for the sample of interest and OCT system. This may also include any computational image formation techniques on top of the standard OCT reconstruction procedure, e.g., coherence-gate curvature correction, computational defocus correction, computational adaptive optics, etc.

In some implementations, RE-OCT procedure can include correcting sample shift/motion and bulk phase drift of individual volumes to register all volumes and ensure that the structures of interest in the sample are phase-registered. This is only required if the sample is unstable or if there is any phase drift, e.g., due to motion for in vivo imaging, sample shrinkage/swelling in some hydrogels, or temperature drift. This issue may be mitigated by faster acquisitions, e.g., MHz-OCT using swept source.

In some implementations, RE-OCT procedure can include coherently averaging the individual phase-registered OCT volumes to suppress noise, i.e., enhance SNR. The more volumes averaged, the more noise is suppressed. Noise suppression obeys a factor of 1/N in theory, where N is the number of volumes.

In some implementations, RE-OCT procedure can obtain resolution-enhanced OCT image by computationally expanding the spatial bandwidth of the coherent-averaged OCT volume via a magnitude-based deconvolution procedure. In an embodiment of the disclosed technology, RE-OCT procedure can include at least one of the following computational operations:

(a) The computational operations of the RE-OCT procedure may include computing 2D Fourier transform of the coherent-averaged volume along the transverse dimension.

(b) The computational operations of the RE-OCT procedure may include obtaining the 'magnitude spectrum' of the image by averaging the magnitude of the 2D Fourier transform across 10-30 depths about the focal plane.

(c) The computational operations of the RE-OCT procedure may include fitting the 'magnitude spectrum' to a Gaussian curve (the spectrum has a Gaussian shape for OCT systems that image with a Gaussian beam).

(d) The computational operations of the RE-OCT procedure may include computing a 'target spectrum shape' with expanded bandwidth, essentially the Gaussian curve fit in (c) with a larger width.

(e) The computational operations of the RE-OCT procedure may include computing the 'bandwidth expansion mask' as the 'target spectrum shape' divided by the original 'magnitude spectrum.'

(f) The computational operations of the RE-OCT procedure may include multiplying the 2D Fourier transform in (a) by the 'bandwidth expansion mask.'

(g) The computational operations of the RE-OCT procedure may include computing the 2D inverse Fourier transform of the product in (f) to generate the final resolution-enhanced space-domain image.

Figure 1:
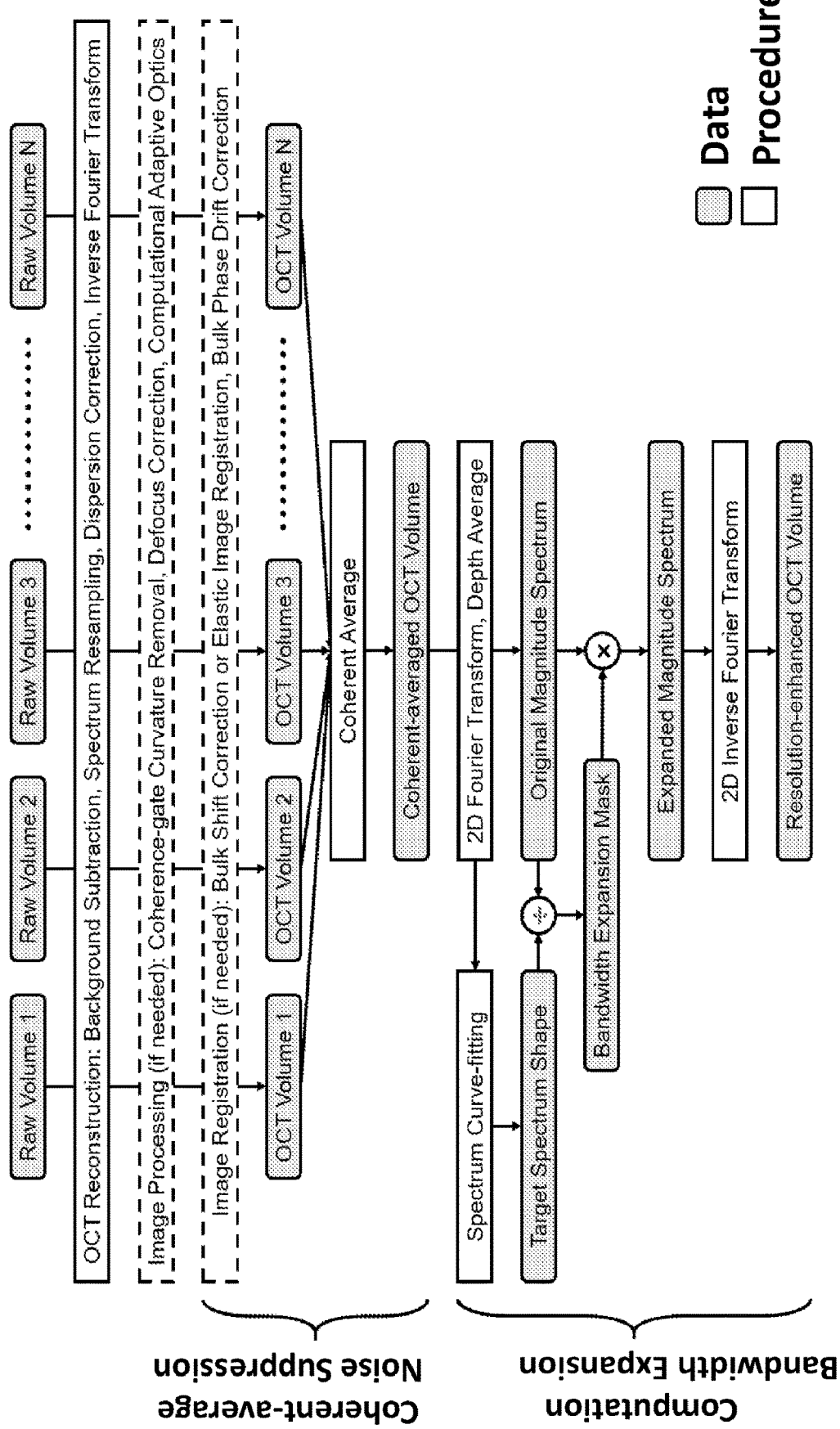
FIG. 1 shows an example of a resolution-enhanced optical coherent tomography (RE-OCT) procedure based on some embodiments of the disclosed technology.

FIG. 1 shows an example of a resolution-enhanced optical coherent tomography (RE-OCT) procedure based on some embodiments of the disclosed technology. In some implementations, the RE-OCT procedure may include a coherent-average noise suppression operation and a computational bandwidth expansion operation.

In one example, before performing the coherent-average noise suppression operation, the following operations may be performed: acquisition of raw volumes of images; and OCT reconstruction such as background subtraction, spectrum resampling, dispersion correction, and inverse Fourier Transform. In one example, additional operations may be performed before performing the coherent-average noise suppression operation: image processing; coherence-gate curvature removal; defocus correction; and computational adaptive optics.

In some implementations, the coherent-average noise suppression operation may include: image registration, bulk shift correction or elastic image registration, and bulk phase drift correction. In this way, multiple volumes of OCT images are obtained. The coherent-average noise suppression operation may include a coherent averaging operation to generate coherent-averaged OCT volumes.

In some implementations, the computational bandwidth expansion operation may include: 2D Fourier Transform and depth averaging operation to generate an original magnitude spectrum; spectrum curve-fitting to generate a target spectrum shape; mathematical operations on the original magnitude spectrum and the target spectrum shape to generate a bandwidth expansion mask; mathematical operations on the original magnitude spectrum and the bandwidth expansion mask to generate an expanded magnitude spectrum; and 2D inverse Fourier Transform to generate resolution-enhanced OCT volumes.

Figure 2:
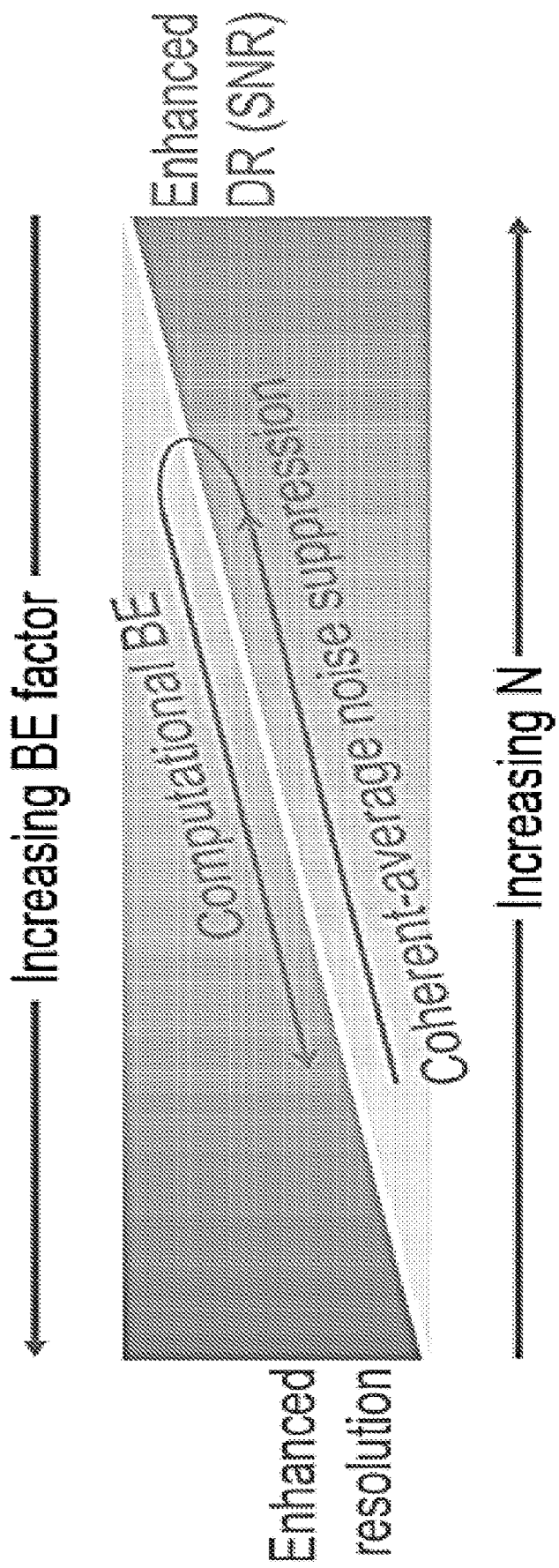
FIG. 2 shows resolution-enhanced optical coherent tomography (RE-OCT) principle and the tradeoff between the resolution and signal-to-noise ratio (SNR) based on some embodiments of the disclosed technology.

FIG. 2 illustrates the RE-OCT principle and the tradeoff between the resolution and SNR.

It is not the bandwidth, but the information capacity of an optical system that is invariant:

$$C=(2L_xB_x+1)(2L_yB_y+1)(2L_zB_z+1)\log(1+s/n) \quad \text{(Eq. 1)}$$

where L is field-of-view (FOV), B is bandwidth, s is signal power, and n is noise power. $(2L_xB_x+1)(2L_yB_y+1)(2L_zB_z+1)$ corresponds to space-bandwidth product, and $$\log\left(1+\frac{s}{n}\right)$$

corresponds to signal-to-noise ratio (SNR) (log scale).

In some implementations, RE-OCT can earn an extra dynamic range (DR) (e.g., SNR) with coherent average to obtain a larger spatial bandwidth and an enhanced resolution. Under the theorem of invariance of information capacity, it is not the spatial bandwidth, but the information capacity that remains constant. Enhanced SNR of coherent-averaged image can be sacrificed to increase the bandwidth shown as the bandwidth expansion (BE) in FIG. 2.

Figure 3:
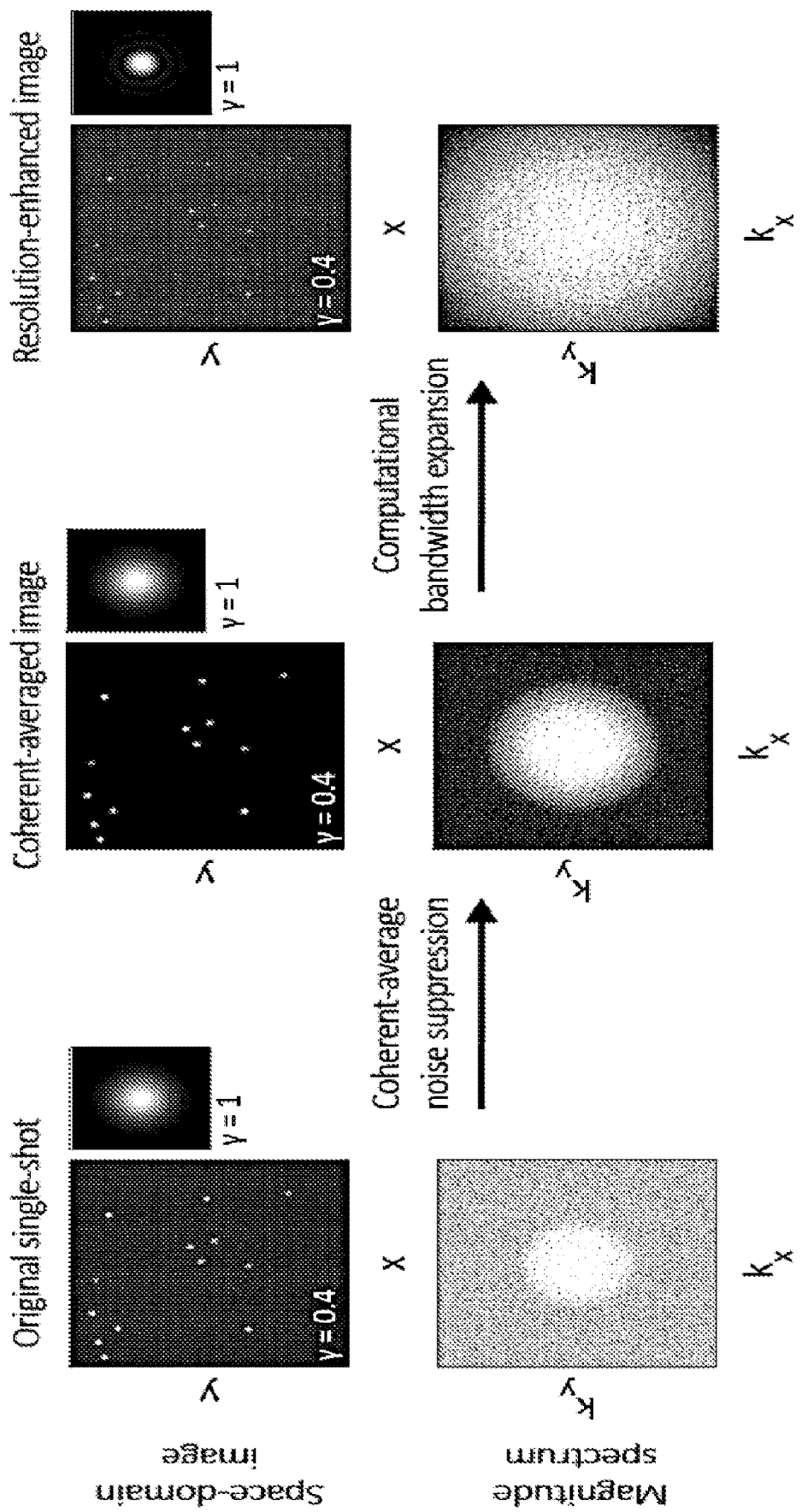
FIG. 3 shows an example of RE-OCT procedure using simulated images based on some embodiments of the disclosed technology.

FIG. 3 shows an example of an RE-OCT procedure using simulated images.

In some implementations, RE-OCT framework includes coherent-average noise suppression followed by computational bandwidth expansion (BE). In some implementations, the noise with coherent average is first suppressed because the noise increases with increasing BE.

Figure 4:
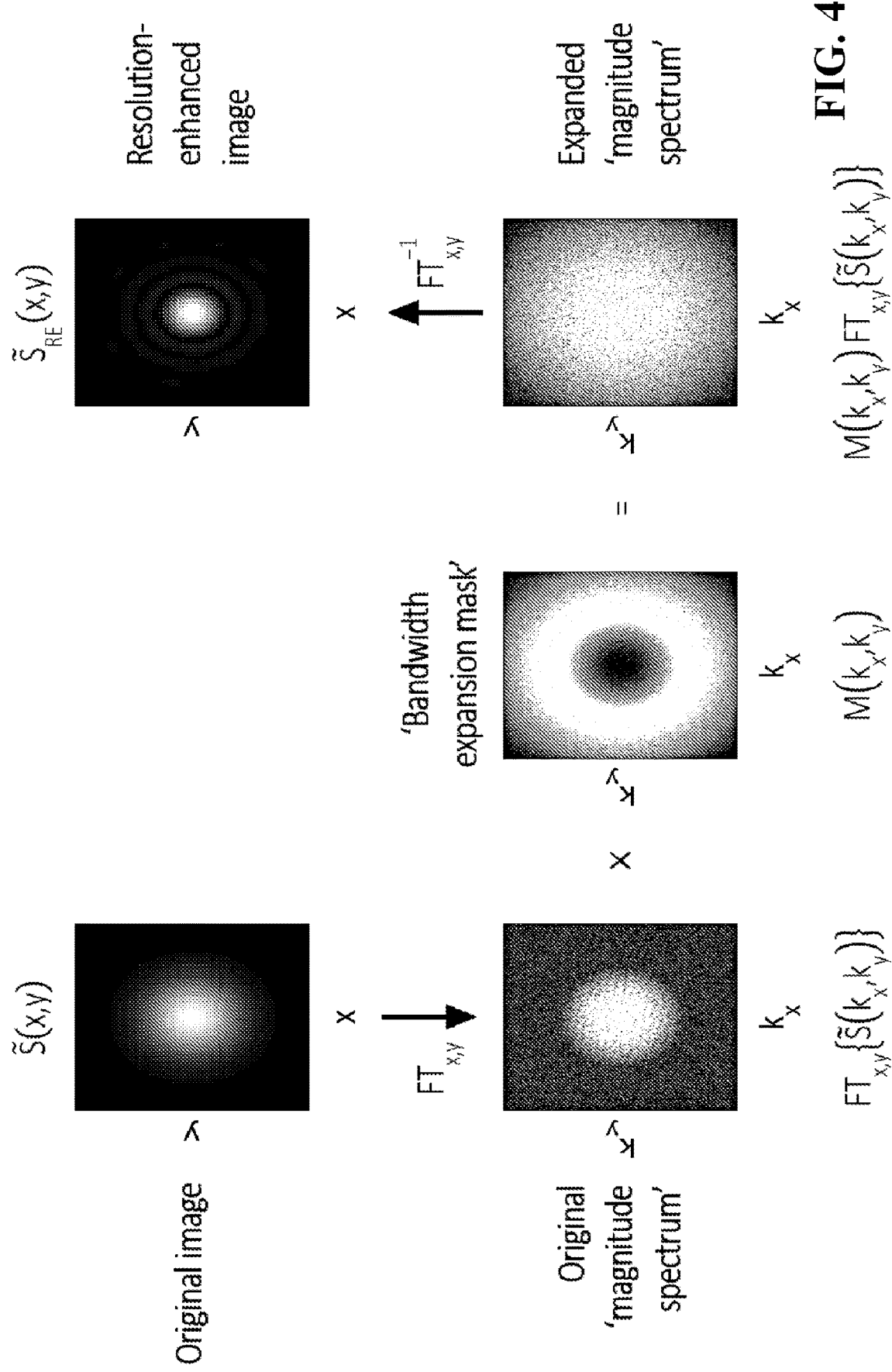
FIG. 4 shows an example of a computational bandwidth expansion process using simulated images based on some embodiments of the disclosed technology.

FIG. 4 shows an example of computational bandwidth expansion process using simulated images.

The resolution of acquired image can be enhanced by expanding its spatial bandwidth. This can be done by reshaping magnitude spectrum via multiplication by a magnitude mask, which is essentially a magnitude-based deconvolution.

In some implementations, the 'bandwidth expansion mask' may be computed in different ways, for example, by computationally expanding the spatial bandwidth of the coherent-averaged OCT volume via a magnitude-based deconvolution procedure as discussed above.

In one example, a different target spectrum shape other than a Gaussian spectrum may be selected. For instance, a flattop spectrum shape would provide maximum bandwidth expansion, but would produce ripples in the image.

In another example, if there are systematic noise patterns that can be identified in the original 'magnitude spectrum', certain spatial frequencies in the 'bandwidth expansion mask' may be 'edited' in order to avoid amplifying the systematic noise.

In some implementations, RE-OCT may be combined with aberration-diverse (AD)-OCT. Instead of acquiring multiple OCT volumes the same way successively and coherently averaging them to suppress noise, the AD-OCT procedure may be implemented instead in order to not only suppress noise, but also suppress the multiple-scattering background.

Figure 5:
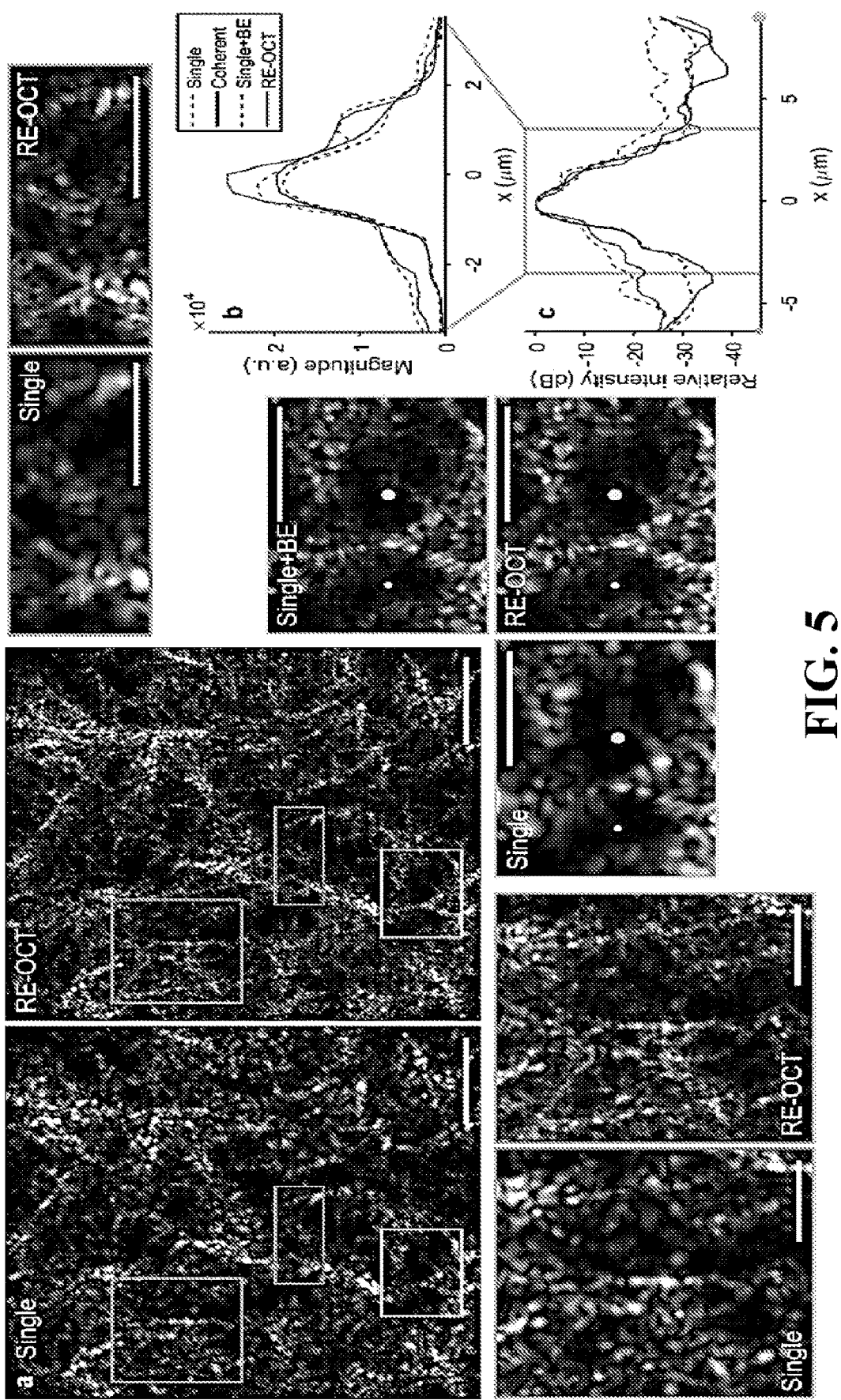
FIG. 5 shows comparisons of an original single-shot OCT image, a bandwidth-expanded single-shot image and a resolution-enhanced RE-OCT image in collagen gel.

FIG. 5 shows comparisons of the original single-shot OCT image (Single), bandwidth-expanded single-shot image (Single+BE) and the resolution-enhanced RE-OCT image (i.e., bandwidth expansion after coherent average) in collagen gel.

Figure 6:
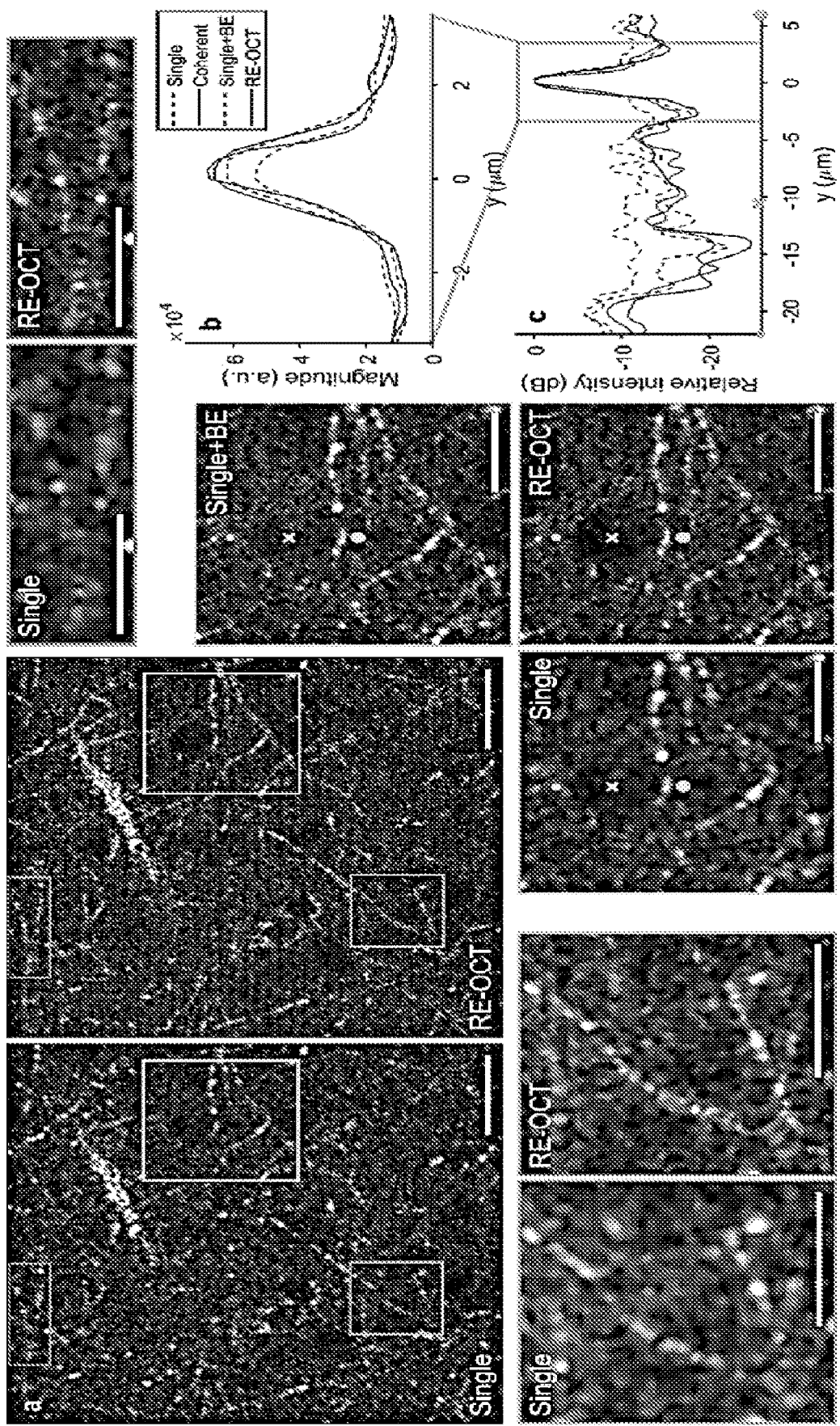
FIG. 6 shows comparisons of an original single-shot OCT image, a bandwidth-expanded single-shot image and a resolution-enhanced RE-OCT image in a first cortical layer of an ex vivo fresh mouse brain.

FIG. 6 shows comparisons of the original single-shot OCT image (Single), bandwidth-expanded single-shot image (Single+BE) and the resolution-enhanced RE-OCT image (i.e., bandwidth expansion after coherent average) in the first cortical layer of an ex vivo fresh mouse brain.

Figure 7B:
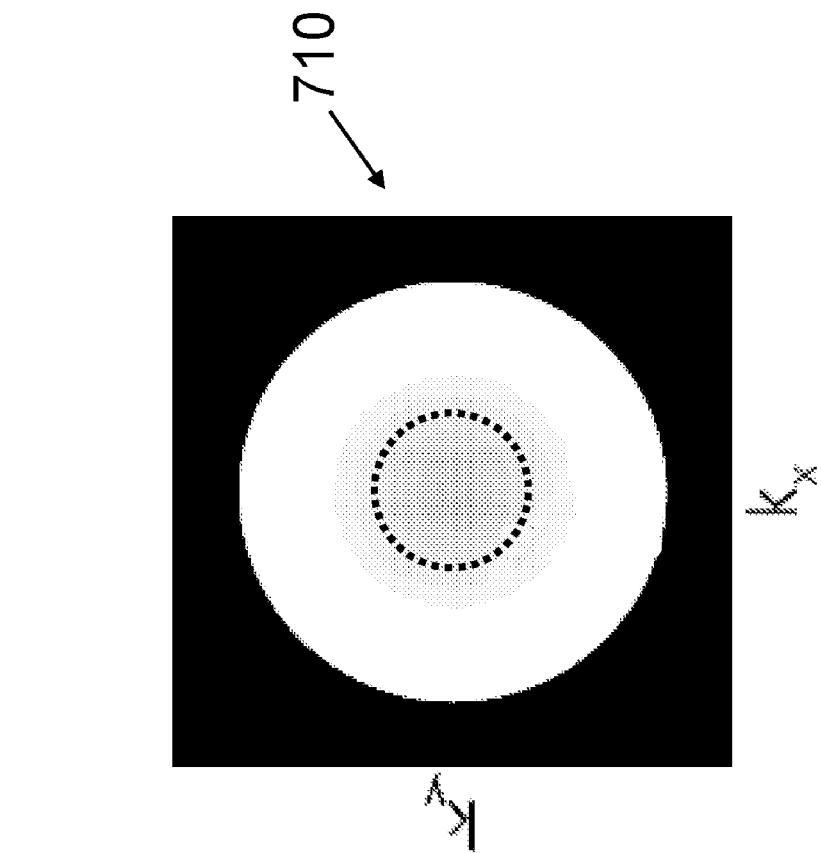
FIG. 7B shows opportunity to boost up the Gaussian tail within the objective aperture limit.

The RE-OCT implemented based on the disclosed technology is applicable in various OCT systems that underfill the objective lens aperture, such that the image is acquired at an effectively lower numerical aperture (NA) than the NA limit of the objective lens, as shown in FIG. 7B. In some implementations, RE-OCT is applicable in the OCT systems that implement the ubiquitous telecentric beam-scanning scheme shown in FIG. 7A. RE-OCT is also applicable in any samples that can be successively imaged many times and produce images of the structures of interest that are phase-registered to each other.

In some implementations, stable samples such as solid silicone phantoms can be imaged and the images can be reconstructed as is. In some implementations, mildly unstable biological samples such as hydrogels or biological tissues that may suffer from shrinking/swelling, fluid exudation, or temperature fluctuation can be imaged and reconstructed with additional image registration and phase drift correction steps. In some implementations, very unstable samples such as live-cell systems or in vivo imaging in live animals can, in principle, be imaged with high-speed OCT systems such as swept-source OCT.

Computational Approaches to Enhance Resolution in Optical Coherence Tomography

Figure 7A:
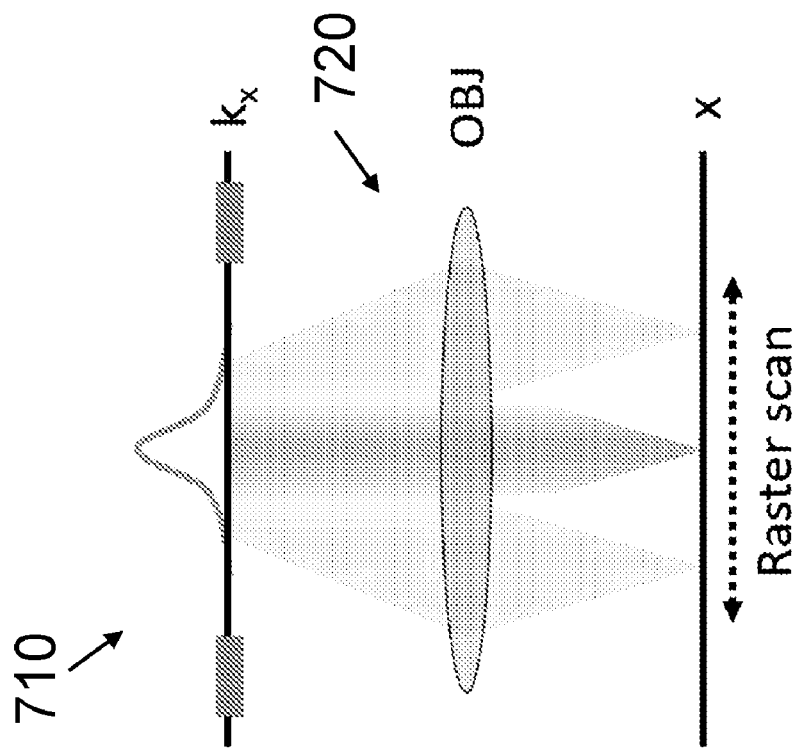
FIG. 7A shows an example of beam-scanned OCT system.

FIG. 7A shows an example of beam-scanned OCT system, and FIG. 7B shows opportunity to boost up the Gaussian tail within the objective aperture limit.

Referring to FIG. 7A, a beam-scanned OCT system includes an underfill objective aperture for beam scanning 710 and an objective lens structured to focus light lays. In some implementations, a numerical aperture (NA) is determined by $1/e^2$ width of a Gaussian beam.

For typical systems that image with Gaussian beam, the NA is determined by beam width, not objective NA. The beam-scanned OCT system based on some implementations of the disclosed technology can accommodate for expansion of imaging bandwidth by boosting up signal in the tail of Gaussian beam supported by physical objective aperture limit.

The disclosed technology can be implemented in some embodiments to enhance the resolution via computation bandwidth expansion. As discussed above, FIG. 5 shows a simulated 2D Gaussian point spread function (PSF) with complex random noise. The resolution of acquired image can be enhanced by expanding its spatial bandwidth. In one example, the resolution enhancement can be accomplished by reshaping magnitude spectrum via multiplication by a magnitude mask. This is essentially a magnitude-based deconvolution.

FIGS. 8A-8D show how to mitigate noise penalty of computation bandwidth expansion.

Computational bandwidth expansion (BE) amplifies noise as a byproduct of deconvolution. However, the disclosed technology can be implemented in some embodiments to suppress noise before computational BE by averaging complex-valued images (coherent average).

The computational BE based on some implementations of the disclosed technology can take advantage of coherent over incoherent imaging due to access to random phase noise. The noise resulting from deconvolution can be suppressed before computational BE.

Figure 8B:
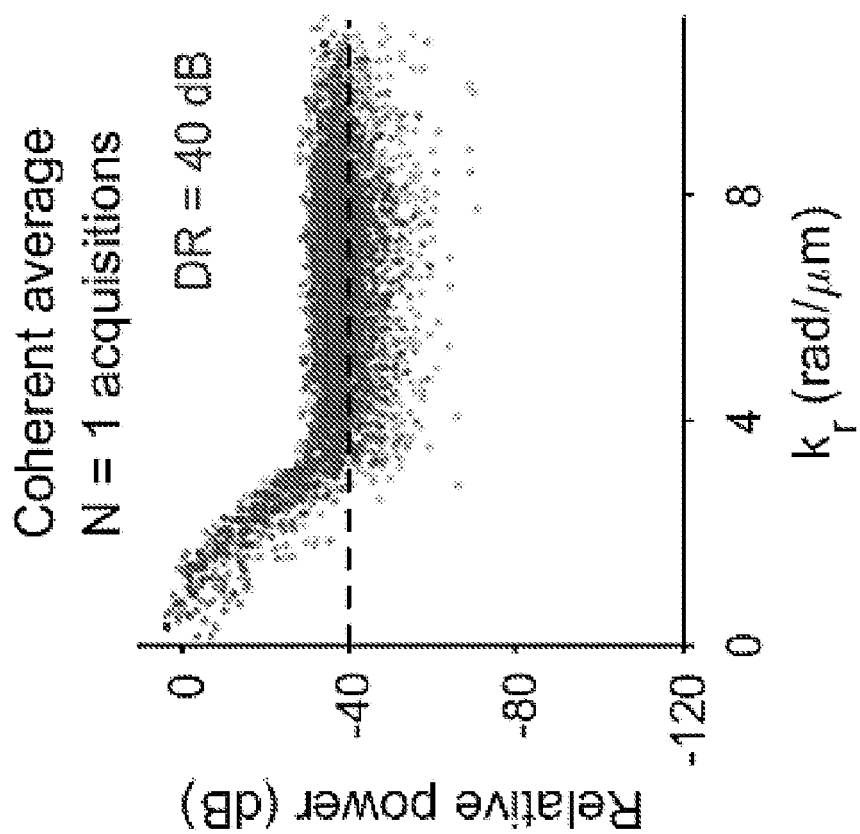
FIGS. 8A-8D show how to mitigate noise penalty of computation bandwidth expansion.
Figure 8A:
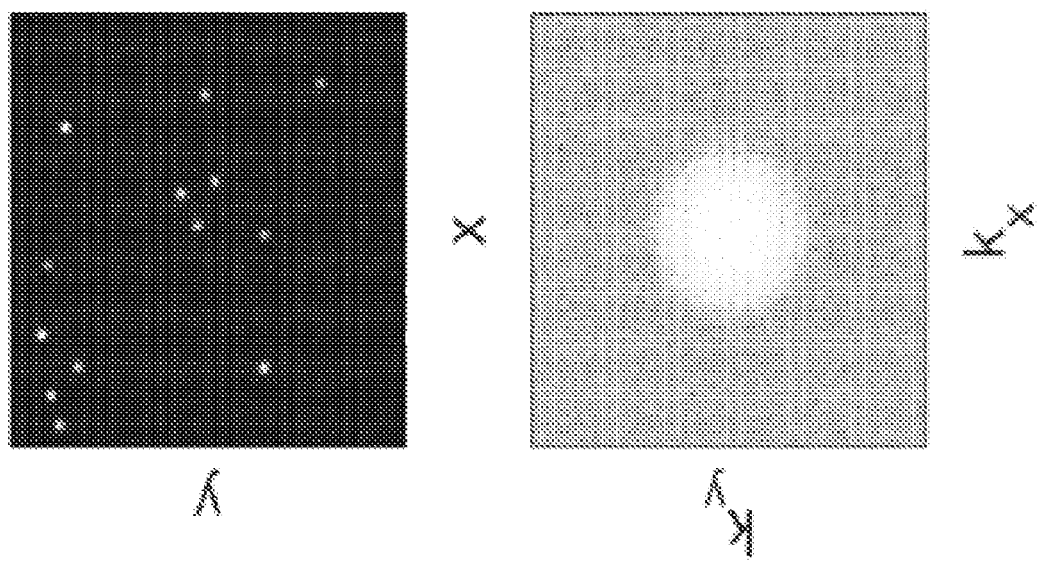
Figure 8D:
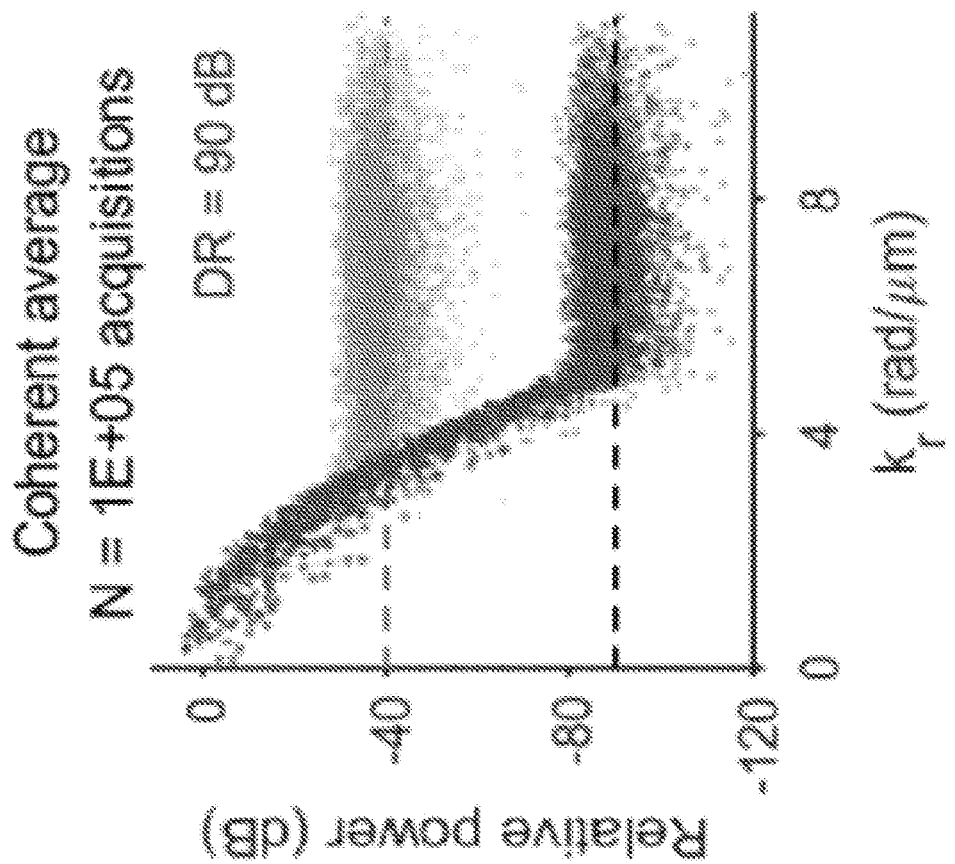
Figure 8C:
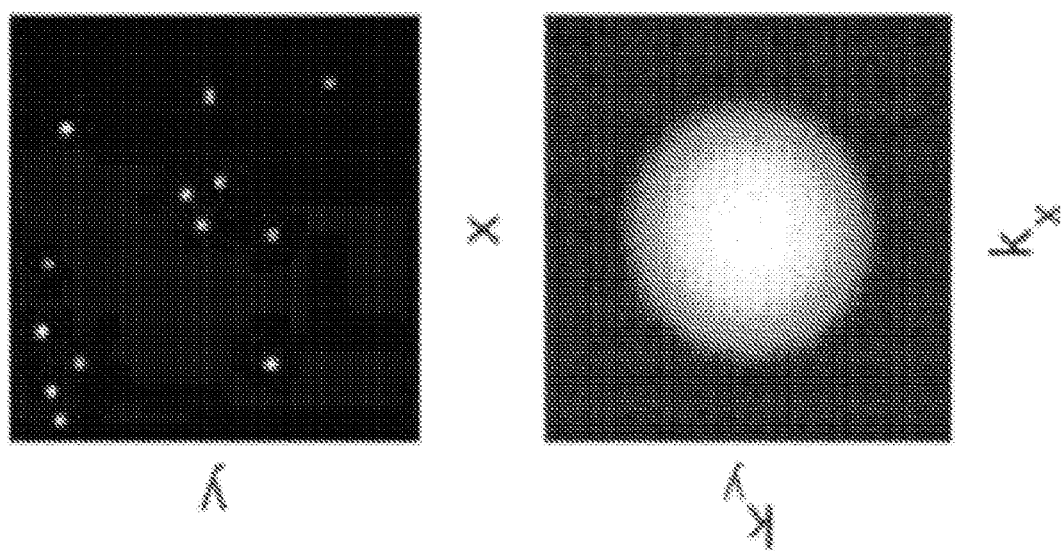

FIGS. 8B and 8D show the coherent-average noise suppression from simulation, modeling noise as circular Gaussian complex random variable. A drop in noise floor leads to a larger dynamic range (DR) in the spatial-frequency domain. Signals at these higher spatial frequencies are above suppressed noise floor.

Figure 9A:
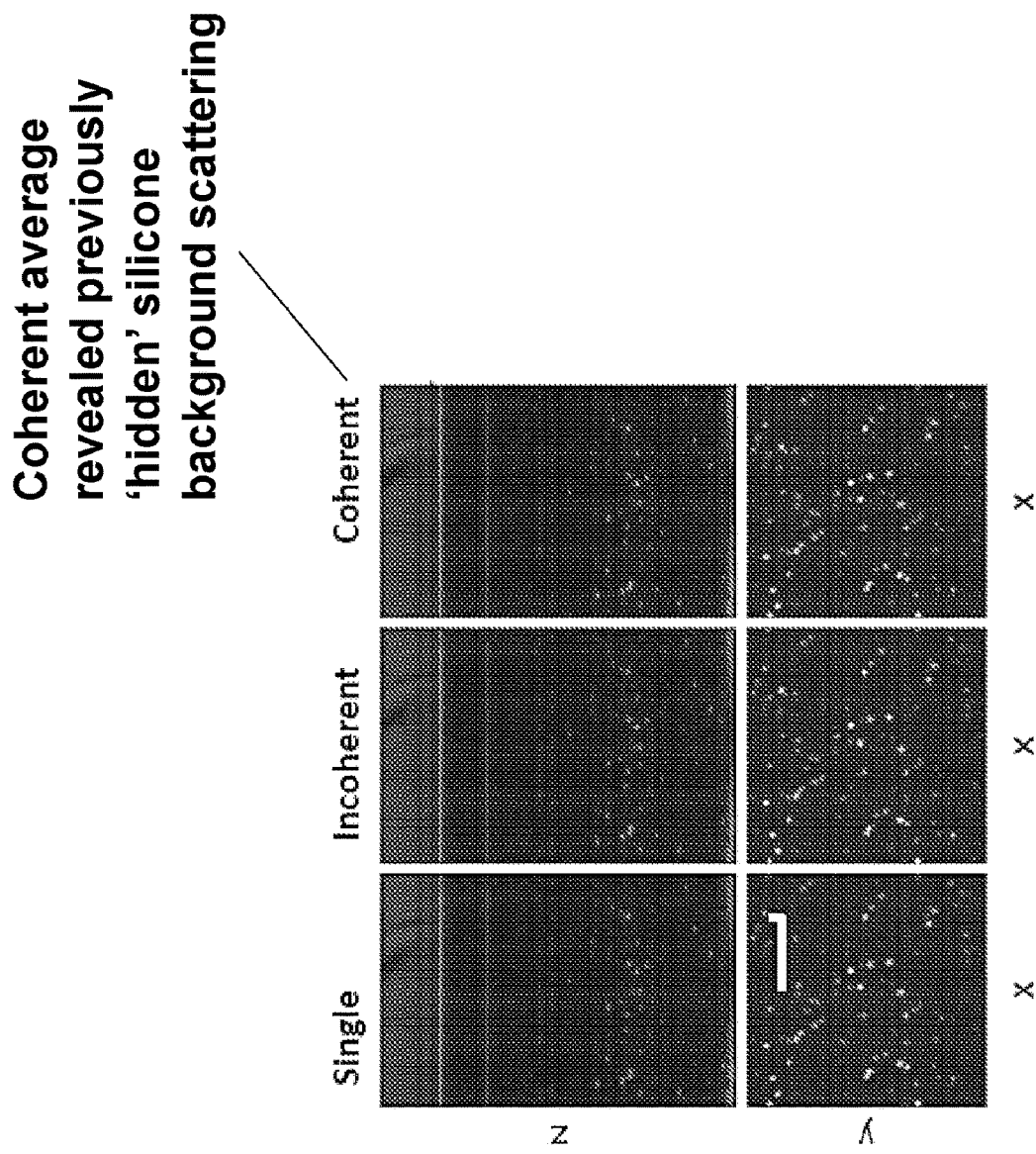
FIG. 9A shows coherent-average noise suppression in silicone phantom.
Figure 9B:
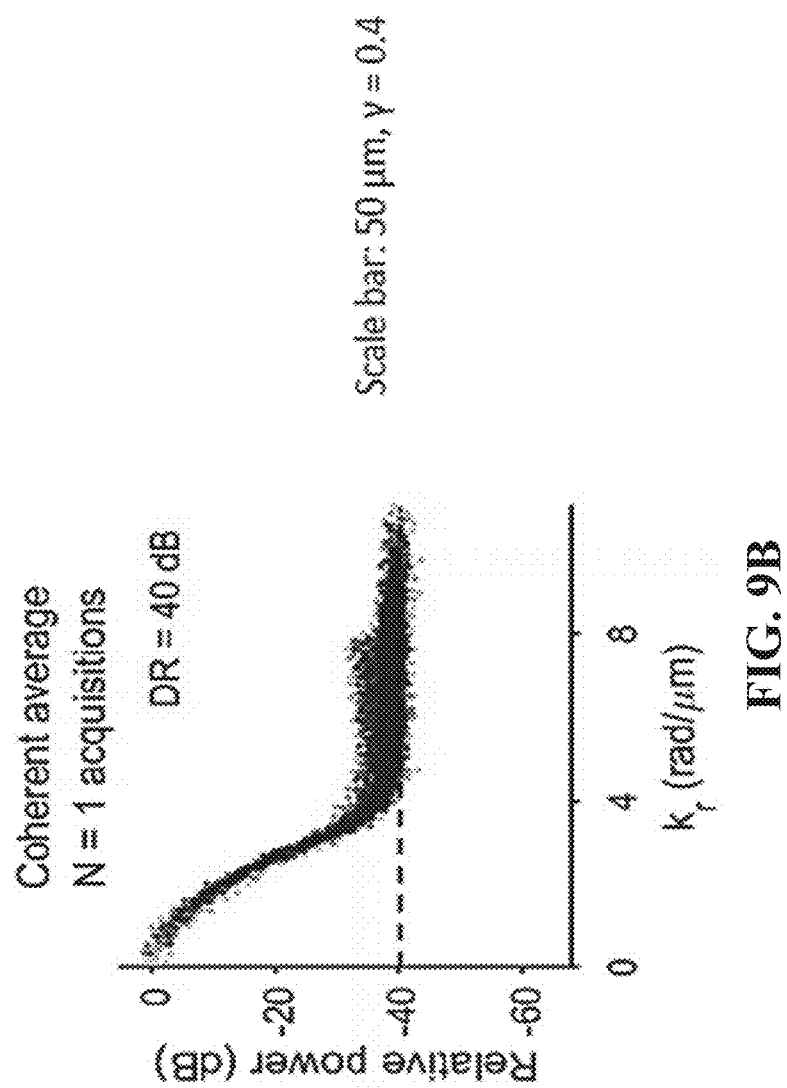
FIGS. 9B-9D show coherent average enhances dynamic range in spatial frequency.
Figure 9C:
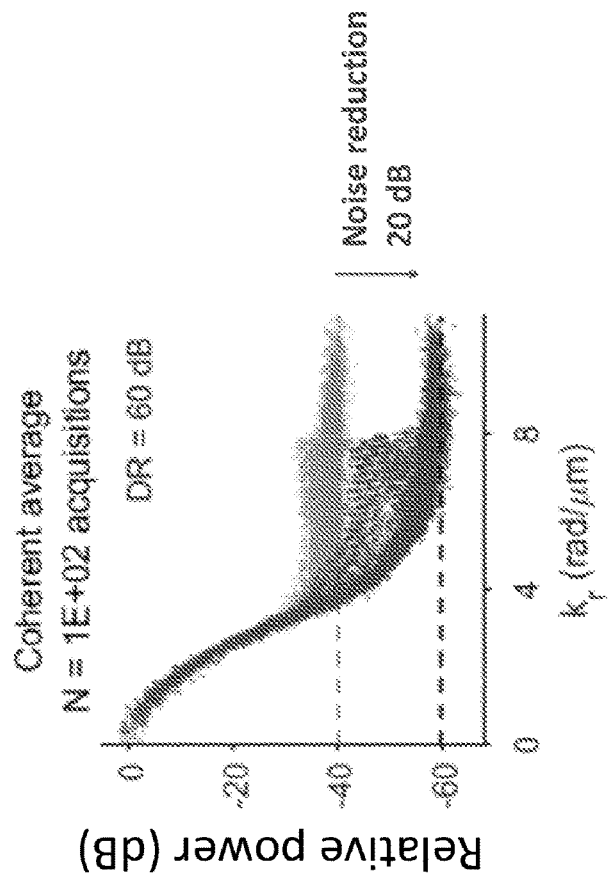
Figure 9D:
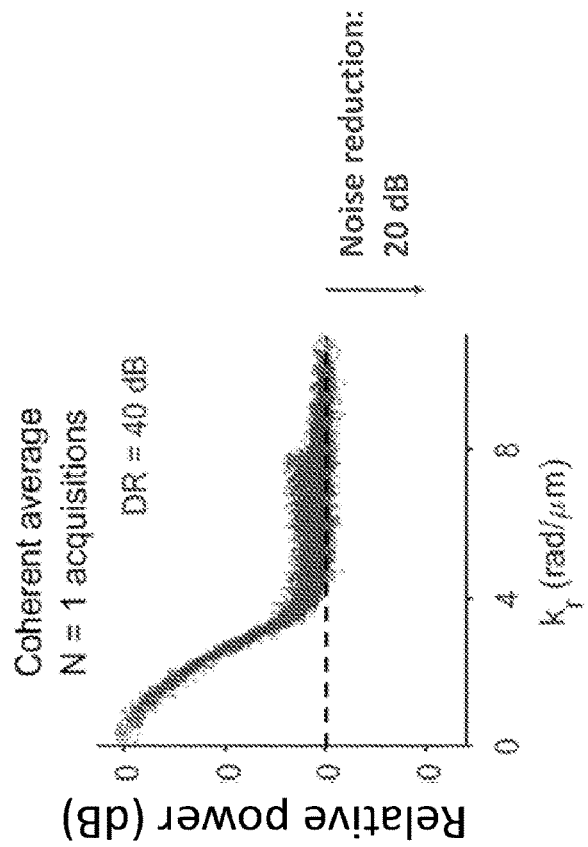

FIG. 9A shows coherent-average noise suppression in silicone phantom. FIGS. 9B-9D show coherent average enhances dynamic range in spatial frequency. FIGS. 9A-9D show a drop in signal in silicone and inside coverslip for coherent average, and speckle reduction with incoherent average, but overall signal level does not drop. Coherent average reveals scattering signal of the 'clear' silicone medium at focal plane. In the spatial frequency, the drop in noise floor results in enhancement of dynamic range (DR) like in simulated data. 20 dB noise drop corresponds to 20 dB dynamic range (DR) gain for average over N, which corresponds to 100 acquisitions.

Figure 10B:
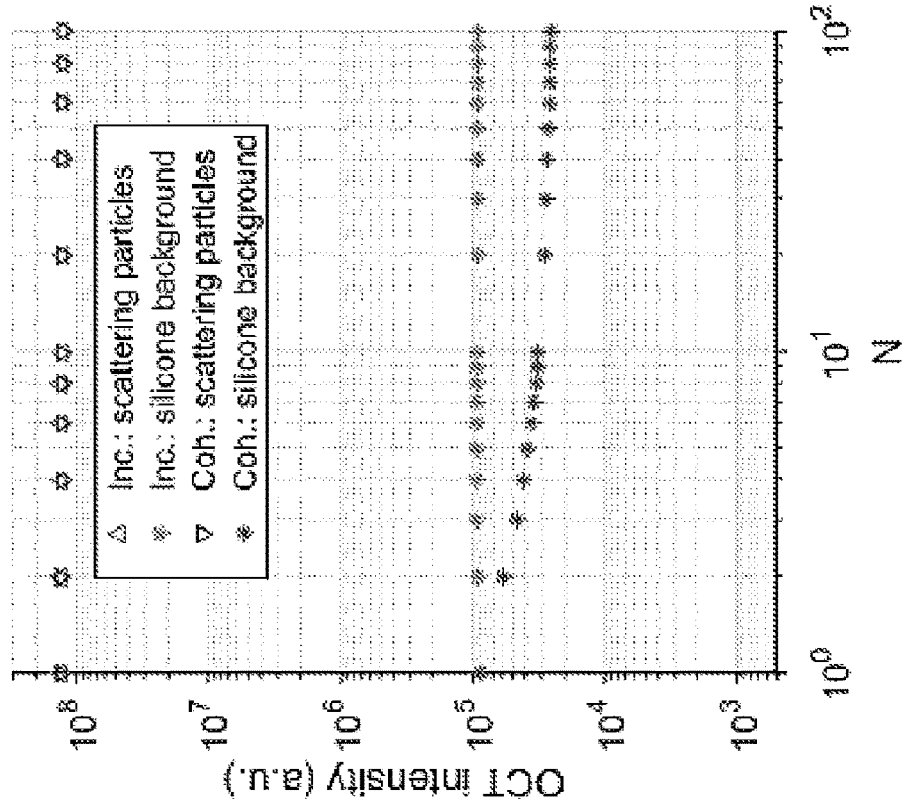
FIG. 10B shows that signal from silicone background reaches plateau.
Figure 10A:
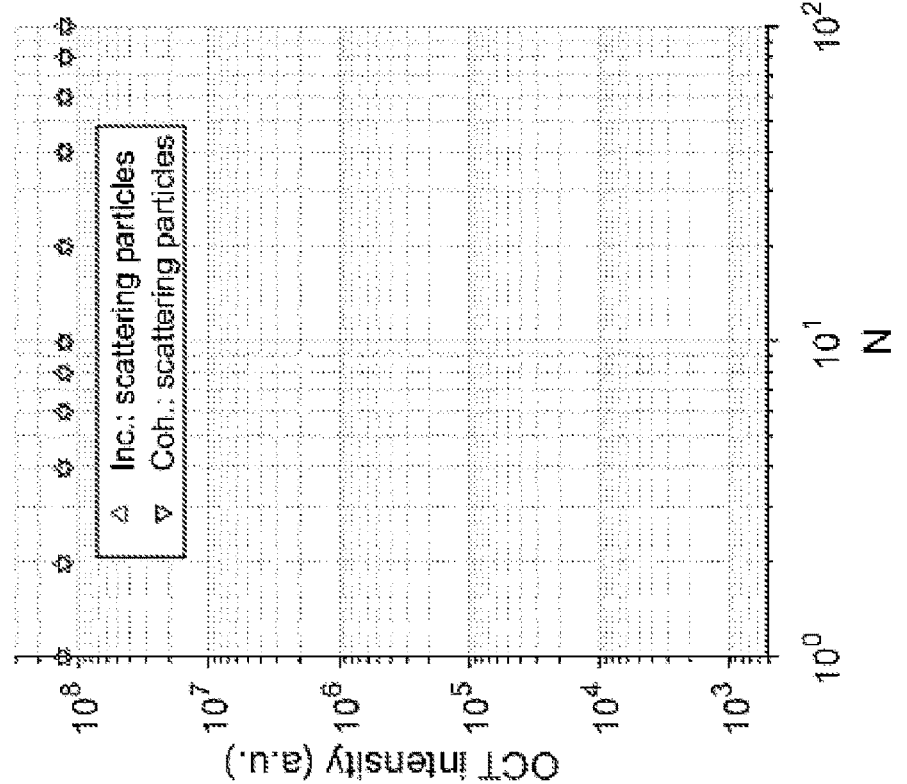
FIG. 10A shows that signal from scattering particles remains unchanged.

FIG. 10A shows that signal from scattering particles remains unchanged. The coherent average does not degrade signal from object of interest, in this case TiO2 scattering particles.

FIG. 10B shows that signal from silicone background reaches plateau. Signal from silicone medium is unchanged with incoherent average but drops with coherent average. The signal from silicone background reaches plateau after N>20. This implies that silicone generated systematic (stable in time) scattering signal, but this is low-magnitude and initially hidden by noise, and coherent average dropped noise below silicone scattering.

Figure 10D:
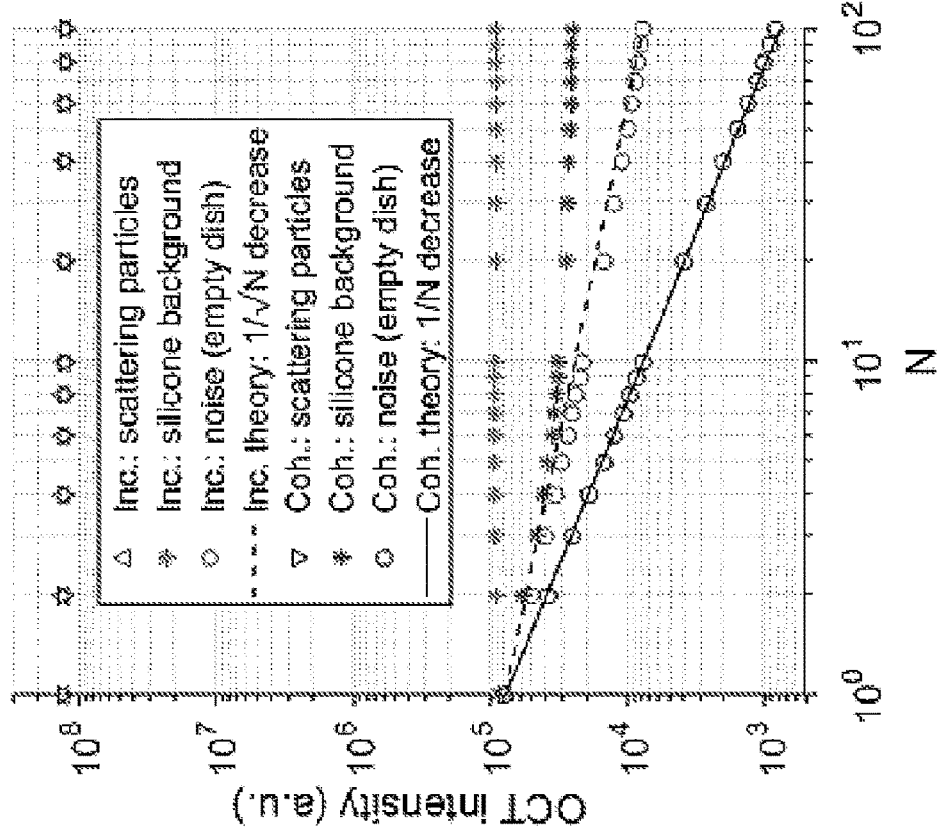
FIG. 10D shows that noise suppression by coherent average is more efficient.
Figure 10C:
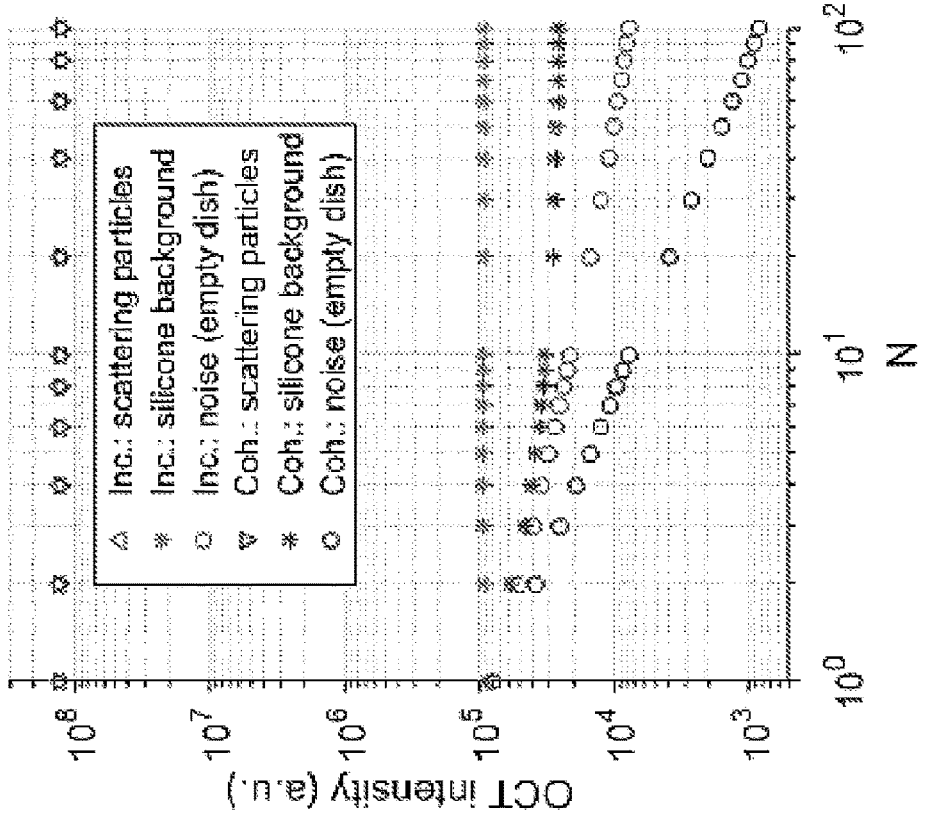
FIG. 10C shows that noise suppression by coherent average is more efficient.

FIG. 10C shows that noise suppression by coherent average is more efficient. To measure noise, image empty sample dish data is obtained from the same pixel depth as phantom image focal plane. The noise corresponds to signal intensity (e.g., OCT magnitude^2). Both incoherent and coherent averages suppress noise, but coherent is more efficient.

FIG. 10D shows that noise suppression by coherent average is more efficient. The coherent average follows 1/N, incoherent average follows 1/sqrt(N). This shows that the coherent average is more efficient by a factor of sqrt(N).

Figure 11A:
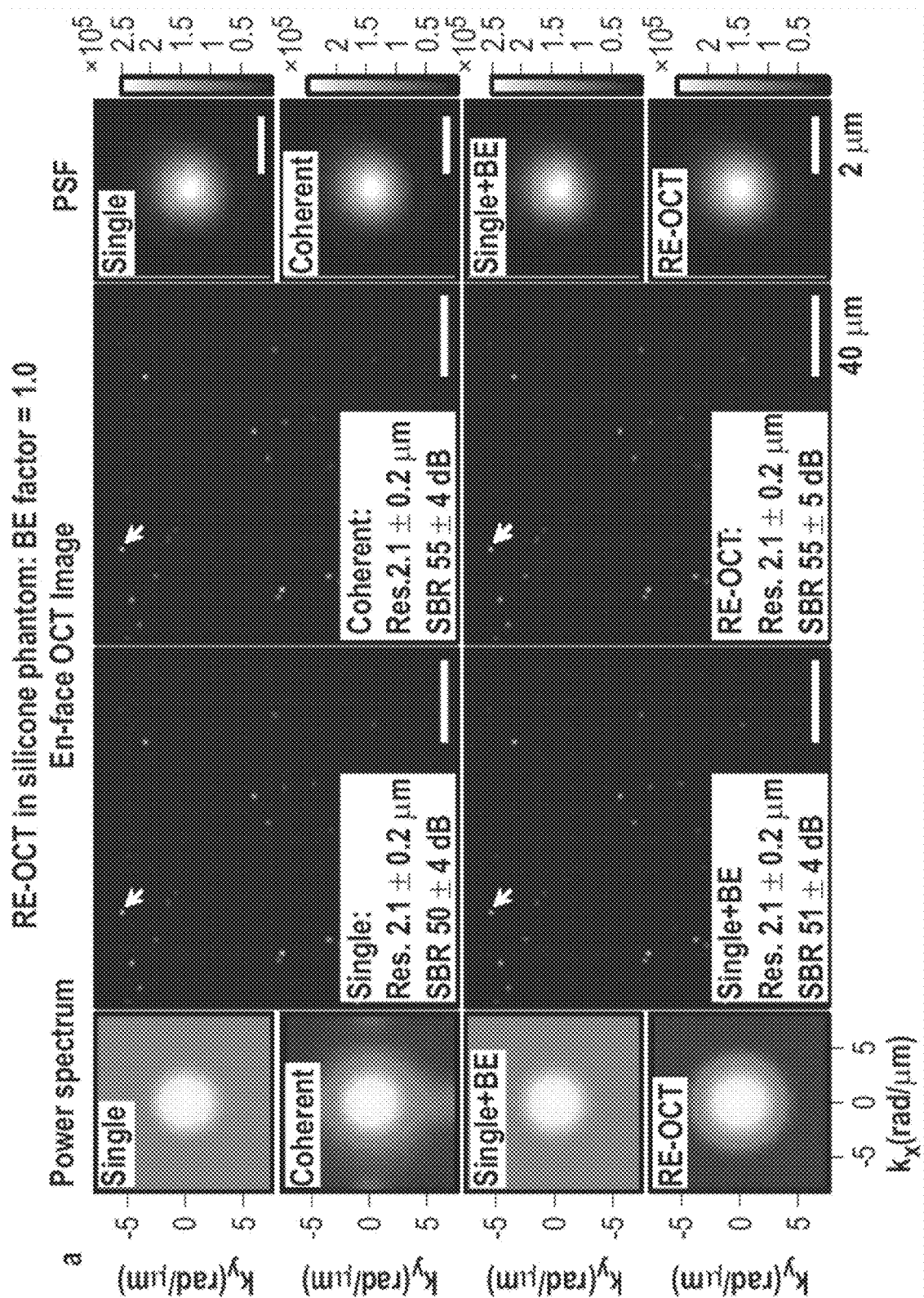
FIG. 11A shows RE-OCT in silicon phantom where BE factor is 1.0.
Figure 11B:
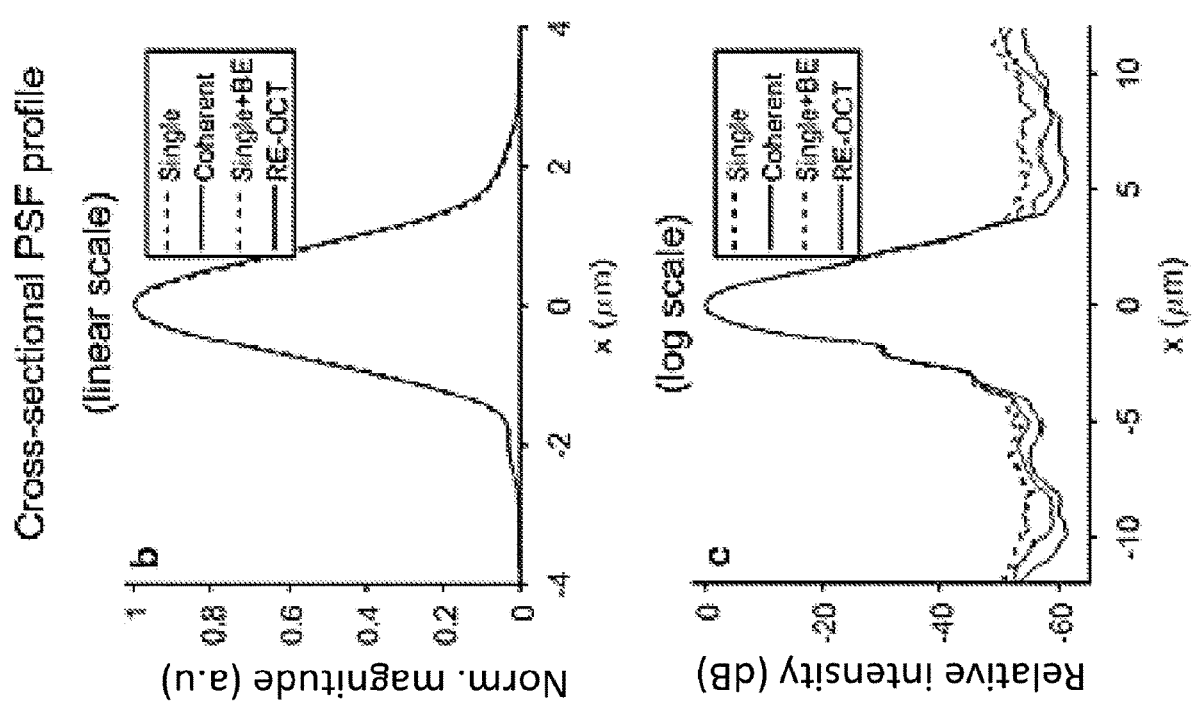
FIG. 11B shows cross-sectional point spread function (PSF) profiles.

FIG. 11A shows RE-OCT in silicon phantom where BE factor is 1.0. FIG. 11B shows cross-sectional PSF profiles. Computational BE with BE factor up to 4 shows both RE-OCT (N=100 average) and directly BE single-shot image. As BE factor increases, PSF becomes narrow and after a certain point, PSF quality degrades, and the quality degradation becomes more severe for single+bandwidth expansion (BE) case. From linear scale profile and Res. value on image, resolution improves up to BE factor=2.4, then stops improving further. From log scale cross-section (background level) and SBR value on image, SBR continues to degrade with increasing BE.

Figure 12A:
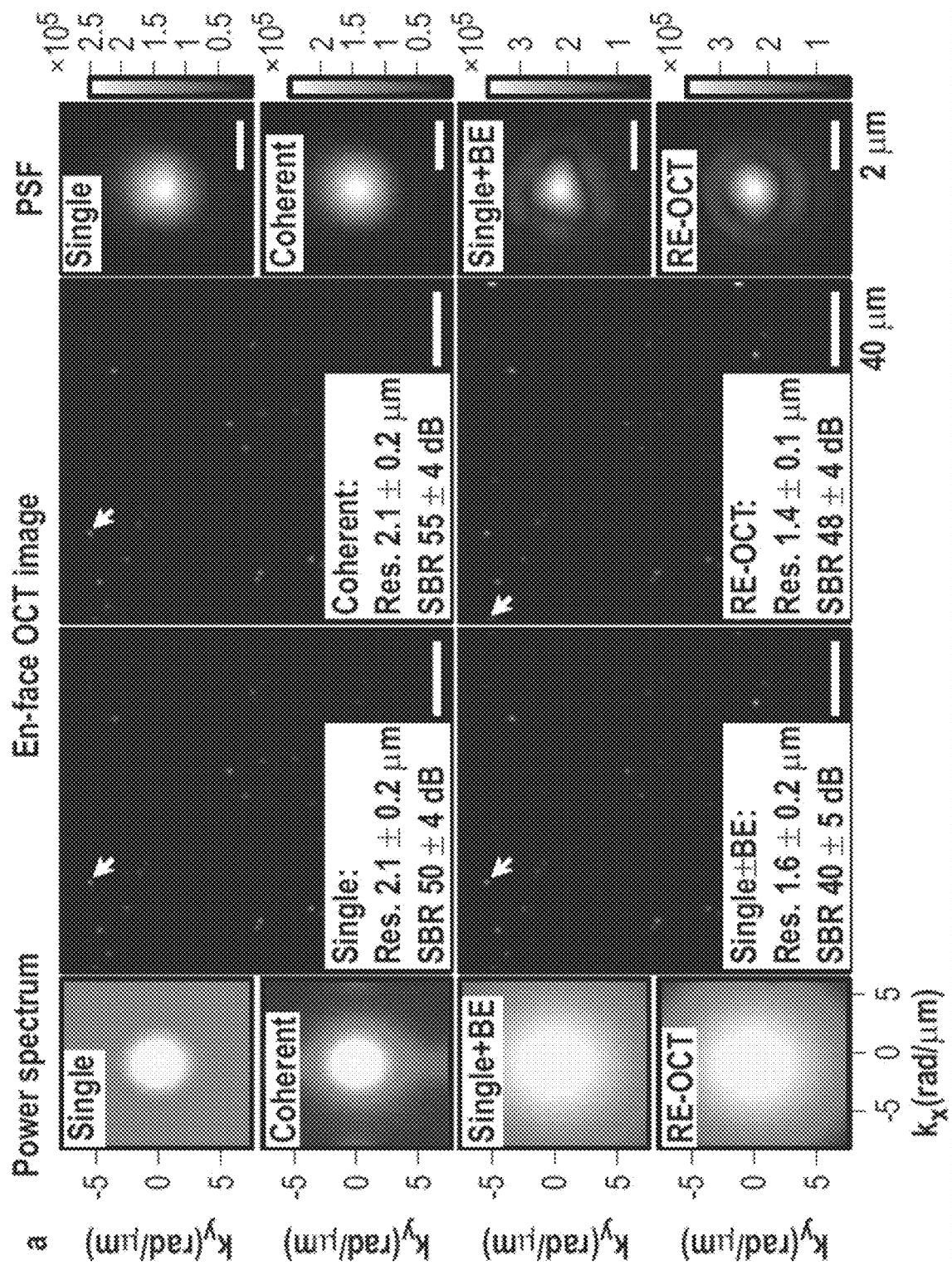
FIG. 12A shows RE-OCT in silicon phantom.
Figure 12B:
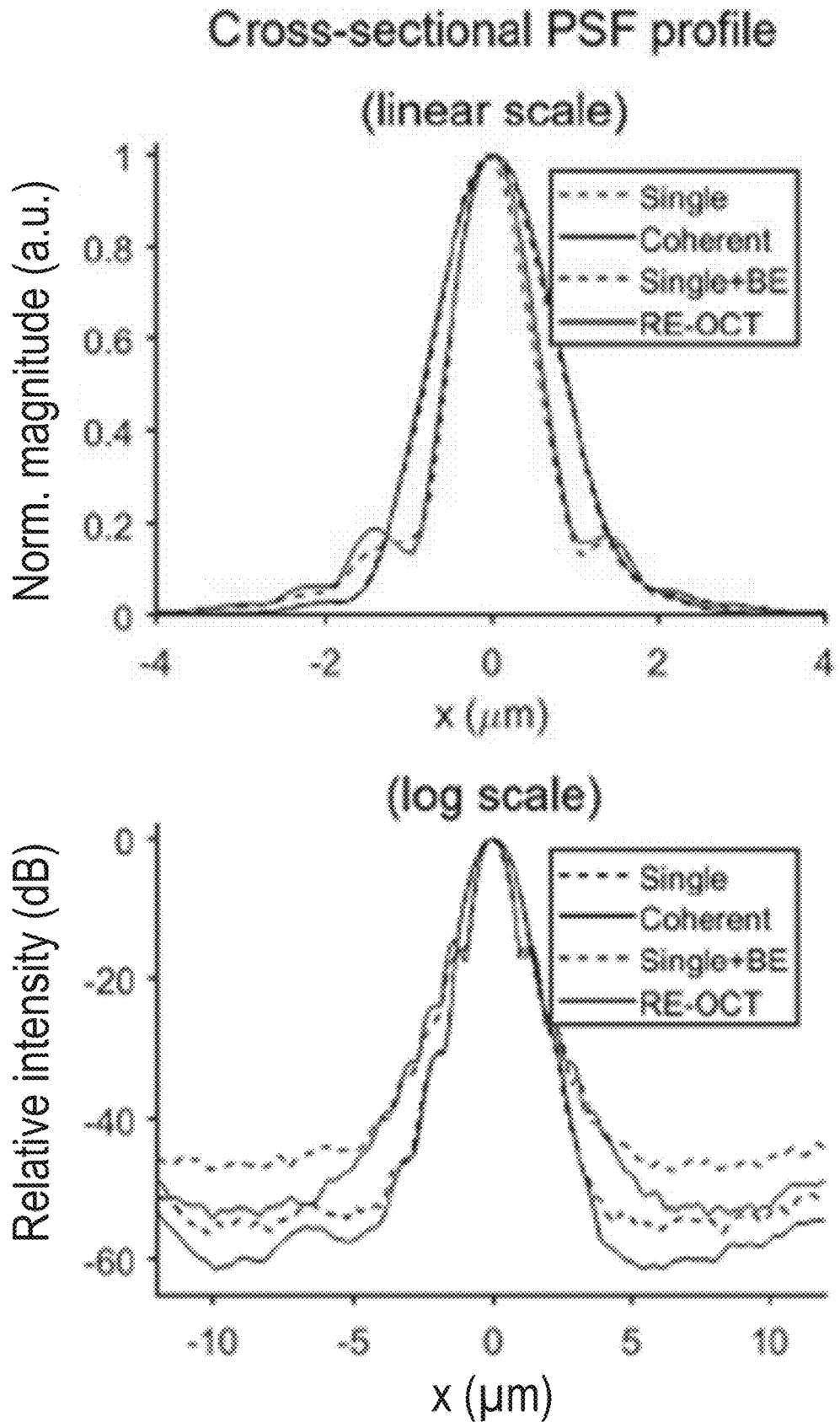
FIG. 12B shows cross-sectional PSF profiles.

FIG. 12A shows RE-OCT in silicon phantom where BE factor is 2.4 with 1.5× improvement. FIG. 12B shows cross-sectional PSF profiles. Best resolution enhancement performance can be obtained at BE factor=2.4, and 1.5× resolution improvement can be achieved (1.4 um from 2.1 um).

Figure 13:
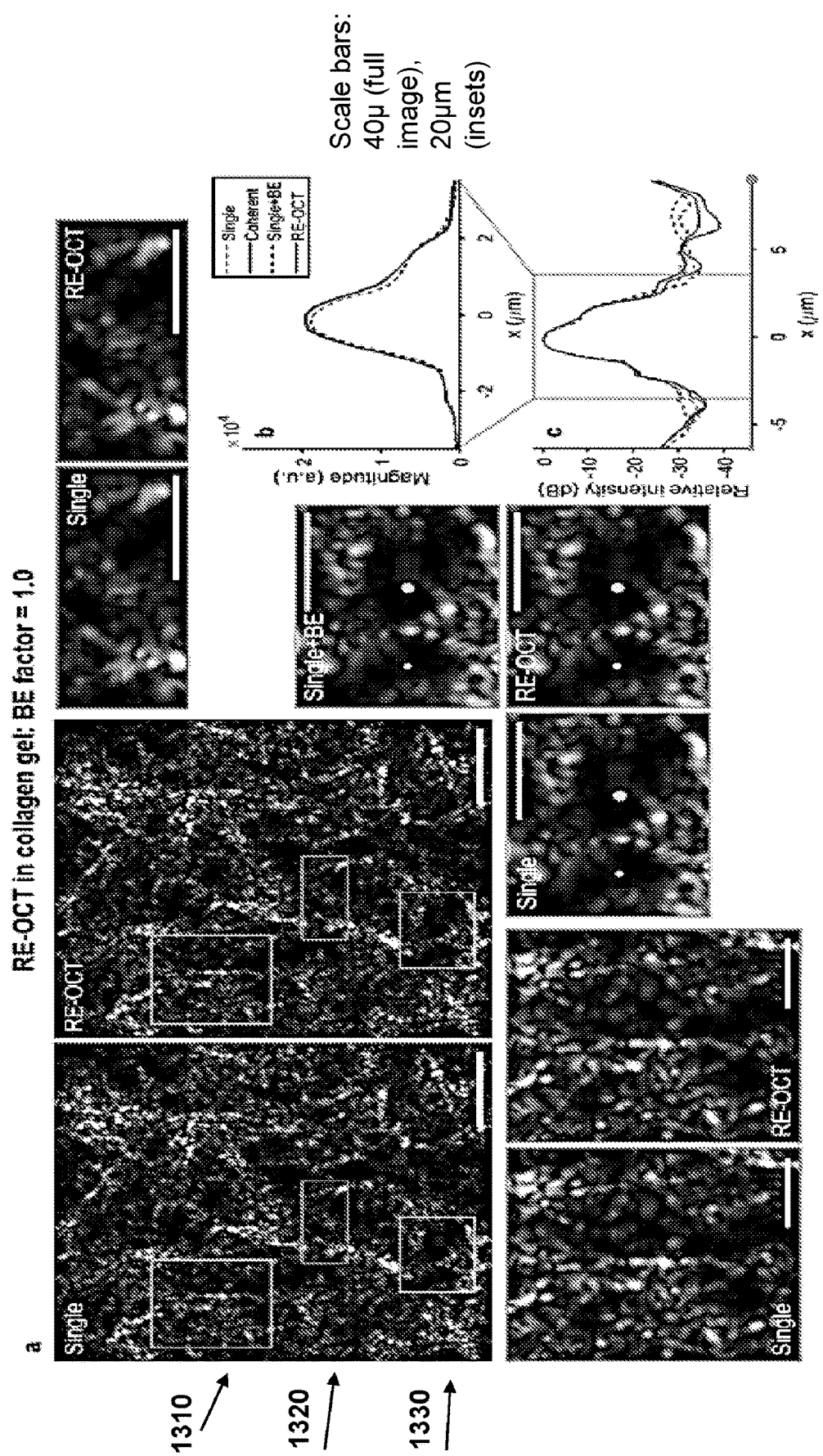
FIG. 13 shows RE-OCT in collagen gel where BE factor is 1.0.

FIG. 13 shows RE-OCT in collagen gel where BE factor is 1.0.

In some implementations, RE-OCT can be applied to more complex biological samples. FIG. 13 shows RE-OCT in fibrous collagen gel (2 mg/mL, polymerized at 4C→22C→37C). In Red inset (1310), as BE factor increases, fibers get narrower and low-magnitude features becomes more apparent as signal is localized in space. Similar effects observed in Blue inset (1320). Green inset (1330) also shows bandwidth-expanded single-shot image (single+BE) for comparison, with cross-sectional line profile across a fiber (from small to larger green dots). Linear scale indicates fiber width narrow and peak magnitude increase up to BE factor=2, and bandwidth-expanded single-shot image (single+BE) also narrows, but peak magnitude does not improve as much. Log scale indicates effect of BE on noise leads to decreasing SBR, and a higher background is observed in bandwidth-expanded single-shot image (single+BE). Overdoing BE degrades image quality without improving resolution further.

Figure 14:
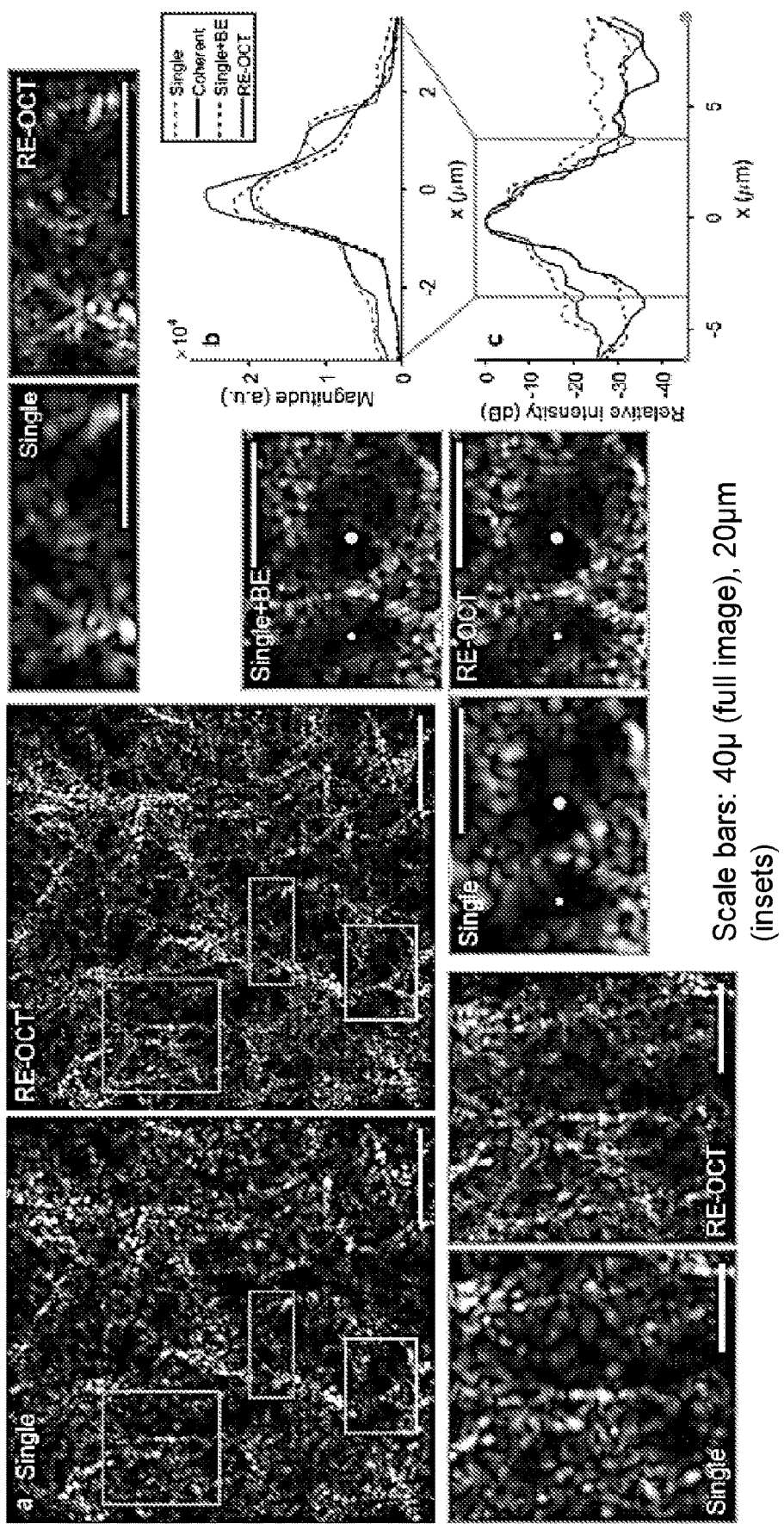
FIG. 14 shows RE-OCT in collagen gel where BE factor is 2.0.

FIG. 14 shows RE-OCT in collagen gel where BE factor is 2.0. Best performance is observed when BE factor is 2. Previously, best performance can be observed when BE factor is 2.4 in silicone phantom.

Figure 15:
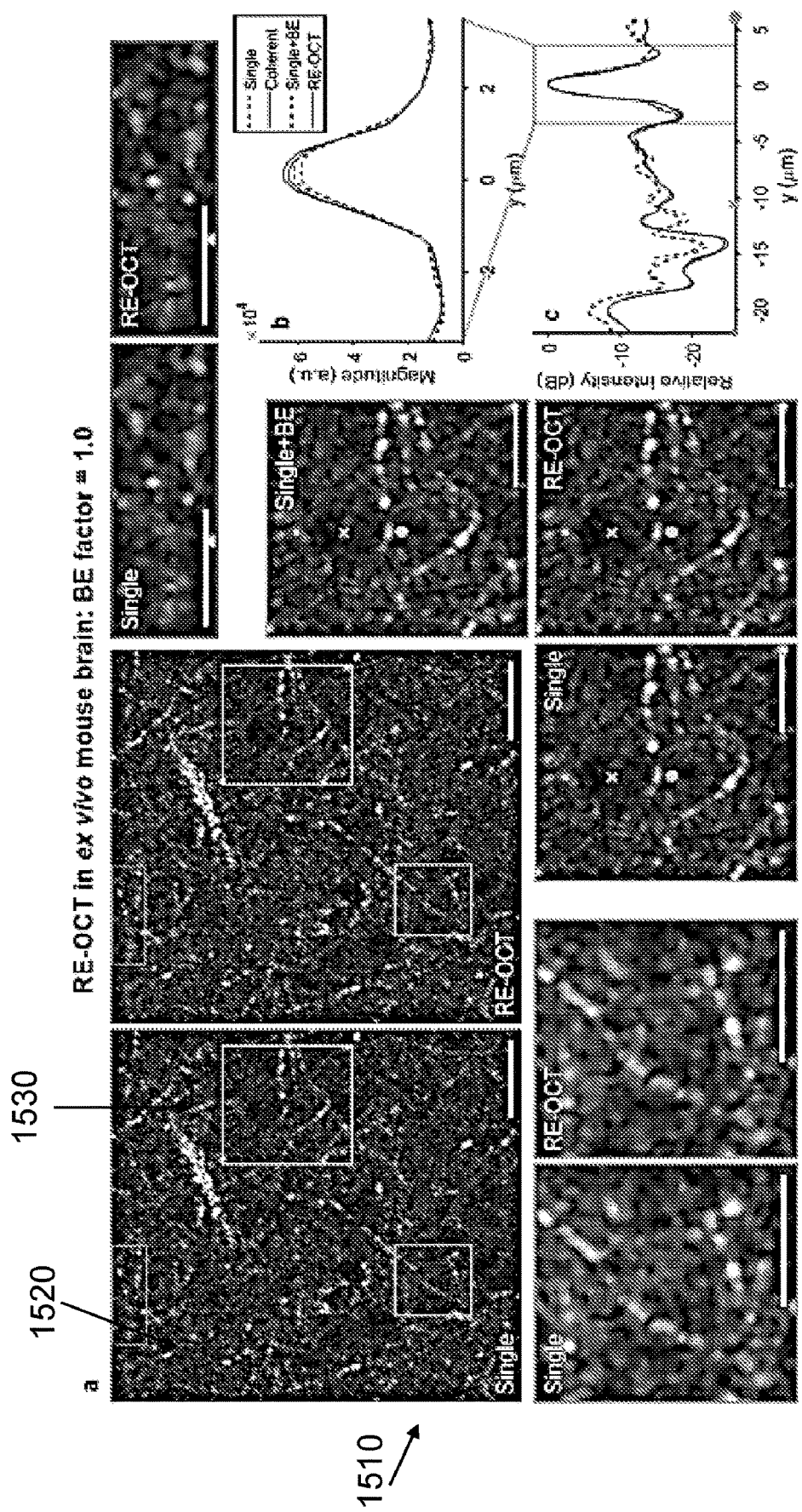
FIG. 15 shows RE-OCT in ex vivo mouse brain where BE factor is 1.0.

FIG. 15 shows RE-OCT in ex vivo mouse brain where BE factor is 1.0. RE-OCT can be applied to biological tissue. Specifically, FIG. 15 shows image of myelination in cerebral cortex in cortical layer I (~100 um below surface). Red (1510) and Blue (1520) insets show similar effects as in collagen. When narrowing myelinated axons (Red), weak features become more apparent (Blue). Green inset (1530) also shows bandwidth-expanded single-shot image (single+BE) for comparison, with cross-sectional line profile across a fiber like in collagen, x marks neuron which shows up as dark circle on OCT image. Like in collagen, linear scale corresponds to narrowing of fiber width and increase peak magnitude up to BE factor=2, and bandwidth-expanded single-shot image (single+BE) does not increase peak magnitude. Like in collagen, log scale corresponds to effect of BE on increasing noise, in this case, increasing scattering signal inside neuron. Without coherent-average noise suppression in bandwidth-expanded single-shot image (single+BE), noise exceeds scattering signal of surrounding brain tissue and lose visibility of neuron.

Figure 16:
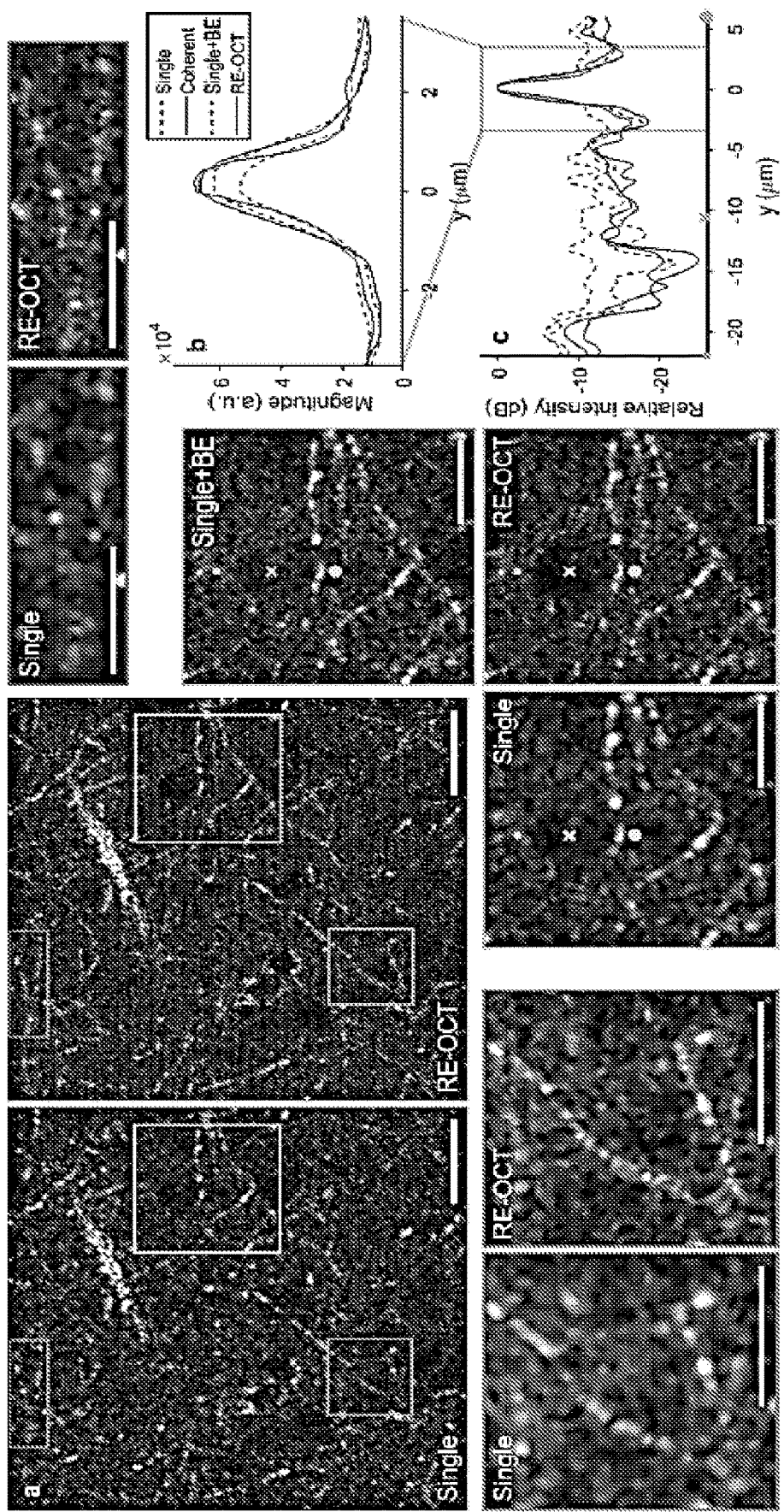
FIG. 16 shows RE-OCT in ex vivo mouse brain where BE factor is 2.0.

FIG. 16 shows RE-OCT in ex vivo mouse brain where BE factor is 2.0. Best performance is observed at BE factor=2 like in collagen.

Figure 17:
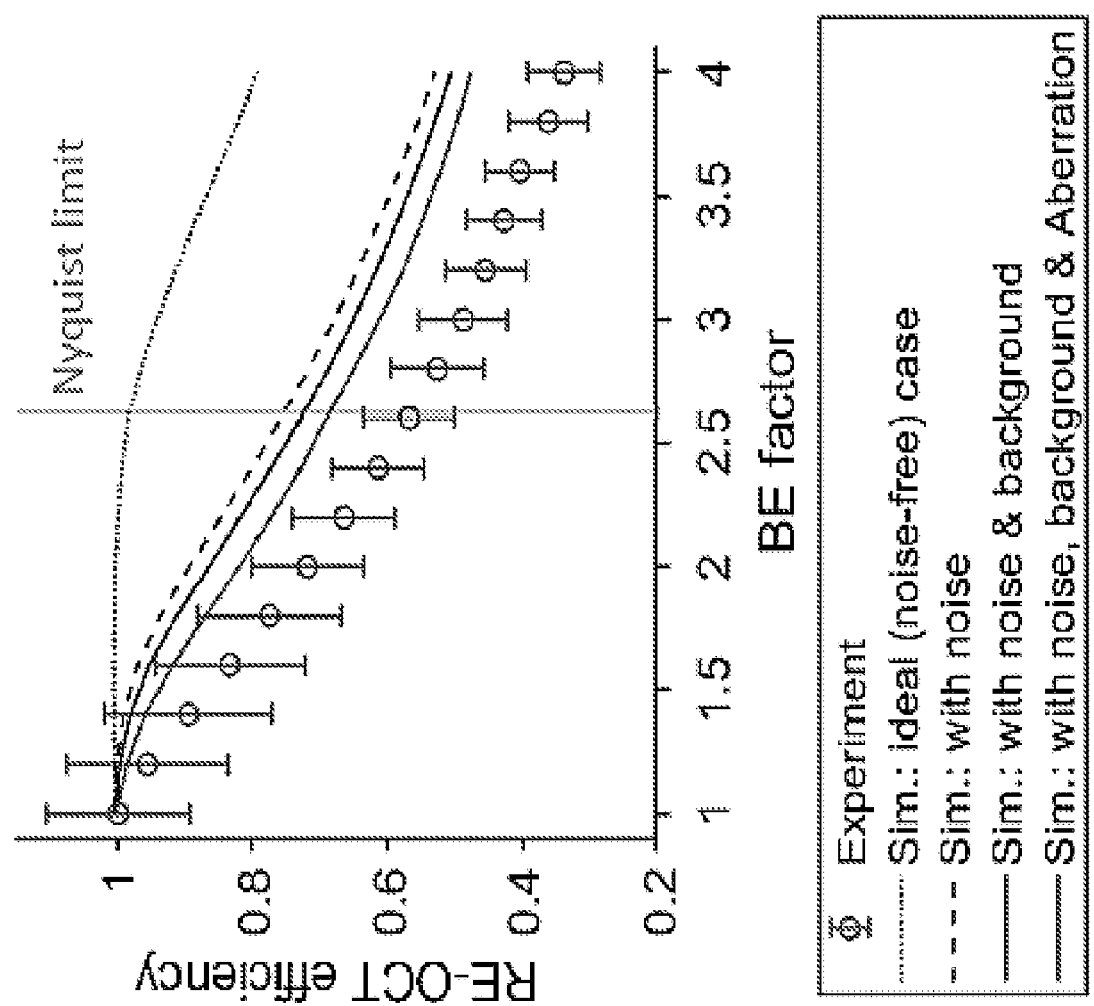
FIG. 17 shows a comparison to simulation.

FIG. 17 shows a comparison to simulation. RE-OCT efficiency can be obtained by dividing the resolution improvement by BE factor. Theoretically expected RE-OCT efficiency is 1. Upper limit is achieved only by ideal (noise-free) case. It deviates from one beyond Nyquist limit. Noise degrades resolution. RE-OCT efficiency decreases with increasing BE factor. Background (silicone scattering) and aberrations further degrade resolution for all BE factors.

Figure 18A:
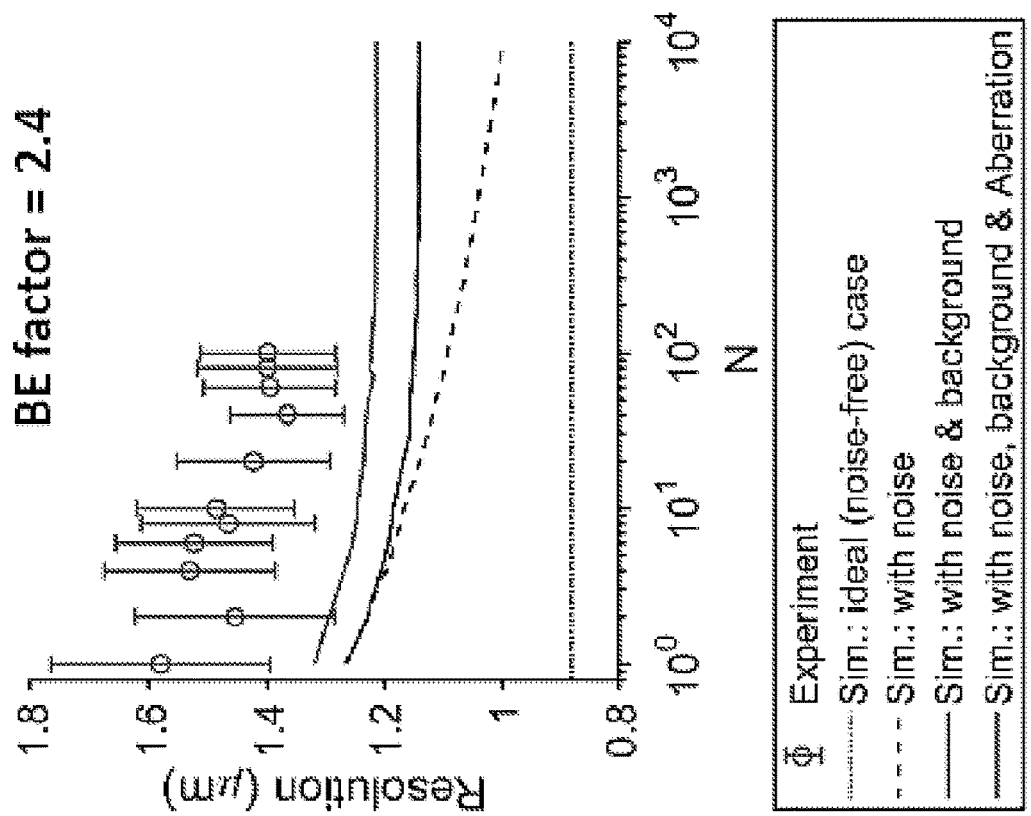
FIGS. 18A and 18B show system noise limits achievable resolution for a given BE factor.
Figure 18B:
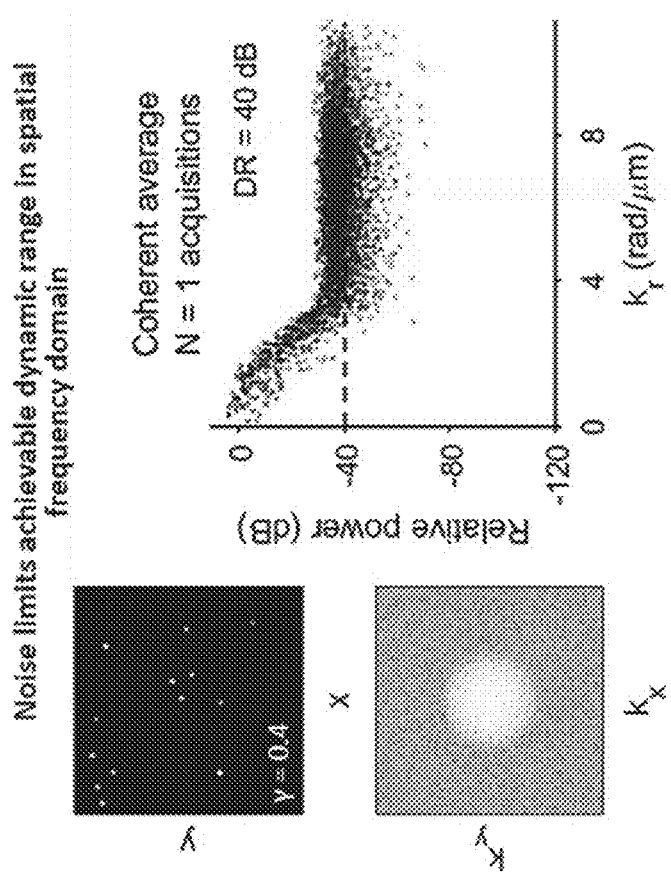

Comparing experimental results to simulated data (includes Gaussian PSFs, random noise, silicone background scattering, aberrations), a resolution improvement is expected to follow amount of BE, and it defines RE-OCT efficiency. The theoretical limit is only achieved in ideal case with no noise. Noise limits resolution improvement, and effect gets more severe with larger BE factor. On top of noise, background scattering and aberrations further limit resolution at all BE factors. This suggests that system noise is the main limiting factor for RE-OCT FIGS. 18A and 18B show system noise limits achievable resolution for a given BE factor.

For a constant BE factor, better resolution is achieved with lower noise (i.e., coherent average over more N). In spatial frequency, noise determines dynamic range (DR) relatively DC and coherent average expands this DR.

FIGS. 19A-19D show the role of system noise in the spatial-frequency domain.

Figure 19B:
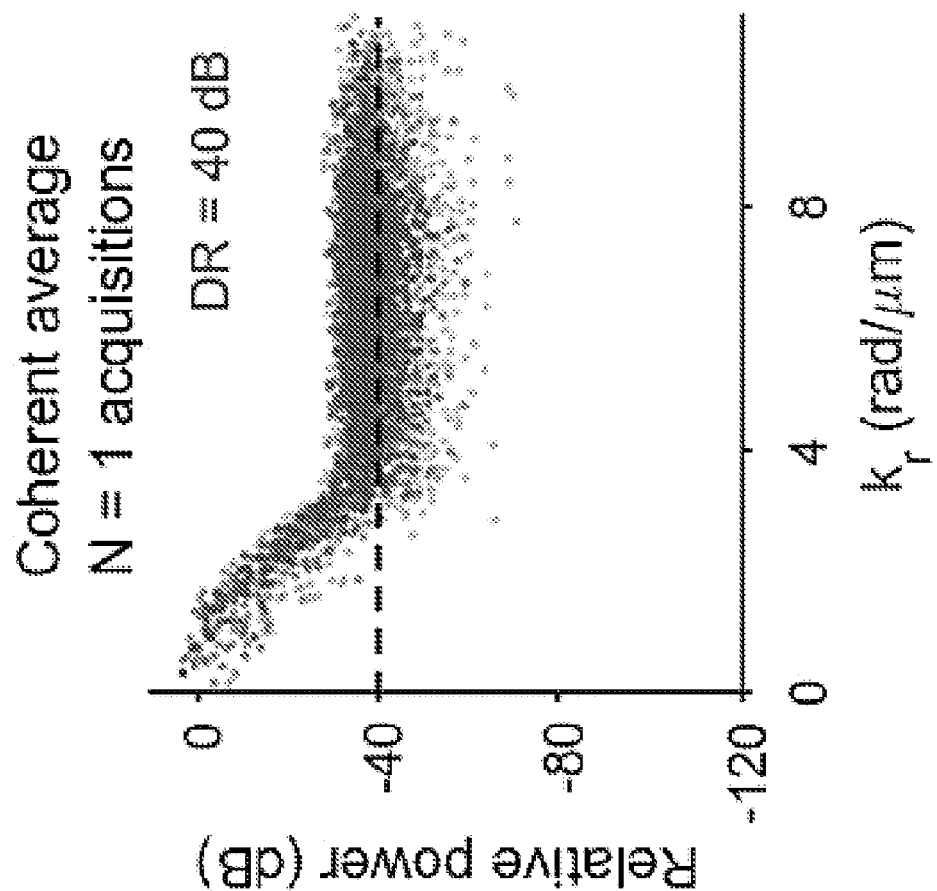
FIGS. 19A-19D show the role of system noise in the spatial-frequency domain.
Figure 19A:
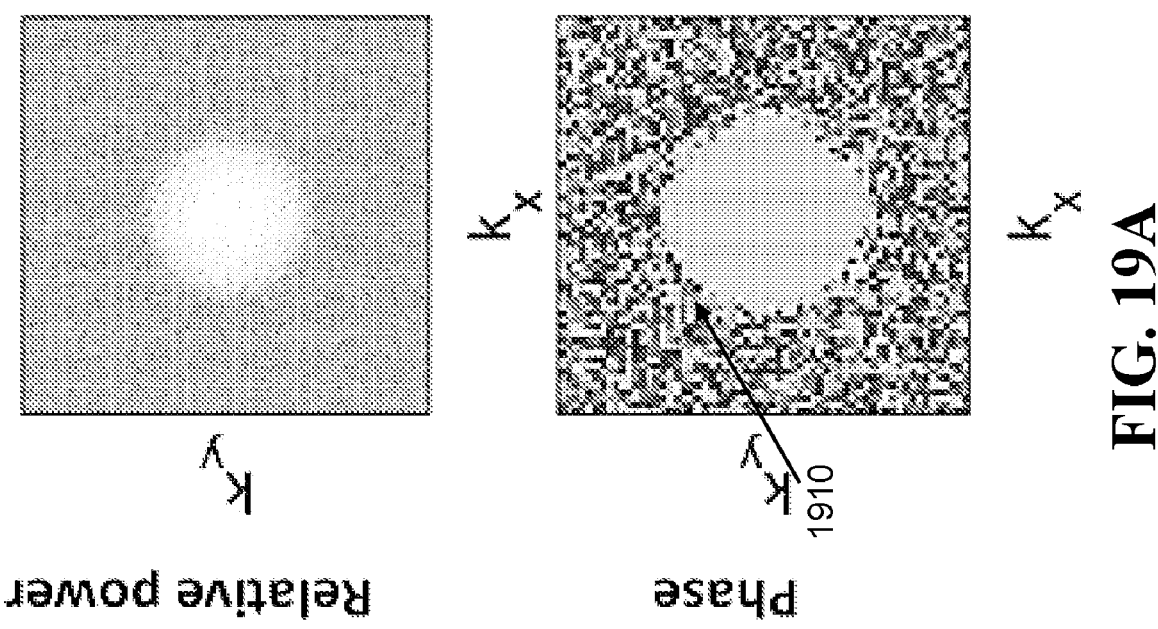
Figure 19D:
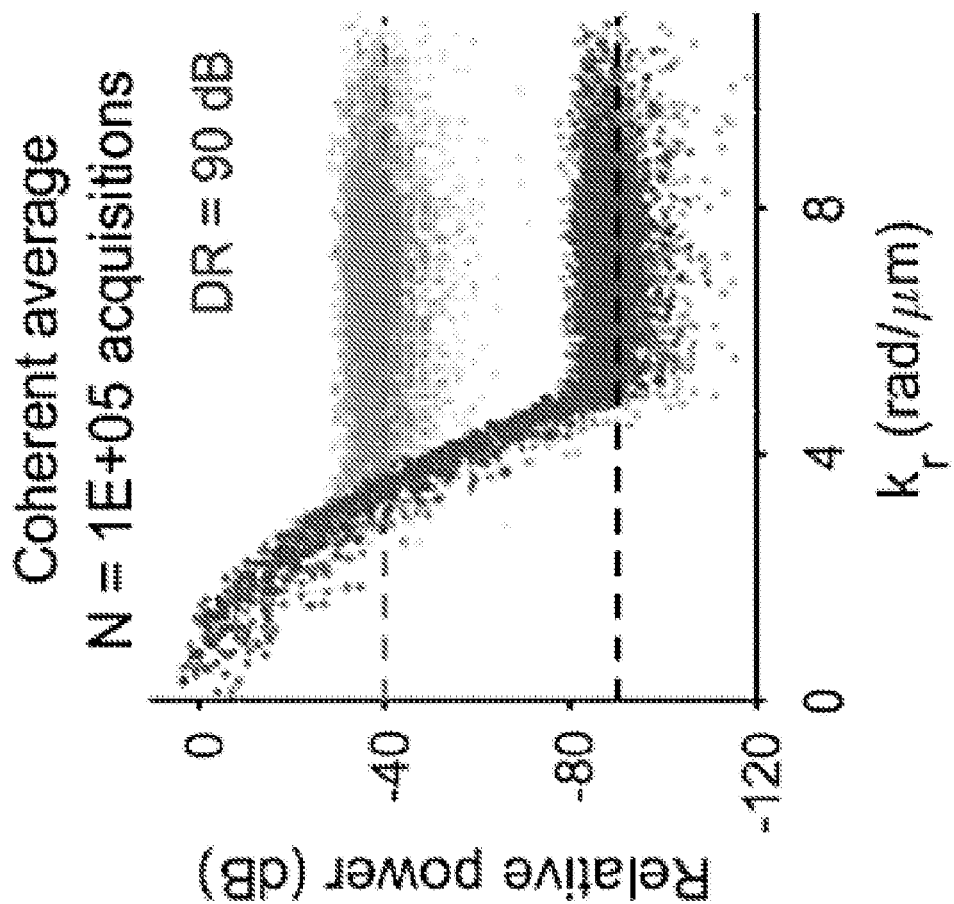
Figure 19C:
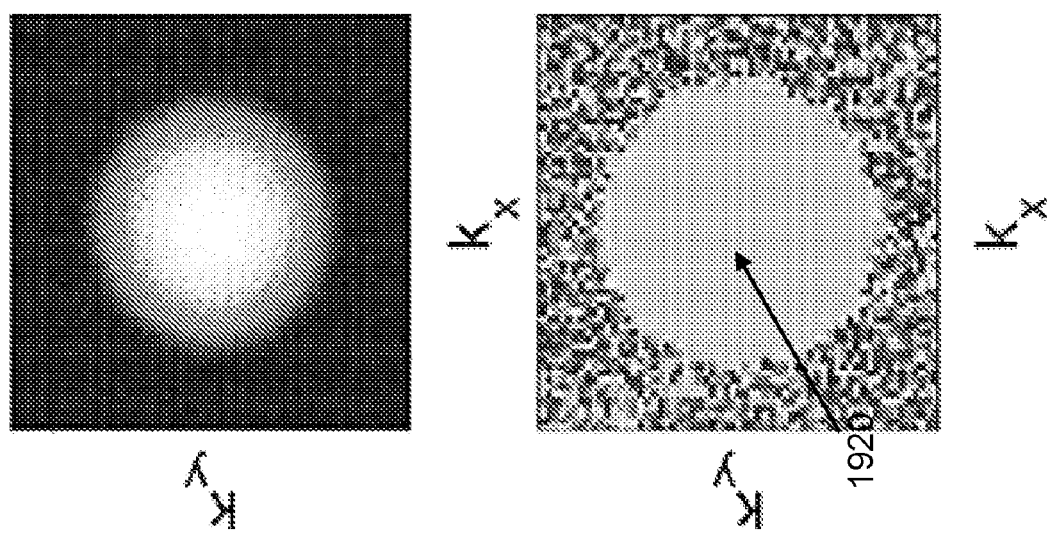
Figure 20A:
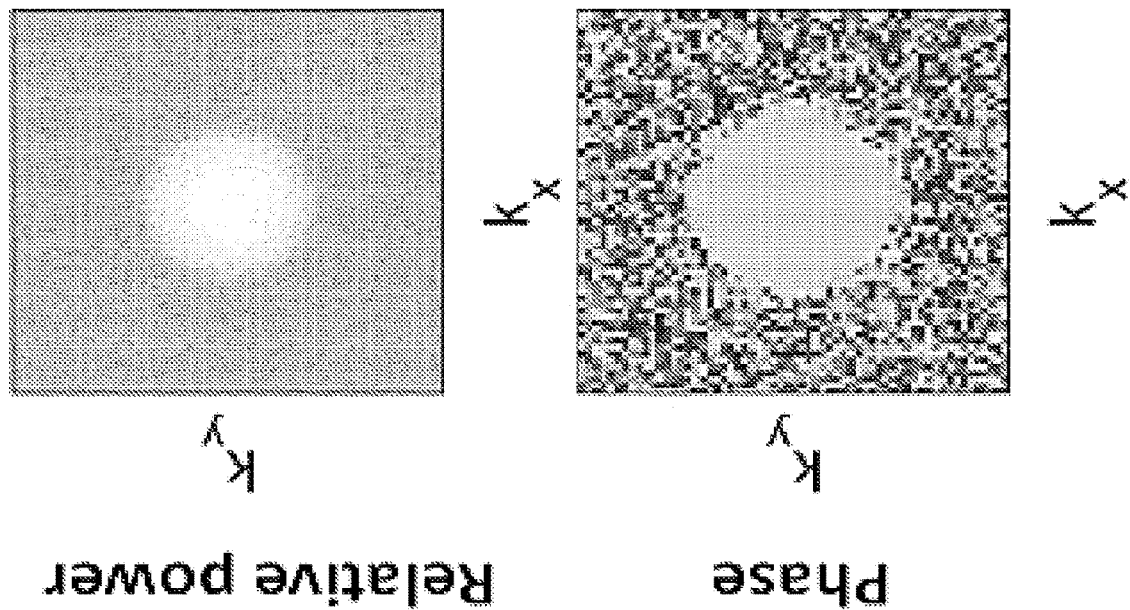
FIGS. 20A-20F show system noise limits useful bandwidth with correlated phase.
Figure 20C:
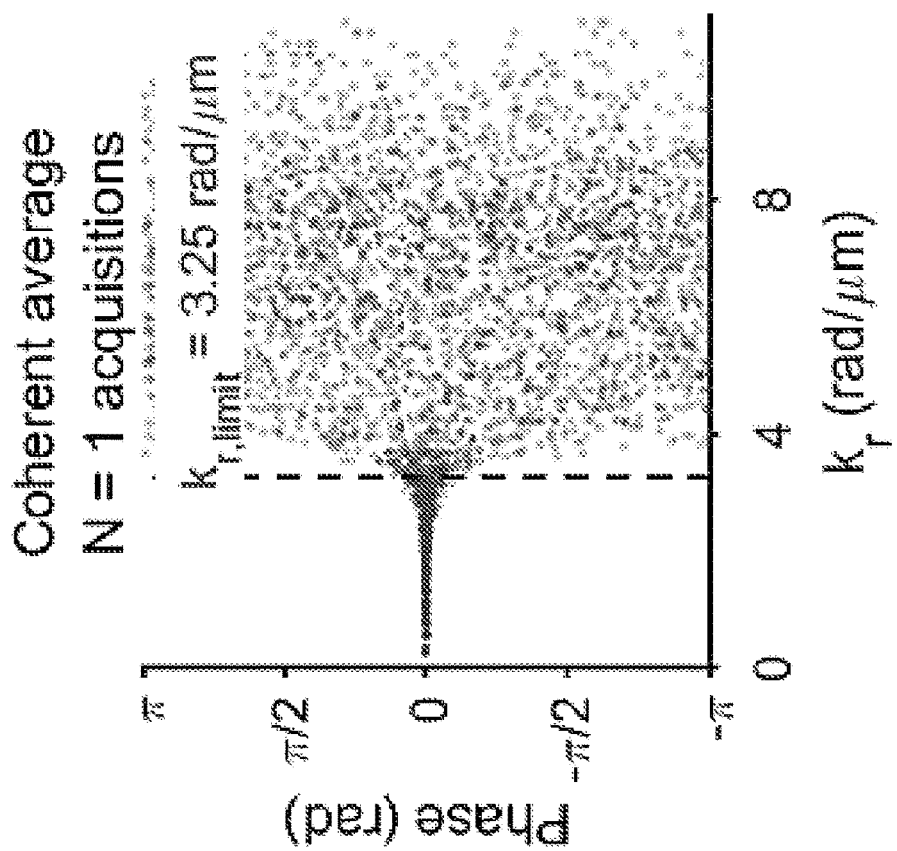
Figure 20B:
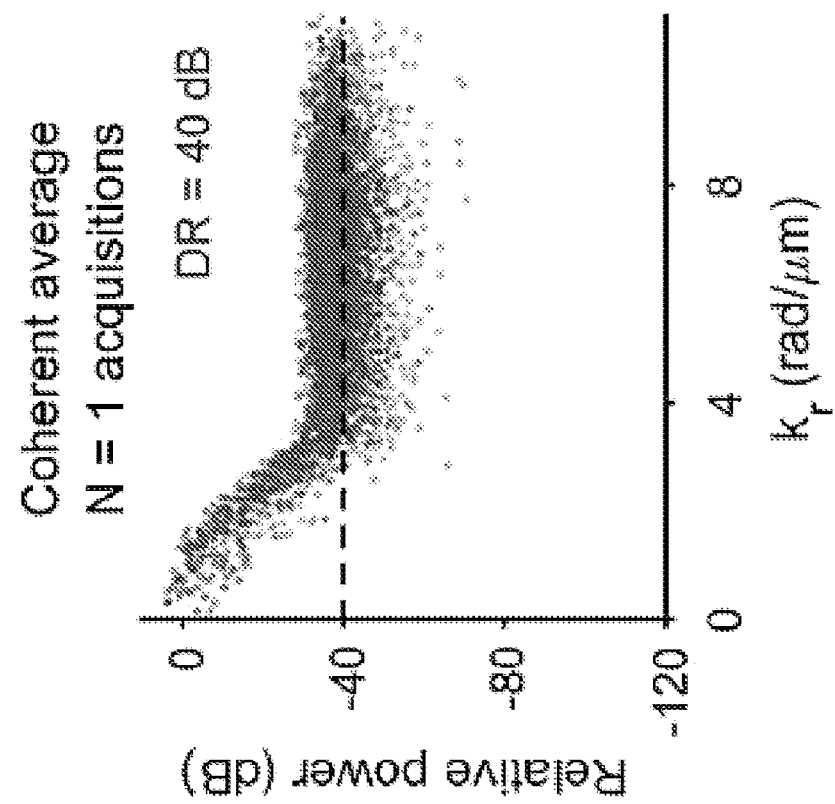
Figure 20D:
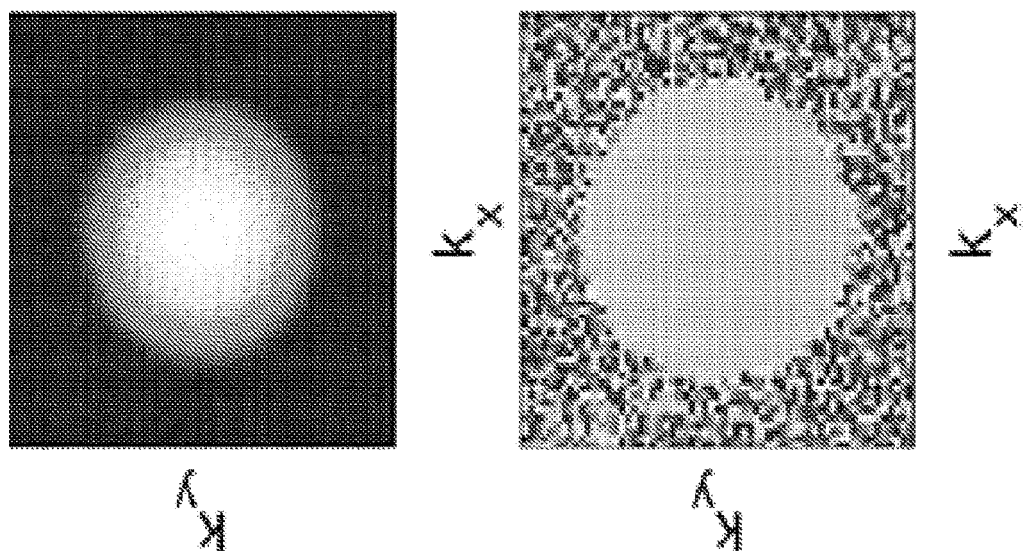
Figure 20F:
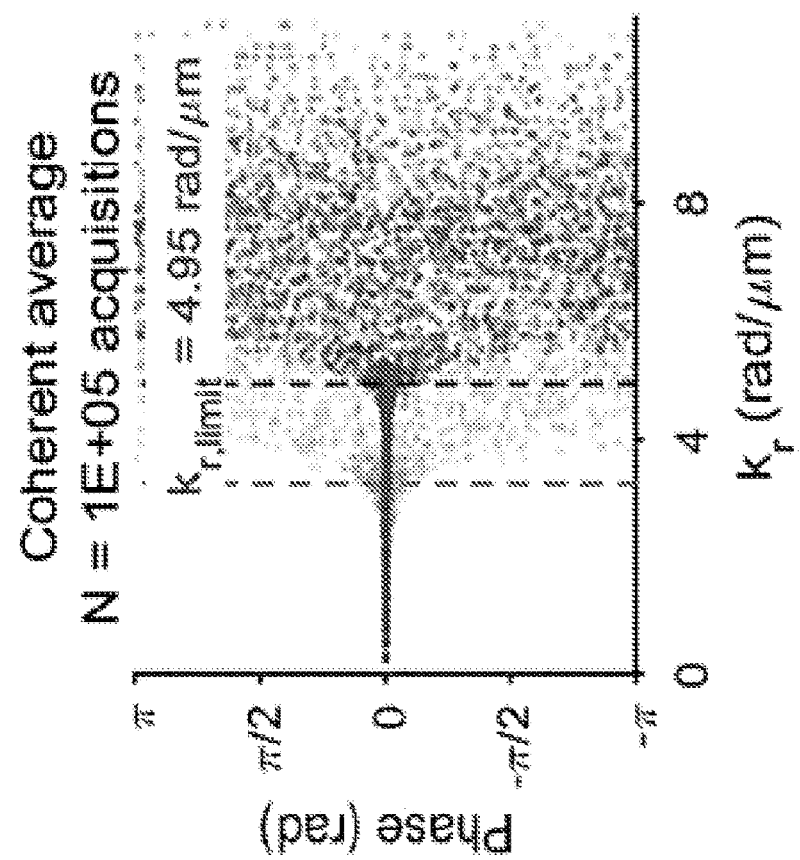
Figure 20E:
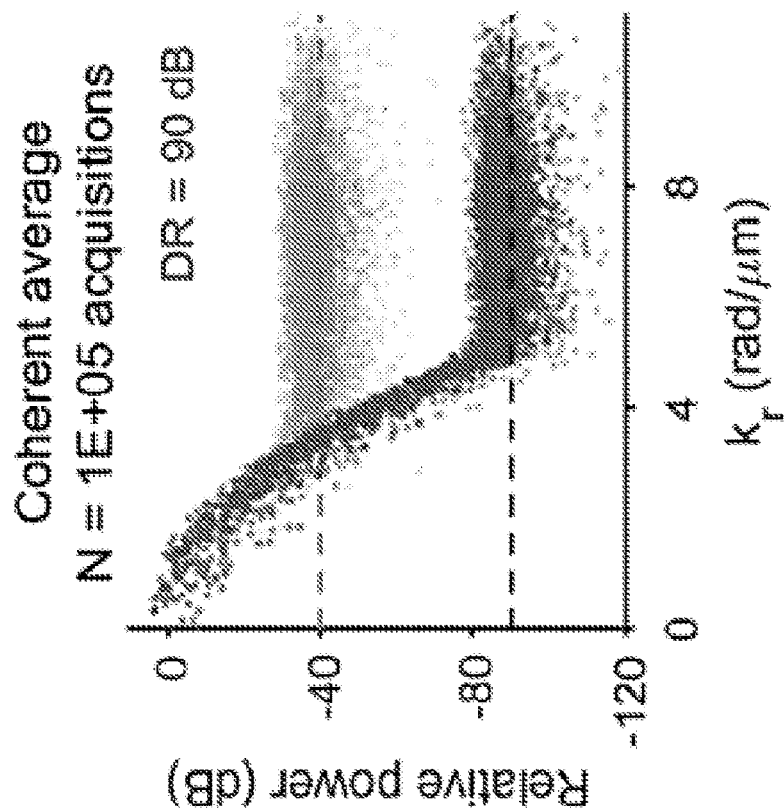

Referring to FIGS. 19A-19B, enhanced dynamic range (DR) brings signal over larger spatial bandwidth above suppressed noise floor. Phase remains correlated over a larger spatial bandwidth. With coherent average over more N, signal over larger spatial bandwidth is exposed above the suppressed noise floor. As a result, phase remains correlated over larger spatial bandwidth (i.e., 'green' flat-phase circle 1910, 1920).

FIGS. 20A-20F show system noise limits useful bandwidth with correlated phase.

Coherent-average noise suppression enhances dynamic range and expand phase-correlation limit. Phase correlation in spatial frequency is required for constructive interference and resolution. FIGS. 20A-20F show expansion of 'phase-correlation limit' in spatial frequency. This phase-correlation limit has direct implication on achievable resolution in RE-OCT, and phase correlation in spatial frequency is necessary to achieve constructive interference. Phase-correlation limit determines how much of the computationally expanded BE can actually contribute to enhancing resolution, Overdoing BE amplifies phase-decorrelated signal beyond phase correlation limit. These higher spatial frequencies cannot contribute to enhancing resolution because constructive interference cannot be achieved with decorrelated phase.

In some implementations of the disclosed technology, the resolution-enhanced optical coherent tomography (RE-OCT) offers flexibility to modify OCT image resolution without modifying the optical system. Since the resolution of an optical system is not fixed, the information capacity is invariant. In terms of the resolution-SNR tradeoff, RE-OCT 'earns' SNR to 'purchase' resolution.

In some implementations, silicone phantom can achieve 1.5× resolution improvement (from $NA_{Traditional}=0.2$ to $NA_{RE-OCT}=0.3$) while maintaining comparable SBR to traditional single-shot image.

In some implementations, biological samples can achieve an enhanced resolution and visualization of fine structures, e.g., collagen fibers and myelinated axons. Coherent average is necessary to retain weak-scattering neurons.

In some implementations, the RE-OCT resolution can be limited by SNR, background (single or multiple) scattering, and aberrations via disruption of phase correlation in spatial frequency.

The disclosed technology can be implemented in some embodiments to combine coherent-average noise suppression and computational BE, allowing more flexibility to modify resolution of image acquired by a given OCT system.

In some implementations, the RE-OCT sacrifices SNR for resolution, based on the theorem of invariance of information capacity.

In some implementations, resolution enhancement by RE-OCT is experimentally limited by presence of noise, background, and aberrations. These factors limit resolution by disrupting phase correlation in spatial frequency, and insights can be gained from looking at magnitude and phase of signal in spatial frequency domain. There may be other factors that also disrupt phase correlation in spatial frequency, and they will also contribute to limiting achievable RE-OCT resolution.

FIGS. 21A-21C show that coherent average in unstable sample requires 3D image registration and phase drift correction. Coherent-average noise suppression requires object/feature of interest to be phase-stable in time. Top row of FIG. 21 shows an average without image registration and phase drift correction. Bottom row of FIG. 21 shows an average after registering and correcting phase drift relative to first volume. Phase stability color limit is from 0 to 1.

Figures 22A, 22B, 22C:
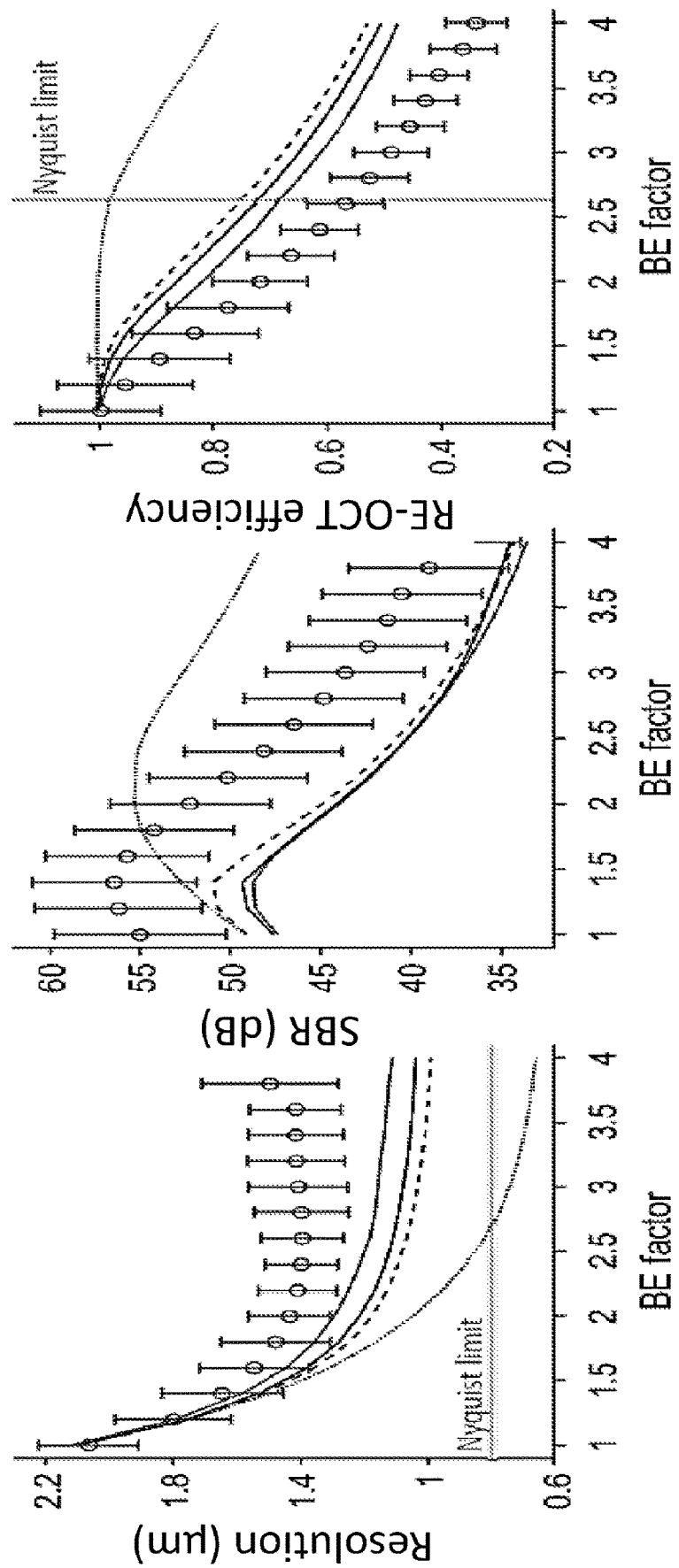
FIGS. 22A-22C show comparison to simulation.

FIGS. 22A-22C show comparison to simulation. Specifically, FIGS. 21A-21C show effects of noise, background, aberrations. Resolution reaches limit at about 1.4 um when BE factor is greater than or equal to 2.4 while SBR continues to drop. Noise is the main factor that limits resolution improvement at higher BE factors. It is possible to slightly enhance both resolution and SBR with small BE factor.

Figure 23:
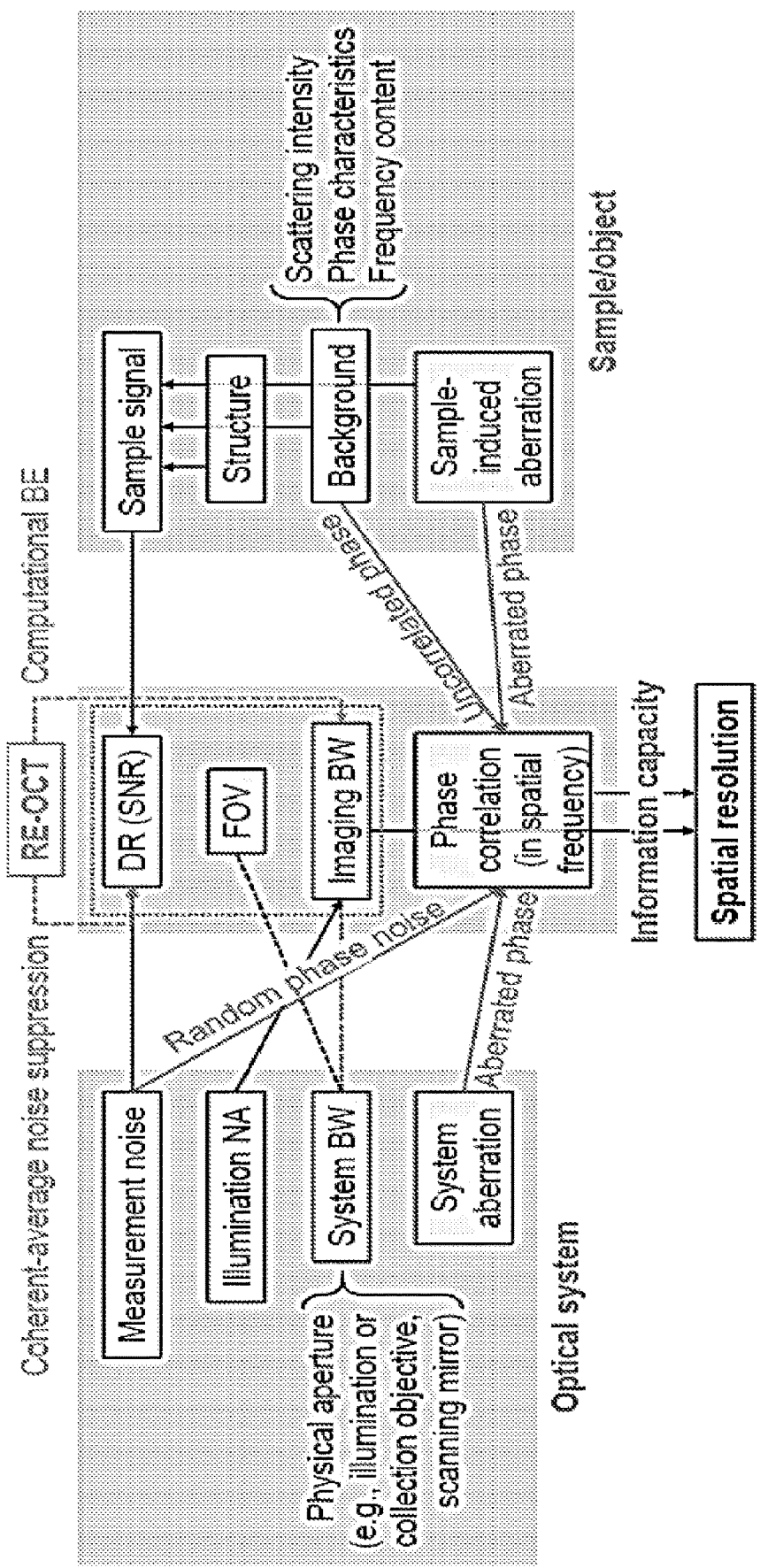
FIG. 23 shows factors that disrupt phase correlation in spatial frequency.

FIG. 23 shows factors that disrupt phase correlation in spatial frequency in implementing the disclosed RE-OCT. Several factors can disrupt phase correlation in spatial frequency and contribute in some way to limit the achievable high resolution. These factors can be related to optical system or sample being imaged itself.

The RE-OCT based on the disclosed technology can act on: (1) measurement noise, which is the main factor that limit phase correlation in spatial frequency, to enhance DR; and (2) imaging BW by boosting up Gaussian tail within objective aperture limit.

Figure 24:
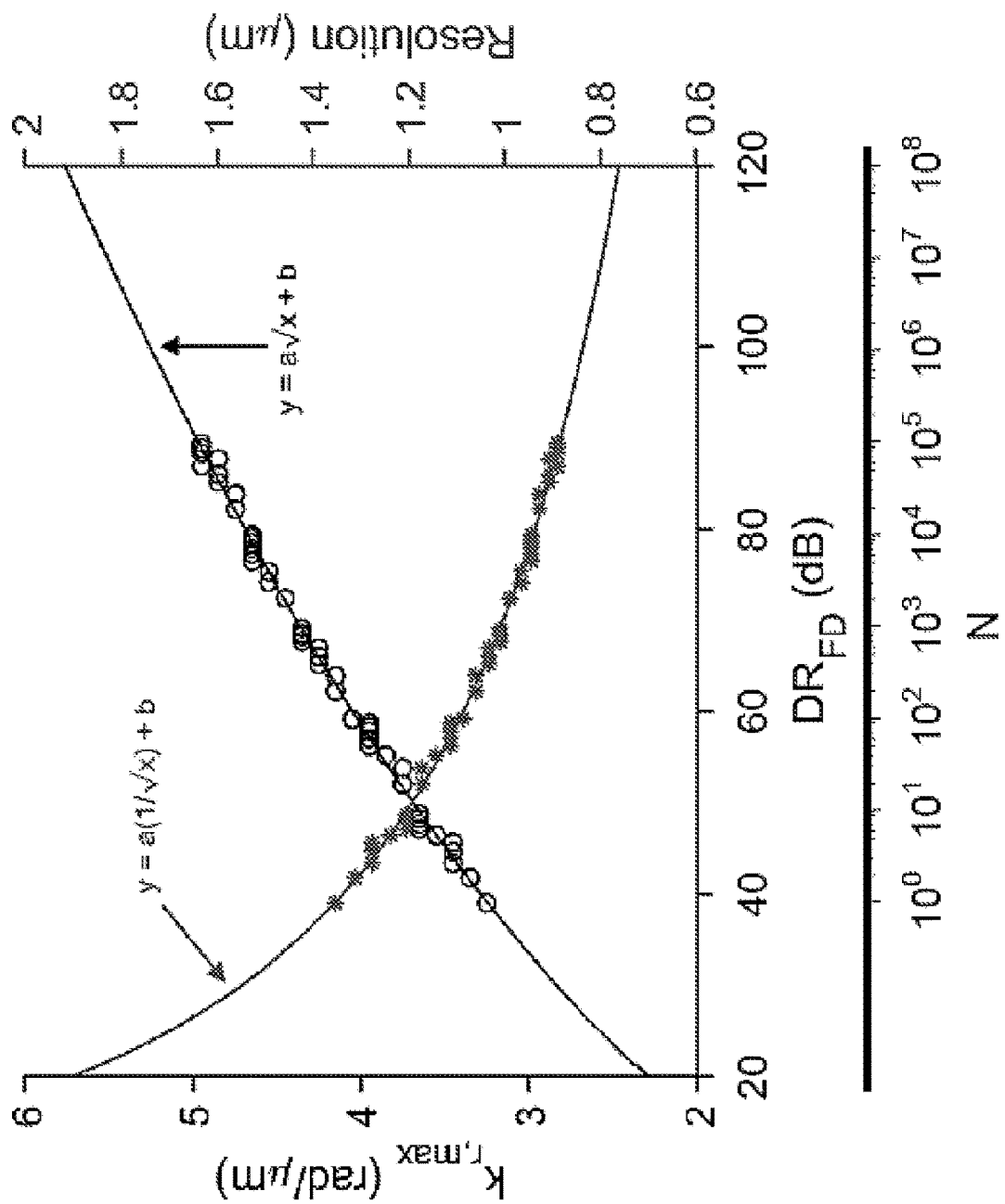
FIG. 24 shows noise-limited dynamic range, phase correlation, and resolution.

FIG. 24 shows noise-limited dynamic range, phase correlation, and resolution. Noise limits available DR in spatial-frequency domain, and coherent average over more N increases DR. Larger DR exposes signal over larger spatial bandwidth above system noise floor, and phase-correlation limit (k_r,max) increases with sqrt(DR) (power spectrum is quadratic on log scale). This means resolution limit (resolution at phase-correlation limit bandwidth) improves with 1/sqrt(DR).

Information Capacity of Imaging System

Shannon's information capacity (1D, in bits):

$$C = B\log_2(1 + s/n) = \int_0^B \log_2\left(1 + \frac{s(f)}{n(f)}\right)df \qquad \text{(Eq. 2)}$$

where B indicates bandwidth, s indicates signal power, n indicates noise power, and f indicates frequency.

Cox and Sheppard's information capacity (3D space+time, in log base 10):

$$C=(2L_xB_x+1)(2L_yB_y+1)(2L_zB_z+1)(2TB_T+1)\log(1+s/n) \qquad \text{(Eq. 3)}$$

where L indicates FOV, T indicates duration, B indicates bandwidth, s indicates signal power, and n indicates noise power. $(2L_xB_x+1)(2L_yB_y+1)(2L_zB_z+1)$ corresponds to space-bandwidth product, $(2TB_T+1)$ corresponds to time-bandwidth product, and $$\log\left(1 + \frac{s}{n}\right)$$

corresponds to signal-to-noise ratio (SNR) (log scale).

Maximum mutual information of coherent imaging through turbid media based on integral form of Shannon's information capacity is express as follows:

$$I_{max}(y;\rho) = \max_{f(\rho);\langle\rho^2\rangle} \int_0^\infty \int_0^\infty f(\rho)f(y|\rho) \times \log_2\left\{\frac{f(y|\rho)}{\int_0^\infty f(\rho')f(y|\rho')d\rho'}\right\} dy\, d\rho \quad \text{(Eq. 4)}$$

where y indicates detected signal, ρ indicates mean reflectance, and f(y|p) is probability density function for detecting y when p is mean reflectance.

Resolution-Enhanced OCT and Expanded Framework of Information Capacity and Resolution in Coherent Imaging Spatial resolution in conventional optical microscopy has traditionally been treated as a fixed parameter of the optical system. The disclosed technology can be implemented in some embodiments to enhance transverse resolution in beam-scanned optical coherence tomography (OCT) beyond its aberration-free resolution limit, without any modification to the optical system. Based on the theorem of invariance of information capacity, resolution-enhanced (RE)-OCT navigates the exchange of information between resolution and signal-to-noise ratio (SNR) by exploiting efficient noise suppression via coherent averaging and a simple computational bandwidth expansion procedure. A resolution enhancement of 1.5× relative to the aberration-free limit while maintaining comparable SNR in silicone phantom. RE-OCT can significantly enhance the visualization of fine microstructural features in collagen gel and ex vivo mouse brain. Beyond RE-OCT, our analysis in the spatial-frequency domain leads to an expanded framework of information capacity and resolution in coherent imaging that contributes new implications to the theory of coherent imaging. RE-OCT can be readily implemented on most OCT systems worldwide, immediately unlocking information that is beyond their current imaging capabilities, and so has the potential for widespread impact in the numerous areas in which OCT is utilized, including the basic sciences and translational medicine.

The enhancement of resolution has been an important and on-going pursuit in all fields of imaging, including coherent and incoherent optical microscopy. One approach for resolution enhancement is spatial-frequency bandwidth expansion [i.e., increasing the numerical-aperture (NA)] via aperture synthesis. This family of techniques utilizes multiple measurements of the sample that provide access to different spatial frequencies beyond the bandwidth support of a single measurement. A well-known technique in incoherent microscopy is structured illumination microscopy (SIM), which uses different illumination patterns to shift the spatial frequency coverage of the optical system. Virtually structured detection (VSD) adopts a similar principle but (virtually) applies a digital spatial modulation in the detection path. In coherent microscopy, the bandwidth support of the optical system can be shifted via use of multiple illumination angles, as has been implemented with off-axis holography and Fourier ptychography (which performs incoherent imaging at different illumination angles, combined with phase retrieval methods to reconstruct the complex optical field).

In optical coherence tomography (OCT), interferometric synthetic aperture microscopy (ISAM) utilizes synthetic aperture methods to overcome the trade-off between resolution and depth-of-field, in order to reconstruct depth-invariant focal-plane resolution from a single volumetric measurement with the optical focus at a fixed depth. Combining full-field OCT with holography, holoscopy can similarly achieve focal-plane resolution across all depths. The VSD approach has also been applied to OCT. More recently, optical coherence refraction tomography (OCRT) utilizes sample rotation combined with an (incoherent) Fourier synthesis technique reminiscent of X-ray computed tomography to effectively 'replace' the lateral resolution of a low-NA imaging beam by the superior axial resolution of OCT. Similarly, sample shifting (sub-resolution translation) has been combined with multi-frame super-resolution image processing to reconstruct an OCT tomogram with improved resolution. Meanwhile, deconvolution approaches based on iterative numerical optimization (of OCT signal magnitude or intensity images) have also been implemented to enhance resolution in OCT.

Another family of techniques aims to correct aberrations in order to restore ideal focal-plane resolution. Hardware-based adaptive optics (HAO) has been implemented in coherent and incoherent microscopy. In coherent imaging, access to the complex optical field can enable computational aberration correction post-data-acquisition. Computational adaptive optics (CAO) modifies the pupil phase of complex OCT tomograms to correct both defocus and optical aberrations, in order to restore aberration-free focal-plane resolution. Indeed, reaching the ideal aberration-free resolution supported by the optical system (i.e., without entering the super-resolution regime), especially in complex media such as biological samples, is the aim of many adaptive optics or computational aberration correction methods in optical microscopy.

Spatial resolution (or equivalently, spatial-frequency bandwidth) in optical microscopy has traditionally been treated as a fixed parameter for a given optical system. However, the theorem of invariance of information capacity suggests that resolution of an optical system is a tunable parameter that can be flexibly modified without altering the optical system. Cox and Sheppard described the information capacity of an optical system as the product of its space-bandwidth products (SBP) over all spatial dimensions, time-bandwidth product (TBP), and its signal-to-noise ratio (SNR) on the logarithmic scale. The theorem of invariance of information capacity states that it is not the spatial-frequency bandwidth (and therefore resolution), but the information capacity of an optical system that is invariant. It follows that spatial resolution can, in theory, be enhanced beyond the aberration-free limit of a given optical system through an exchange of information between spatial-frequency bandwidth and SNR, while keeping the information capacity constant.

The framework of informational capacity and its invariance underscores several unique advantages of coherent over incoherent imaging. Given the same number of pixels, a coherent image inherently supports twice the information capacity of an equivalent incoherent image because each pixel is described by both magnitude and phase of the complex optical field, as opposed to a single intensity value. Using quantum Fisher information formalism, others have also shown that the resolution limit in traditional intensity-based imaging techniques can be overcome by making use of phase information. In some implementations, the scattering limit to the information capacity of depth-resolved coherent imaging (e.g., using OCT) through turbid media as a function of SNR. Furthermore, coherent averaging of complex tomograms provides a more efficient method for noise suppression than incoherent (magnitude-only) averaging in OCT, due to the decorrelation of random phase noise. Coherent averaging has also been used for multiple scattering suppression. The efficient noise suppression via coherent averaging presents an opportunity to expand the information capacity of a coherent imaging system via the enhancement of SNR.

Resolution-enhanced (RE)-OCT is a spatial-frequency bandwidth expansion approach that computationally enhances transverse spatial frequencies beyond the traditional bandwidth support (i.e., beyond the aberration-free resolution limit) of a beam-scanned OCT system. Unlike existing aperture synthesis techniques, it does not rely on diversity in the illumination schemes to access traditionally unseen spatial frequencies, and so can readily be implemented on existing OCT systems. RE-OCT is based upon the premise of information exchange between spatial-frequency bandwidth and SNR, as governed by the theorem of invariance of information capacity. It navigates this exchange of information by exploiting efficient noise suppression via coherent averaging and a simple computational bandwidth expansion procedure. RE-OCT harnesses the benefit of coherent averaging to (for the first time) enhance resolution in OCT.

In this patent document, the underlying principle of RE-OCT based on the information capacity framework will be discussed, and noise suppression via coherent averaging will be demonstrated and its impact on the OCT signal will be analyzed in not only the space, but also the spatial-frequency domain. Our analysis of the impact of coherent averaging in the transverse spatial-frequency domain provides a new perspective compared to prior work in OCT (which has only investigated the impact of coherent and incoherent averaging in the space domain). The disclosed technology can be implemented in some embodiments to provide RE-OCT that can enhance the resolution of OCT in both resolution phantom and biological samples (collagen gel and ex vivo mouse brain). In this patent document, the factors that limit resolution enhancement in RE-OCT will also be analyzed by comparing experimental results to simulations. Some embodiments of the disclosed technology ca be used to leverage insights from the analysis in the spatial-frequency domain to present an expanded framework of information capacity and resolution in coherent imaging. RE-OCT has the potential to have widespread impact since it can be readily implemented on most OCT systems without requiring any redesign of the optical system or specialized computationally-intensive algorithms.

Underlying Principle of Resolution-Enhanced OCT

Figure 25A:
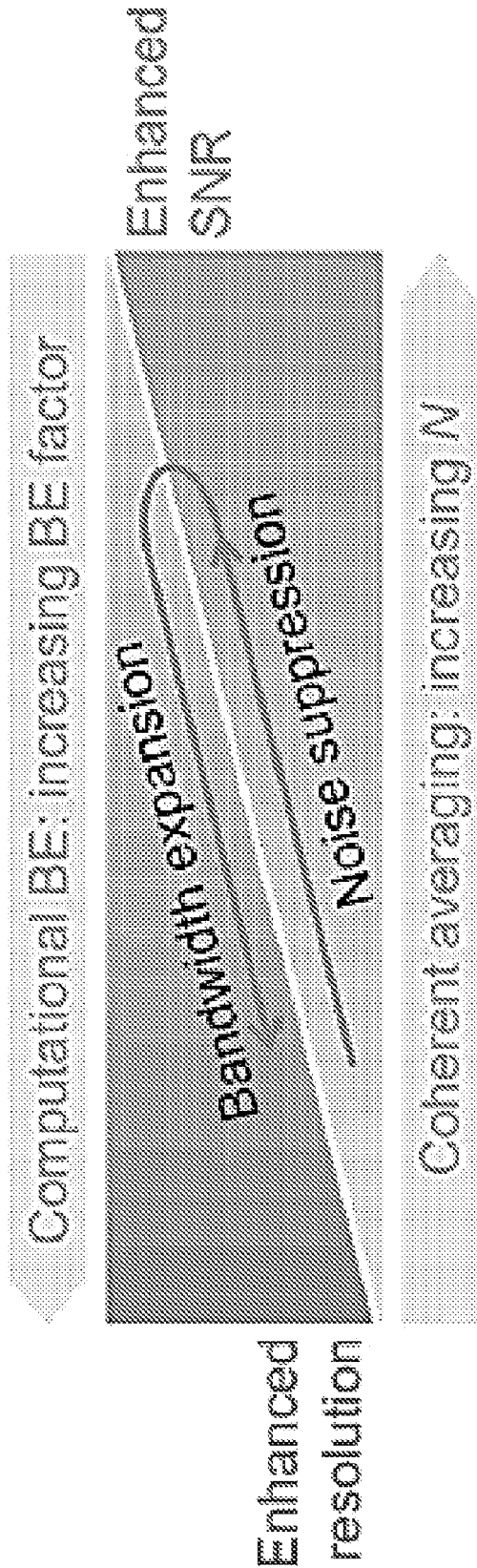
FIGS. 25A-25B show underlying principles of RE-OCT.
Figure 25B:
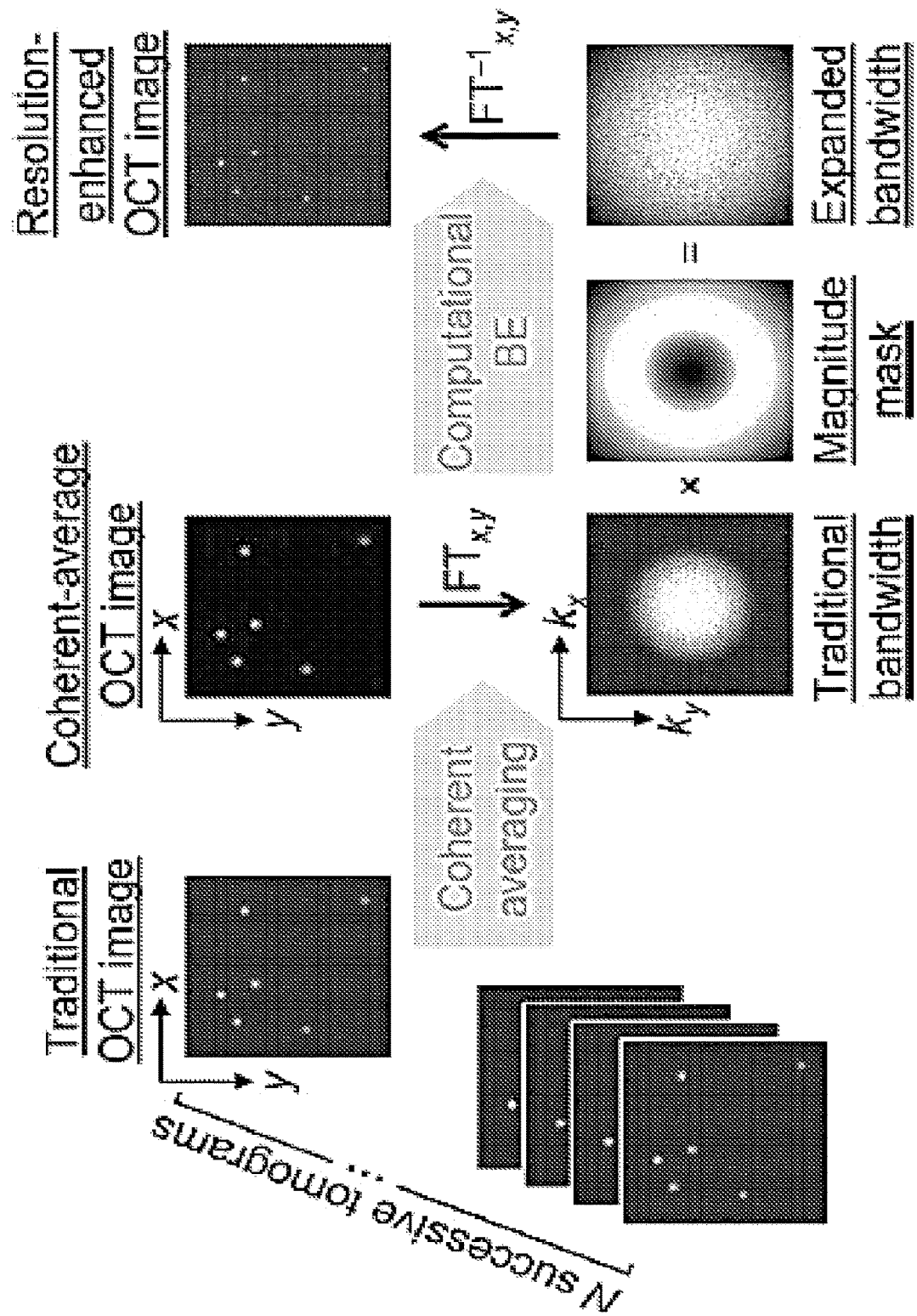

FIGS. 25A-25B show underlying principles of RE-OCT. FIG. 25A shows information exchange between resolution and SNR facilitated by noise suppression and spatial-frequency bandwidth expansion. RE-OCT utilizes coherent averaging to efficiently suppress noise and enhance SNR, then SNR is sacrificed in the computational BE procedure to enhance resolution. FIG. 25B shows illustration of RE-OCT process to implement the principle in FIG. 25A. Section IV below provides a full description of RE-OCT reconstruction procedure. BE bandwidth expansion, FT Fourier transform.

RE-OCT is a spatial-frequency bandwidth expansion approach based on the exchange of information between resolution and SNR that is supported by the underlying theorem of invariance of information capacity. In some implementations, the transverse resolution of a tomogram acquired by a beam-scanned OCT system can be enhanced via computational bandwidth expansion (BE), where signal at higher spatial frequencies is raised via multiplication by a magnitude mask in the spatial-frequency domain (i.e., magnitude-based deconvolution). This is feasible due to the under-filling of the physical aperture of the objective lens (i.e., a physical bandwidth limit) that is implemented in the ubiquitous telecentric scanning scheme (FIG. 32(b)) used by most OCT systems worldwide. However, deconvolution inherently amplifies noise and degrades the SNR of the image. To address this problem, the SNR penalty associated with computational BE can be compensated by first suppressing the system noise. Here, one efficient way in OCT is by coherently averaging multiple successively acquired complex tomograms. The underlying principle of RE-OCT is illustrated in FIGS. 25A-25B. RE-OCT utilizes coherent averaging for efficient noise suppression to 'earn' SNR, which can be used to 'purchase' resolution via computational BE.

To understand the underlying principle of RE-OCT in the context of the theorem of invariance of information capacity, Cox and Sheppard's expression for the information capacity of an optical system can be expressed as:

$$C=(2L_xB_x+1)(2L_yB_y+1)(2L_zB_z+1)(2TB_T+1)\log_2(1+s/n) \quad \text{(Eq. 5)}$$

where L, T, and B denote the spatial field-of-view (FOV), temporal duration, and bandwidth in the associated dimension, respectively. The first three terms represent the SBP along the three spatial dimensions while the fourth term represents the TBP. The last term represents the SNR (in bits), where s and n denote the average signal power and the additive noise power, respectively. Consider simply acquiring N successive tomograms of a 'static' object. Although T increases by a factor of N, the TBP remains constant because the object is known a priori to be invariant in time (i.e., infinitesimal $B_T$)-no additional information is derived from the object despite the capacity to support more information. By coherently averaging the N successive tomograms, however, the originally redundant increase in T is now "encoded" in the finite SNR term via the reduction in n. Thus, compared to the individual tomograms, the new coherent-averaged system possesses a larger information capacity with enhanced SNR (Eq. S4 below), which can be sacrificed to expand each of the transverse spatial-frequency bandwidths, $B_x$ and $B_y$. (For the full analysis of this process, see Section I below). One scenario is to expand the bandwidth equally along each transverse dimension by a factor equal to the square root of the gain in SNR in order to, in principle, enhance resolution in the transverse plane by the same factor, without suffering any SNR penalty relative to the traditional single-shot tomogram (FIG. 31). However, RE-OCT is not limited to this scenario; the trade-off between resolution and SNR can be flexibly navigated by tuning the number of tomograms averaged and the BE factor applied (i.e., more SNR than the amount 'earned' from coherent averaging can be sacrificed to prioritize further resolution enhancement), as shown in FIG. 25A.

Coherent-Average Noise Suppression in Space and Spatial-Frequency Domains

Figure 26A:
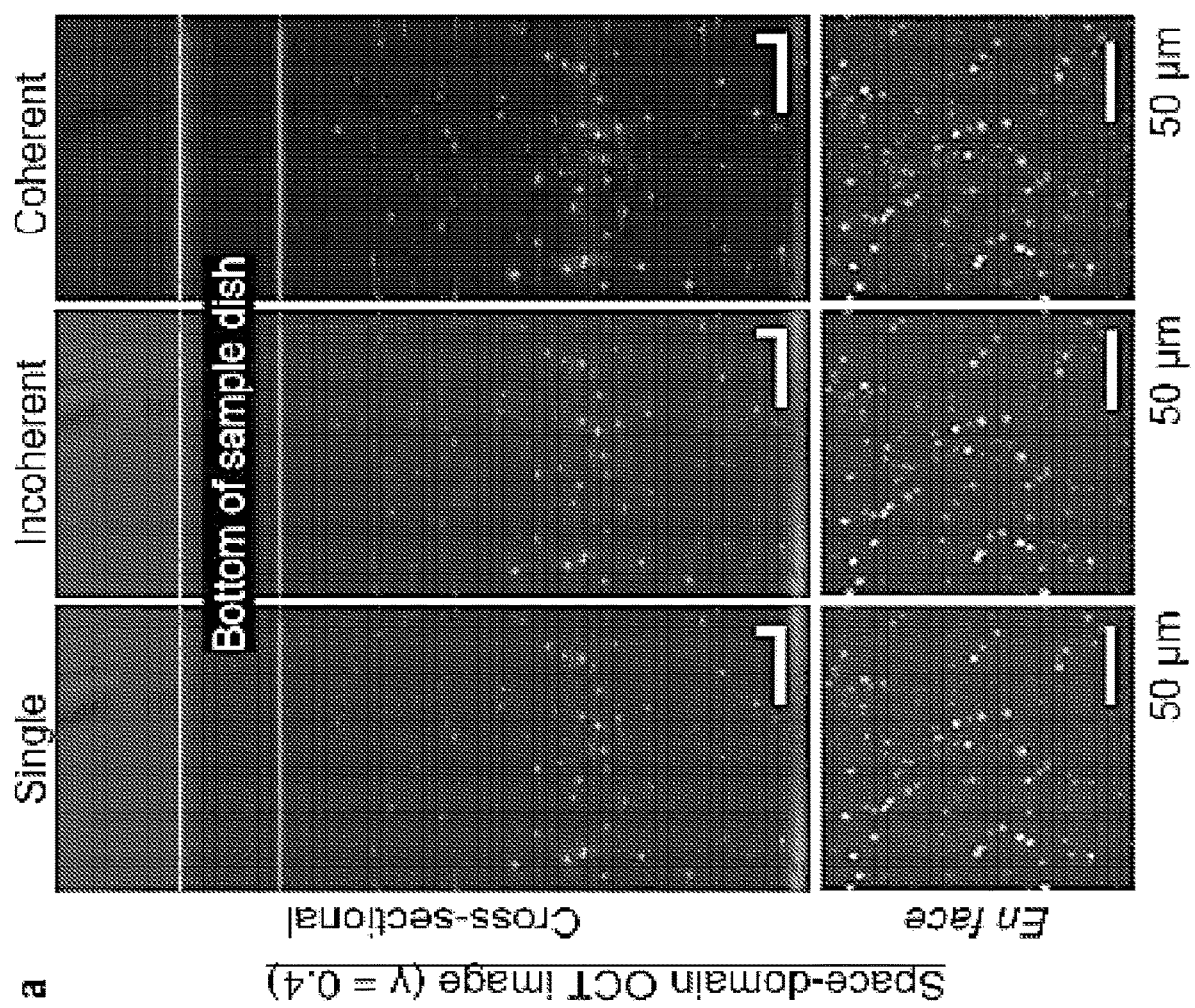
FIGS. 26A-26E show coherent-average noise suppression with 100 acquisitions in silicone phantom.
Figure 26B:
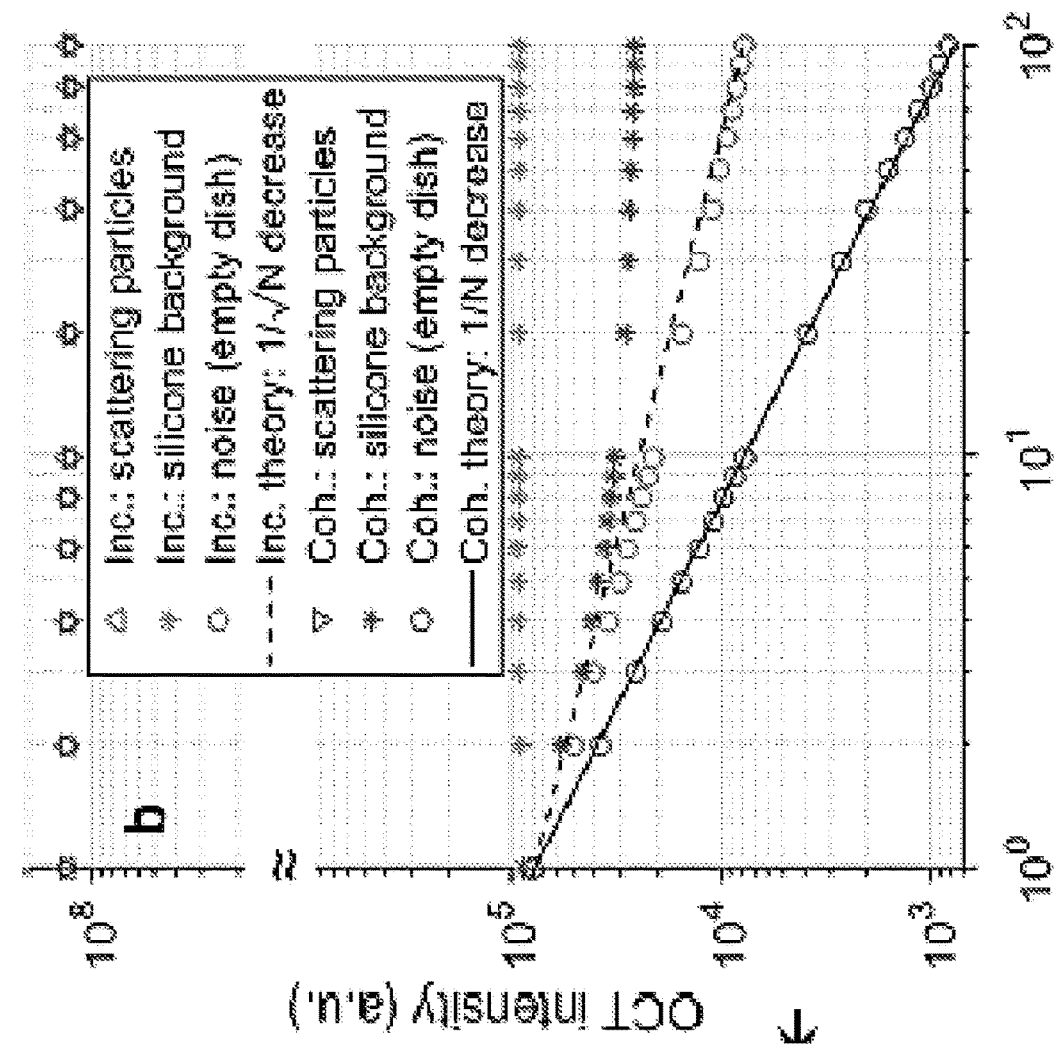
Figure 26C:
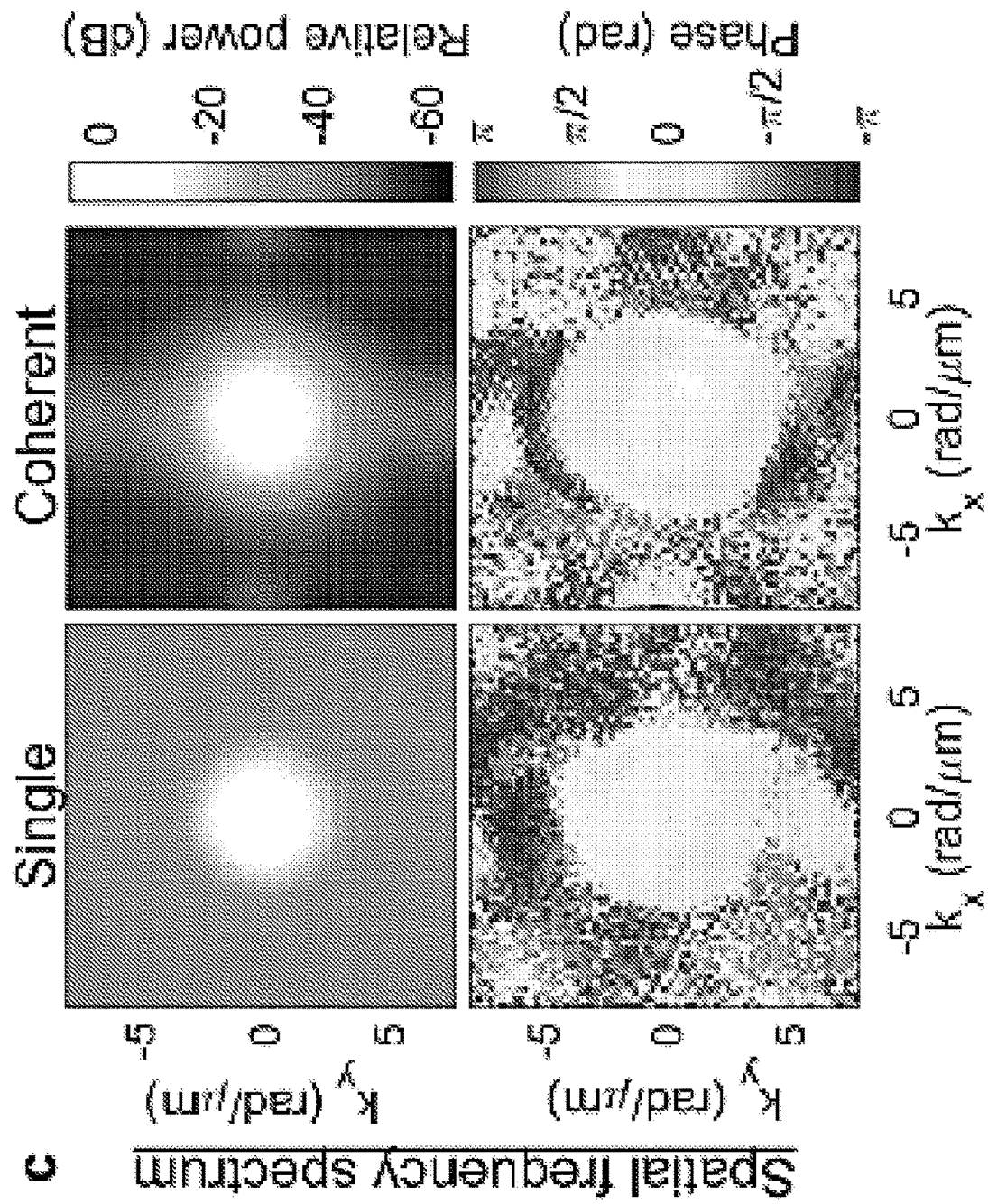
Figure 26D:
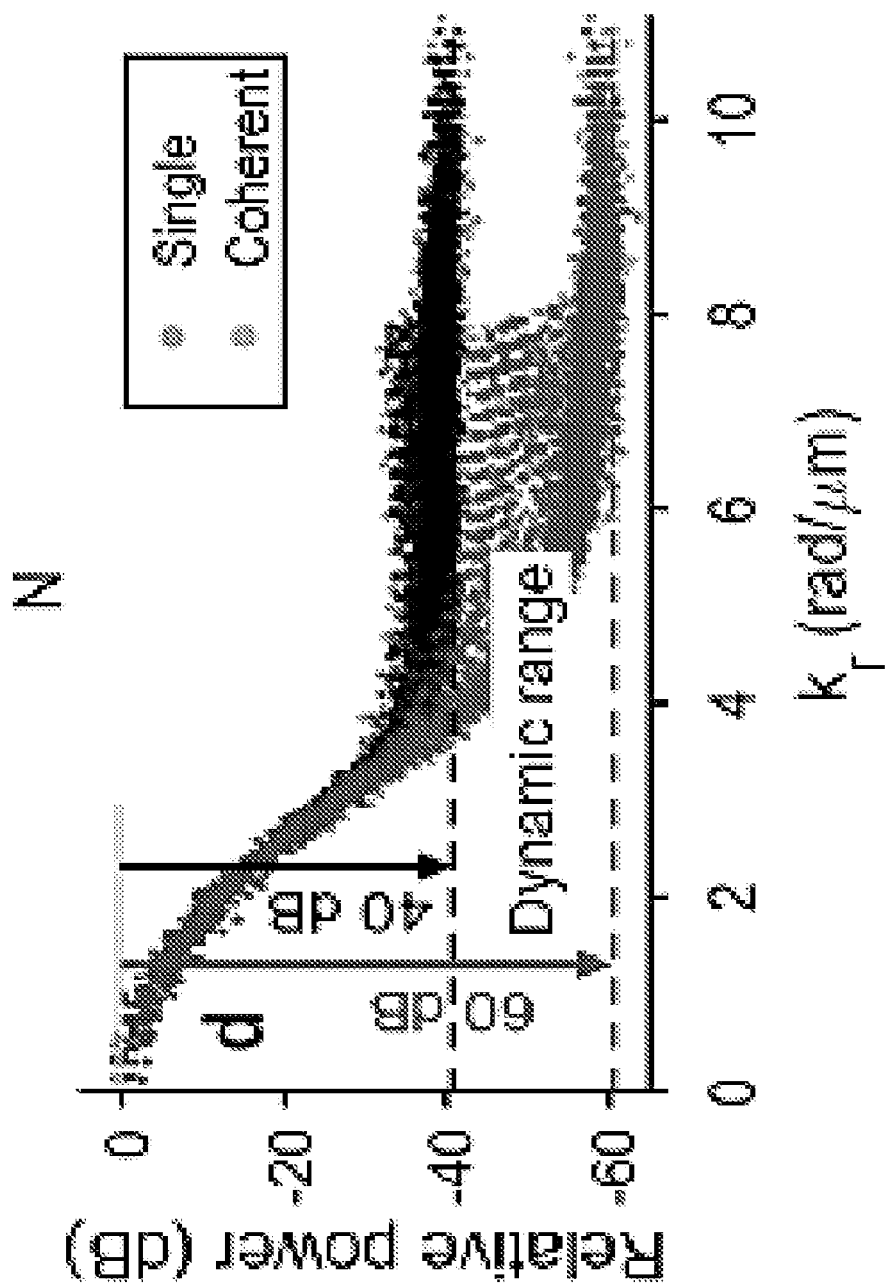
Figure 26E:
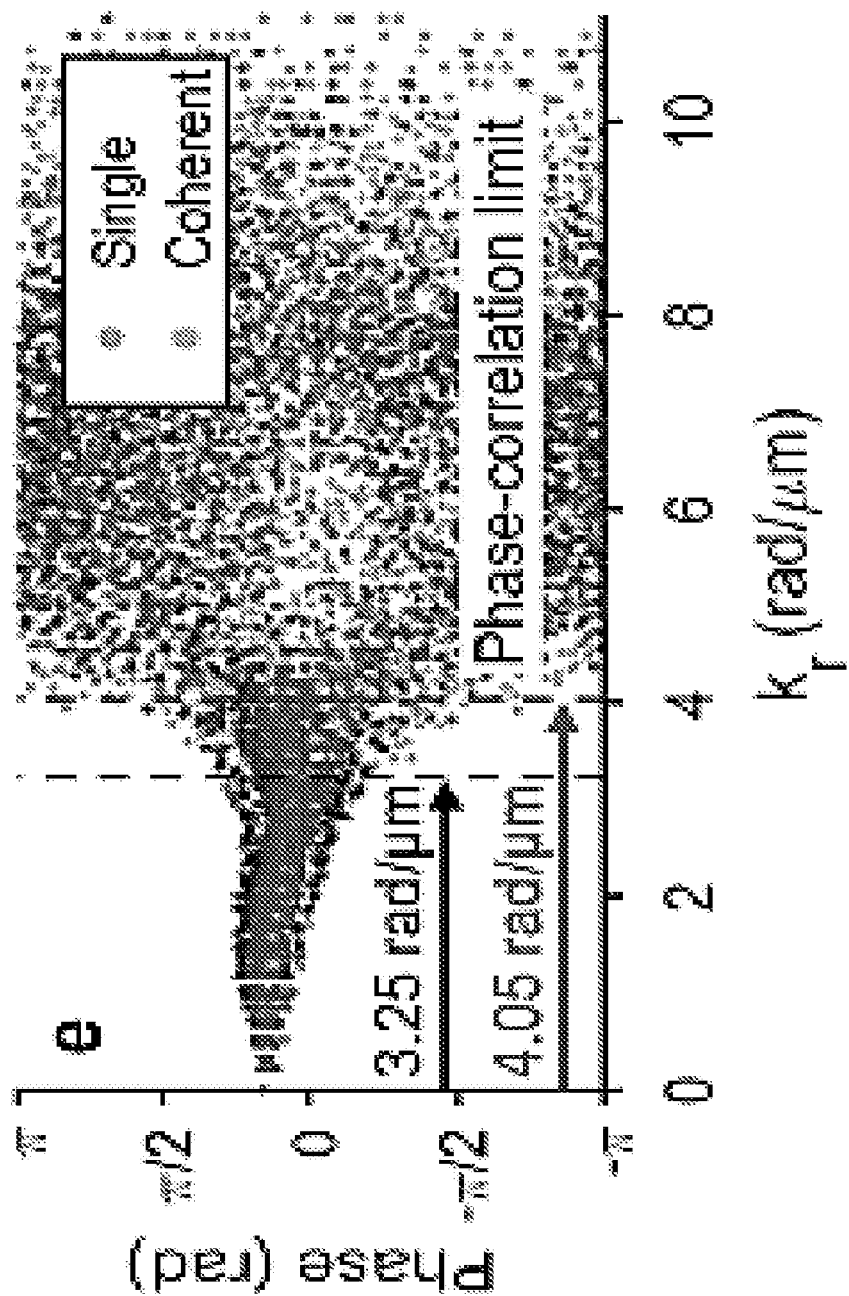

FIGS. 26A-26E show coherent-average noise suppression with 100 acquisitions in silicone phantom. FIG. 26A shows single-shot, incoherent- and coherent-average OCT images (same colormap range). En face images correspond to focal plane, indicated by arrow. Scale bar, 50 μm. FIG. 26B shows OCT intensity of scattering particles, silicone background, and noise as a function of N for incoherent (red) and coherent (blue) average. Noise intensity can be obtained from the "noise image" of an empty sample dish (see "Methods" section below), at the same pixel depth as the focal plane of the phantom images. FIG. 26C shows power and phase of single-shot and coherent-average images in transverse spatial-frequency domain (with spatial frequencies $k_x$ and $k_y$). Phase spectrum can be obtained from the Fourier transform of a windowed region around a single particle. FIG. 26D shows power spectrum in FIG. 26C plotted as a function of radial transverse spatial frequency kr. Dotted line indicates noise floor obtained from power spectrum of the noise image. FIG. 26E shows phase spectrum in FIG. 26C plotted as a function of kr. Dotted line indicates $k_r$ limit beyond which phase becomes decorrelated (local standard deviation>0.2 rad, see "Methods"). Section VII below discusses relations between N, DR and phase-correlation limit. Calculations of OCT intensity, DR, and phase-correlation limit are described in "Methods" section below.

Referring to FIGS. 26A-26E, noise suppression via coherent and incoherent average over N=1 through 100 acquisitions can be investigated in both space and spatial-frequency domain in a silicone phantom containing scattering particles. Factors that contributed to the measured noise include widely known sources of noise in OCT (i.e., shot noise, thermal noise, laser intensity noise), quantization noise, galvanometer jitter, mechanical vibrations in the optical system, sample motion, or any other sources of phase instability in the detected signal. Section III below discusses the effects on the image signal in the space domain, where a coherent average demonstrated a factor of N superior noise reduction efficiency over an incoherent average (FIGS. 26A-26B). Our results are consistent with previous work in OCT and theoretical trends (see Section III below for caveats of experimentally achieving the theoretical performance). Namely, noise intensity can be reduced by 20 dB (a factor of 100) after a coherent average over N=100 volumes (FIG. 2b, blue circle). Meanwhile, the silicone background intensity can only be reduced by 5 dB (FIG. 2b, blue asterisk), suggesting that the silicone medium generated systematic and phase-stable (i.e., not random) backscattered signal.

Some embodiments of the disclosed technology additionally show coherent-average noise suppression in the spatial-frequency domain (FIGS. 26C-26E), where the image is a superposition of the detected backscattered signal with a Gaussian magnitude spectrum (when imaged with a Gaussian beam) and the system noise with a uniform magnitude spectrum (circular Gaussian random variable in space). The power spectrum exhibited a dynamic range (DR) in the spatial-frequency domain, as measured from the power at DC to the noise floor (FIG. 26D). A coherent average over N=100 acquisitions resulted in a suppressed noise floor that led to an increase in DR of 20 dB, corresponding to noise reduction by a factor of 100 (FIG. 26D). In other words, the coherent average has revealed phase-stable but low-magnitude backscattered signal at higher spatial frequencies, which are originally below the noise floor in the single-shot image but are now above the suppressed noise floor. Consequently, signal phase remains correlated (i.e., absence of random phase variation) across spatial frequencies corresponding to a larger bandwidth (FIGS. 26C and 26E). The improved correlation of signal phase after reduction in the noise floor can also be understood by considering the impact of SNR on phase noise in phase-sensitive OCT. Section VII below discusses (in simulation) the relations between N, DR and phase-correlation limit in the spatial-frequency domain.

Resolution-Enhanced OCT in Silicone Phantom.

Figure 27A:
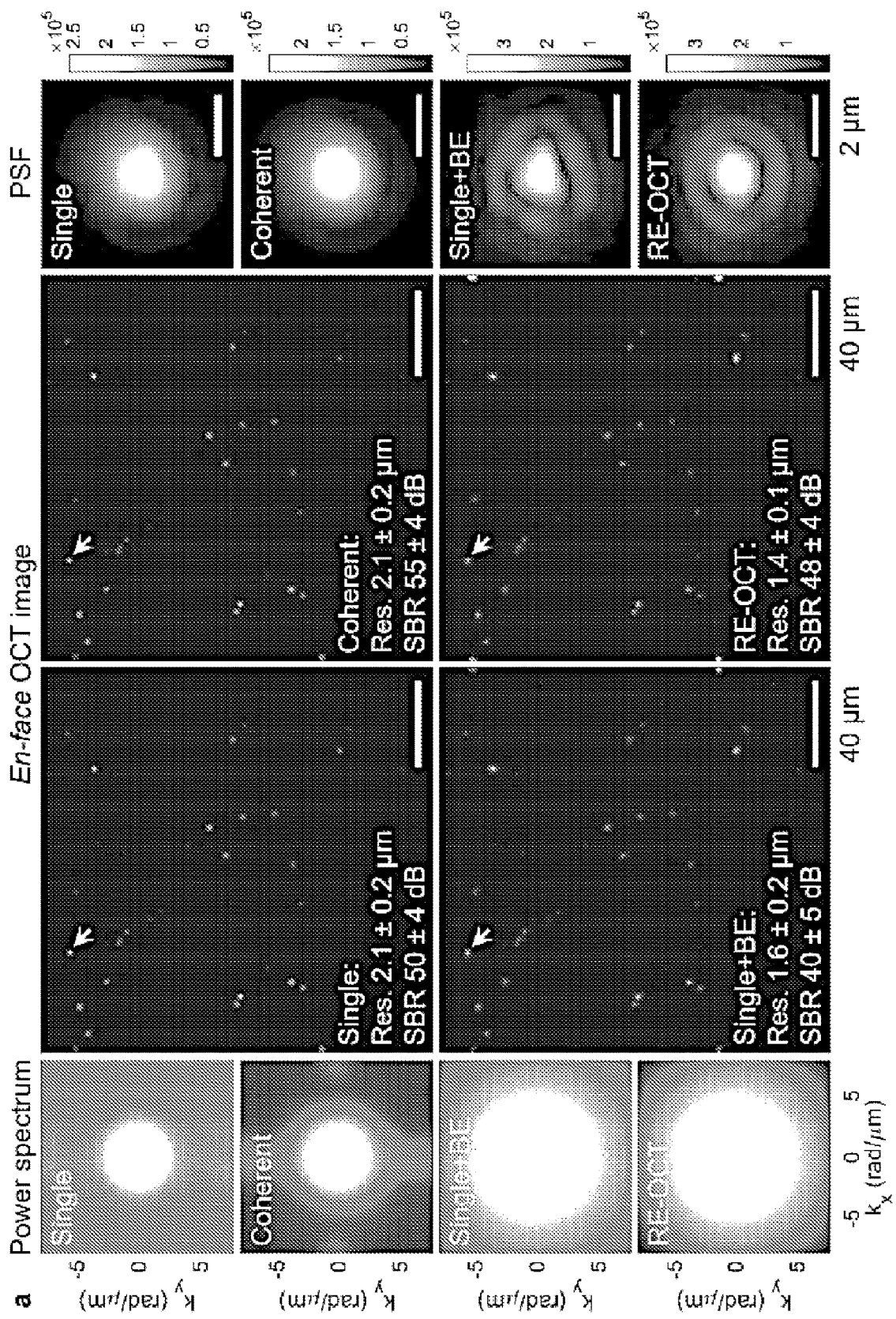
Figures 27B, 27C:
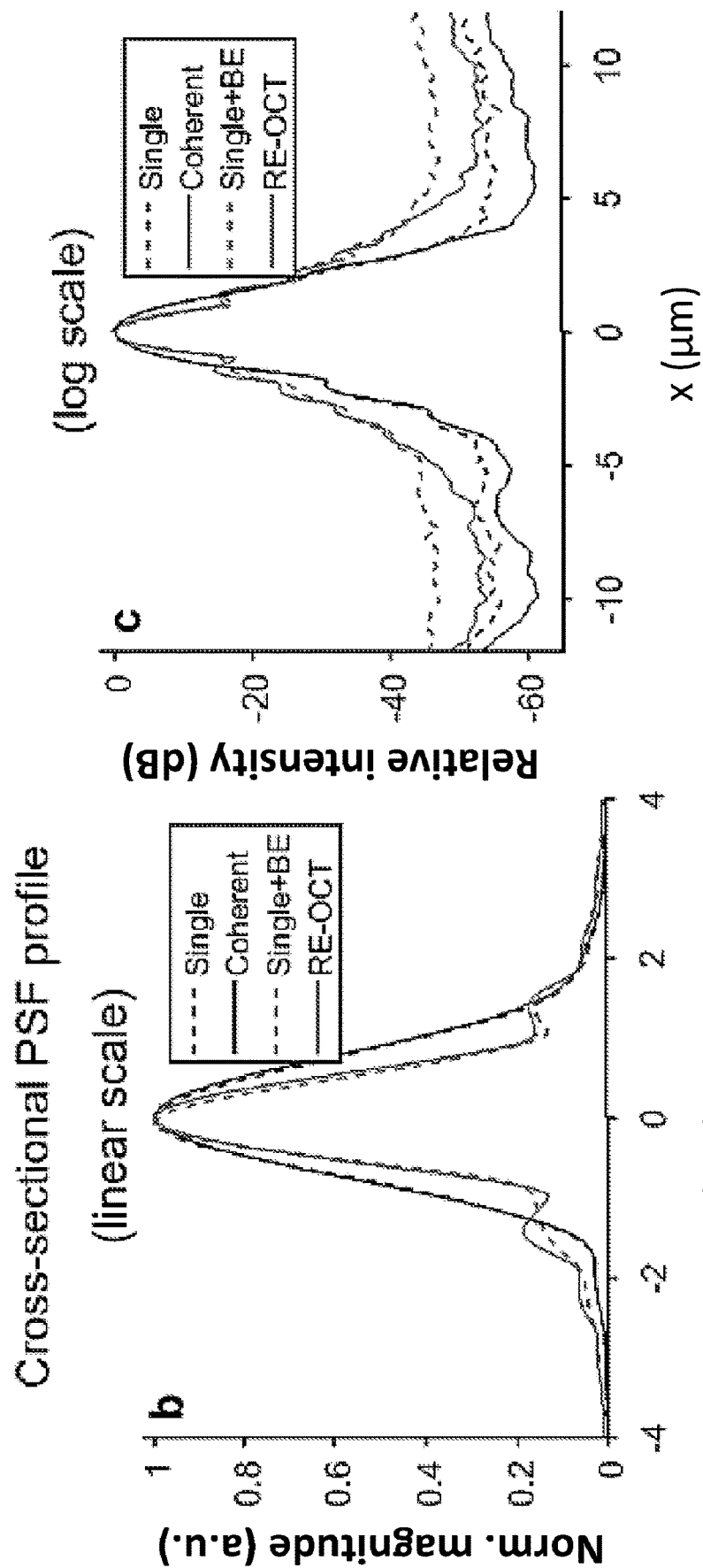

FIGS. 27A-27G show RE-OCT with 100 acquisitions and ×2.4 bandwidth expansion (BE) in silicone phantom. FIG. 27A shows single-shot, coherent-average, BE single-shot, and RE-OCT power spectrums (log scale) and space-domain en face OCT image with zoomed PSF (linear scale). Resolution and SBR represent mean±standard deviation of measurements from 11 particles. Scale bars, 40 µm (en face image) and 2 µm (zoomed PSF). FIGS. 27B-27C show cross-sectional profiles of zoomed PSF in FIG. 27A on peak-normalized linear and log scales. (d-f) Resolution, SBR, and RE-OCT efficiency as a function of BE factor from experiment and simulations for N=100 of noise-free (dotted), noise only (dashed), and noise with background (solid) conditions, with (red) and without (blue) optical aberrations. Grey vertical lines indicate the Nyquist limit based on spatial sampling of 0.4 µm/pixel. FIG. 27G shows resolution as a function of N from experiment and simulations for BE factor of 2.4. Resolution and SBR in FIG. 27A and data point and error bars for 'Experiment' in FIGS. 27D-27G represent mean standard deviation of measurements from 11 particles (see "Methods" section below). Bk background, Ab aberrations.

Resolution enhancement in silicone phantom using coherent average over 100 acquisitions and a computational BE expansion factor of 2.4× is shown in FIGS. 27A-27G. (see "Methods" section and Section IV for a complete description of the RE-OCT reconstruction procedure.) RE-OCT achieved a RE factor of 1.5×, from the traditional aberration-free resolution of 2.1 µm to an enhanced resolution of 1.4 µm (FIGS. 27A-27B), while the peak signal-to-background ratio (SBR) only marginally decreased from 50 to 48 dB (FIGS. 27A and 27C). (Note that difference in SBR between the single-shot and coherent-averaged images in FIGS. 27A-27G is not equivalent to the dB of noise suppression in FIGS. 26A-26E, see "Methods" section below for the calculation of SBR). In contrast, although the resolution also improved when computational BE can be performed directly on the single-shot image (FIG. 27B), not only is the SBR substantially decreased by 10 dB due to the increased noise floor (FIG. 27C), but the overall quality of the point spread function (PSF) is also degraded (FIG. 27A). This penalty is a result of computational BE indiscriminately amplifying both the backscattered signal and the system noise that dominates at higher spatial frequencies (FIGS. 26D and 26E). Resolution improved at the cost of degraded SBR as a larger BE factor is applied (FIGS. 27D-27E). Noise suppression prior to computational BE is essential in maintaining adequate SBR as well as the quality of the PSF in RE-OCT. However, even with a coherent average over 100 acquisitions, the best achievable resolution from this experiment is limited to 1.4 µm at BE factor of 2.4; applying a larger BE factor only resulted in lower SBR and degraded PSF quality, without further improvement in resolution.

In order to investigate the factors that limit the experimentally achievable resolution enhancement, the RE-OCT procedure can be performed on 6 simulated en face planes (3 conditions, each with and without aberrations) with properties representative of the silicone phantom images (FIGS. 27D-27G) (see Section VI for information on the simulated en face planes). Based on Cox and Sheppard's information capacity framework, the achieved RE factor is expected to be equivalent to the applied BE factor (see Section VIII). This relationship holds true for the simulated ideal noise-free condition, in which the RE-OCT efficiency (defined as the ratio RE factor/BE factor) remained 1 up to the Nyquist limit (FIG. 27F, noise-free limit). However, the presence of system noise decreased the RE-OCT efficiency with increasing BE factor (FIG. 27F, noise only). The trends as a function of BE factor for resolution, SBR, and RE-OCT efficiency for the noise-only condition are remarkably consistent with the experimental results (FIGS. 27D-27F). Furthermore, the presence of scattering signal from the silicone background, in addition to system noise, caused a slight decrease in RE-OCT efficiency relative to the noise-only condition (FIG. 27F, noise with background). These results suggest that system noise is the primary limiting factor in RE-OCT. Indeed, both experiment and simulation showed that superior resolution can be achieved with coherent average over larger N (i.e., more noise suppression) for a BE factor of 2.4 (FIG. 27G).

In addition, optical aberrations degraded resolution, SBR, and RE-OCT efficiency for all simulated conditions (FIGS. 27D-27G, red). As expected, the simulated condition incorporating all three contributions: system noise, silicone background, and aberrations, most closely matched the experiment.

Resolution-Enhanced OCT in Biological Samples

Figure 28A:
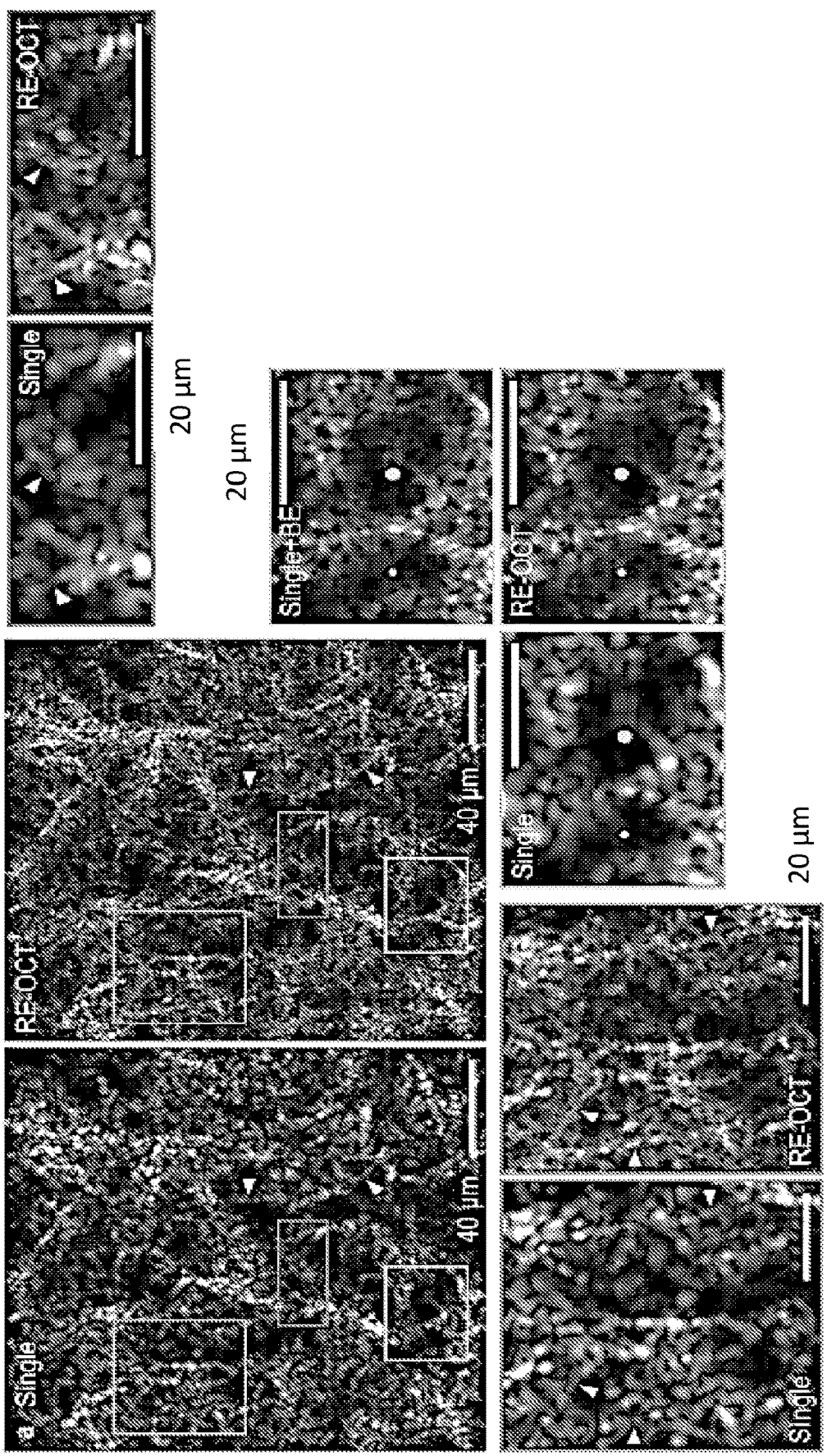
FIGS. 28A-28C shows RE-OCT with 100 acquisitions and ×2.0 BE in fibrous collagen gel.
Figures 28B, 28C:
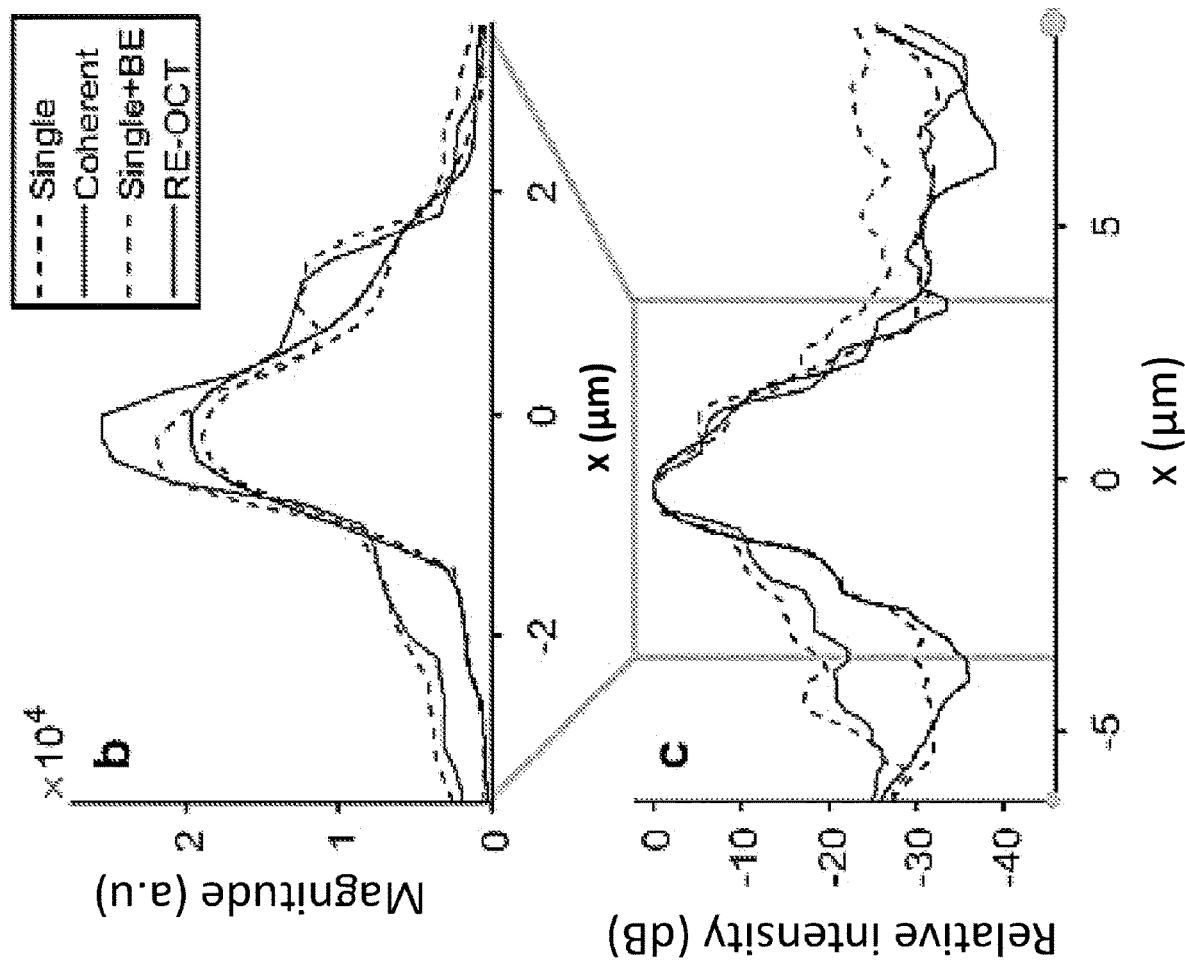

FIGS. 28A-28C shows RE-OCT with 100 acquisitions and ×2.0 BE in fibrous collagen gel. FIG. 28A shows single-shot and RE-OCT en face OCT images with zoomed insets regions indicated by boxes. Yellow arrows indicate fine fiber structures that can be more clearly visualized with RE-OCT. Scale bars, 40 µm (full) and 20 µm (zoomed). FIGS. 28B-28C show cross-sectional profiles of a line connecting from small to larger green dots in the green zoomed insets in (a) on linear and peak-normalized log scales.

Figure 29A:
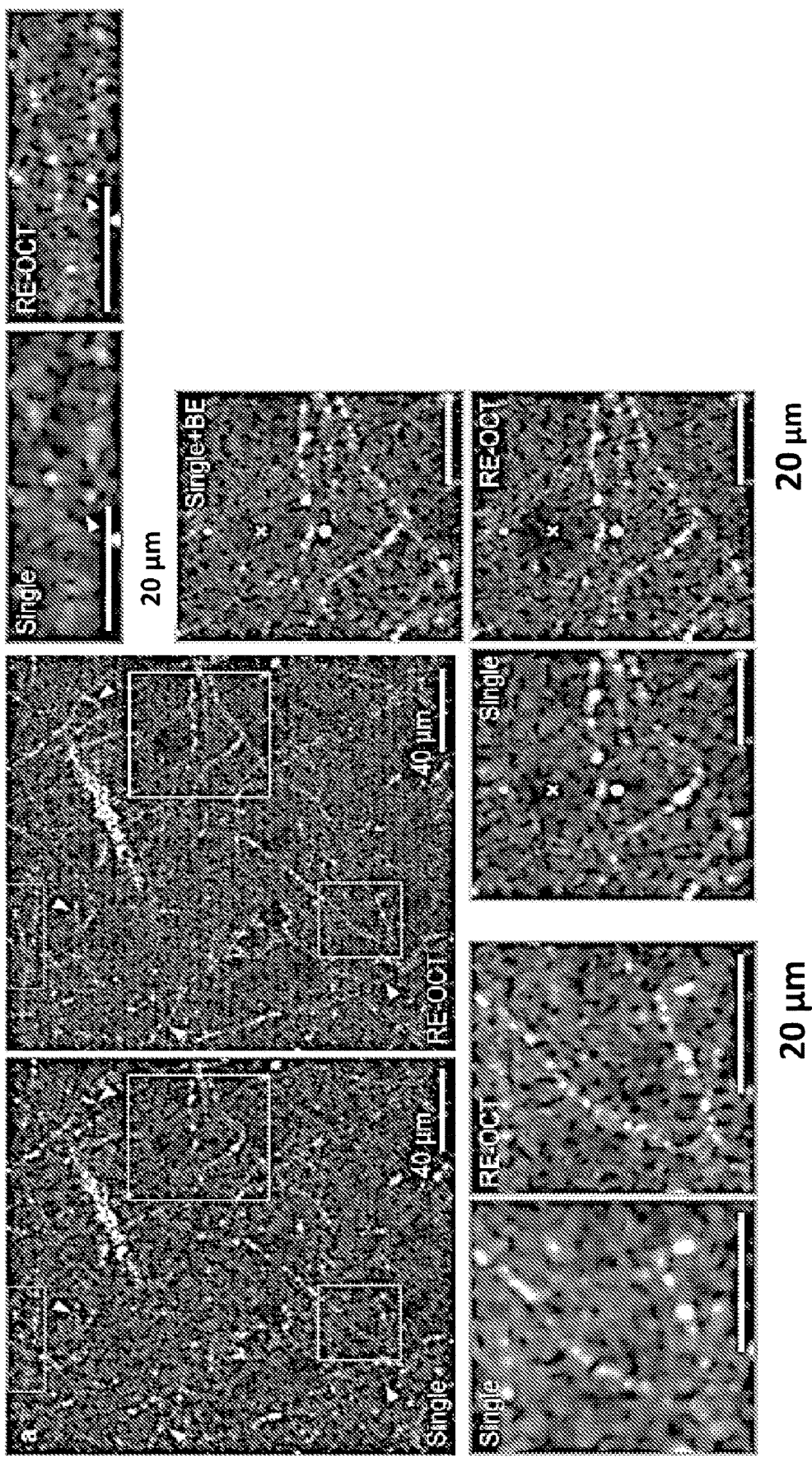
FIGS. 29A-29C show RE-OCT with 100 acquisitions and ×2.0 BE in the cortex of ex vivo mouse brain.
Figures 29B, 29C:
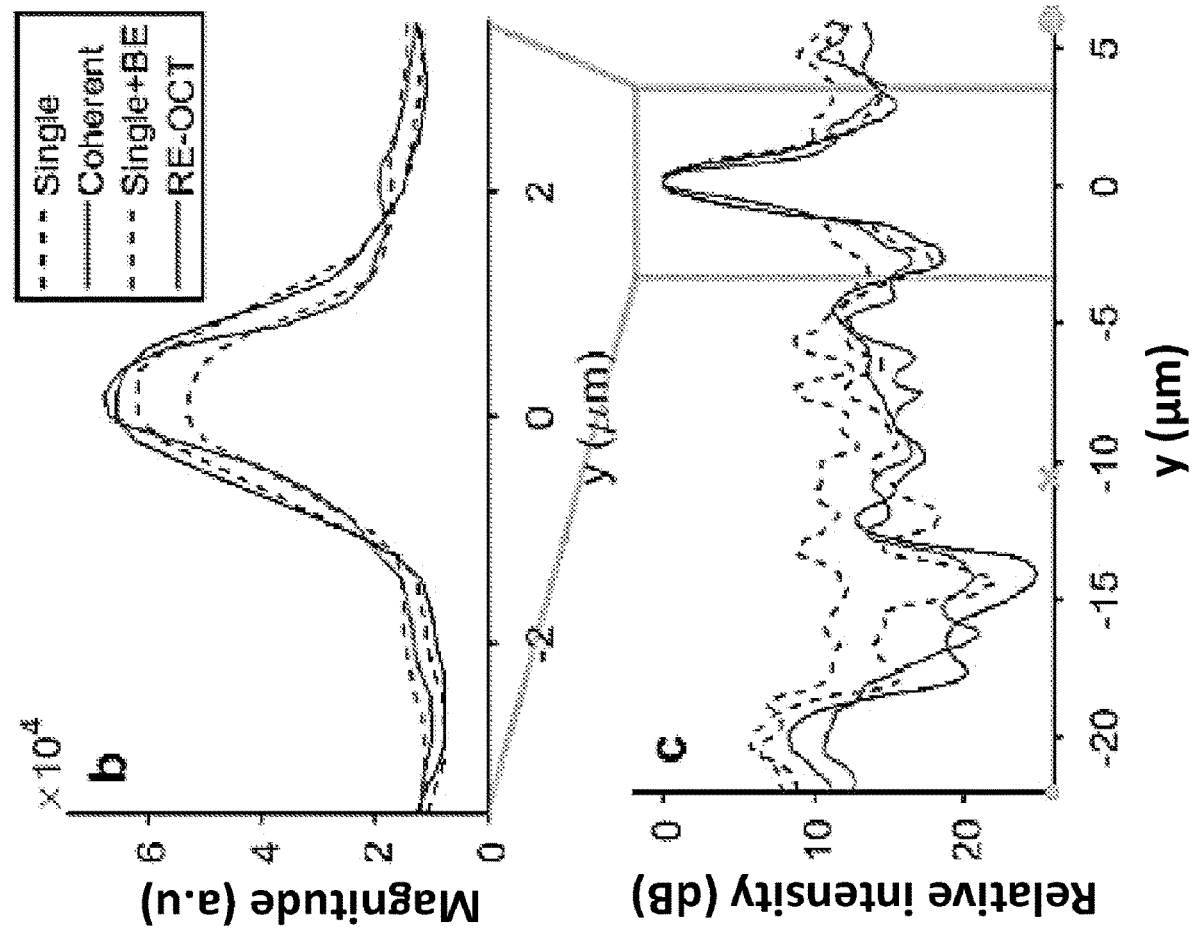

FIGS. 29A-29C show RE-OCT with 100 acquisitions and ×2.0 BE in the cortex of ex vivo mouse brain. FIG. 29A shows single-shot and RE-OCT en face OCT images with zoomed insets regions indicated by boxes. Images are taken in the first cortical layer at approximately 100 µm below surface. Yellow arrows indicate myelinated axonal processes that can be more clearly visualized with RE-OCT. × markers in the green zoomed insets indicate one of the neurons, which appear as darker circles due to weak OCT scattering. Green inset shows that neuron in BE single-shot image is barely discernible due to the SNR penalty without coherent-average noise suppression. Scale bars, 40 µm (full) and 20 µm (zoomed). FIGS. 29B-29C show cross-sectional profiles of a line connecting from small to large green dots in the green zoomed insets in FIG. 29A on linear and peak-normalized log scales. The green x marker indicates its corresponding position on the image.

RE-OCT can be implemented in collagen gel and ex vivo mouse brain, and show the best RE-OCT performances that are achieved, corresponding to BE factor of 2.0 (FIGS. 28A-28C and FIGS. 29A-29C). In fibrous collagen gel, RE-OCT enhanced the visualization of the collagen fiber architecture by not only narrowing the width of the collagen fibers, but also increasing the peak signal magnitude of each fiber as a result of the resolution enhancement FIGS. 28A-28B). Remarkably, low-contrast fine microstructural features, which are not clearly discernible in the traditional single-shot image due to weak signal, are more apparent in the RE-OCT image owing to the improved localization of signal energy in space (FIG. 28A, yellow arrows). In the BE single-shot image, the narrowing of fiber width can still be observed to a certain extent, but the peak signal magnitude did not improve as much (FIG. 28B). Furthermore, the SBR is degraded more severely in the BE single-shot image due to the amplification of noise without prior noise suppression (FIG. 28C). Computational BE with BE factors larger than 2.0 resulted in degraded SBR without further narrowing of the fiber width (visually assessed) or improvement to the peak signal magnitude (FIG. 28B), similar to the degradation observed with BE factors larger than 2.4 in the silicone phantom.

In ex vivo fresh mouse brain, RE-OCT enhanced the visualization of myelinated axonal processes, especially the low-contrast features that are less apparent in the traditional single-shot image (FIG. 29A, yellow arrows). Although the narrowing of fiber width could be observed in the BE single-shot image, the peak signal magnitude is degraded without coherent-average noise suppression (FIG. 29B), similar to the effects in collagen gel. Due to the typical fiber thickness of 1-3 m (which is comparable to the native OCT transverse resolution of 2.1 µm) of myelinated axons, some of the fiber narrowing observed here is not as prominent as in the collagen gel. The SNR penalty of the computational BE procedure is most apparent in the neuron (FIG. 29A, green inset), which produces lower OCT intensity than the surrounding brain tissue. Although the neuron remained visible in the RE-OCT image, the noise level in the BE single-shot image is brought up to that of the backscattered signal from the surrounding brain tissue, causing the neuron to 'disappear' into the background (FIGS. 29A and 29C). This emphasizes the importance of coherent averaging in RE-OCT, particularly when weak-scattering structures need to be clearly visualized. Computational BE with BE factors larger than 2.0 resulted in degraded SBR and lower contrast between the neurons and surrounding brain tissue, without further narrowing of the fiber width (visually assessed) or improvement to the peak signal magnitude.

Factors that Limit Achievable Resolution Enhancement

Figure 37:
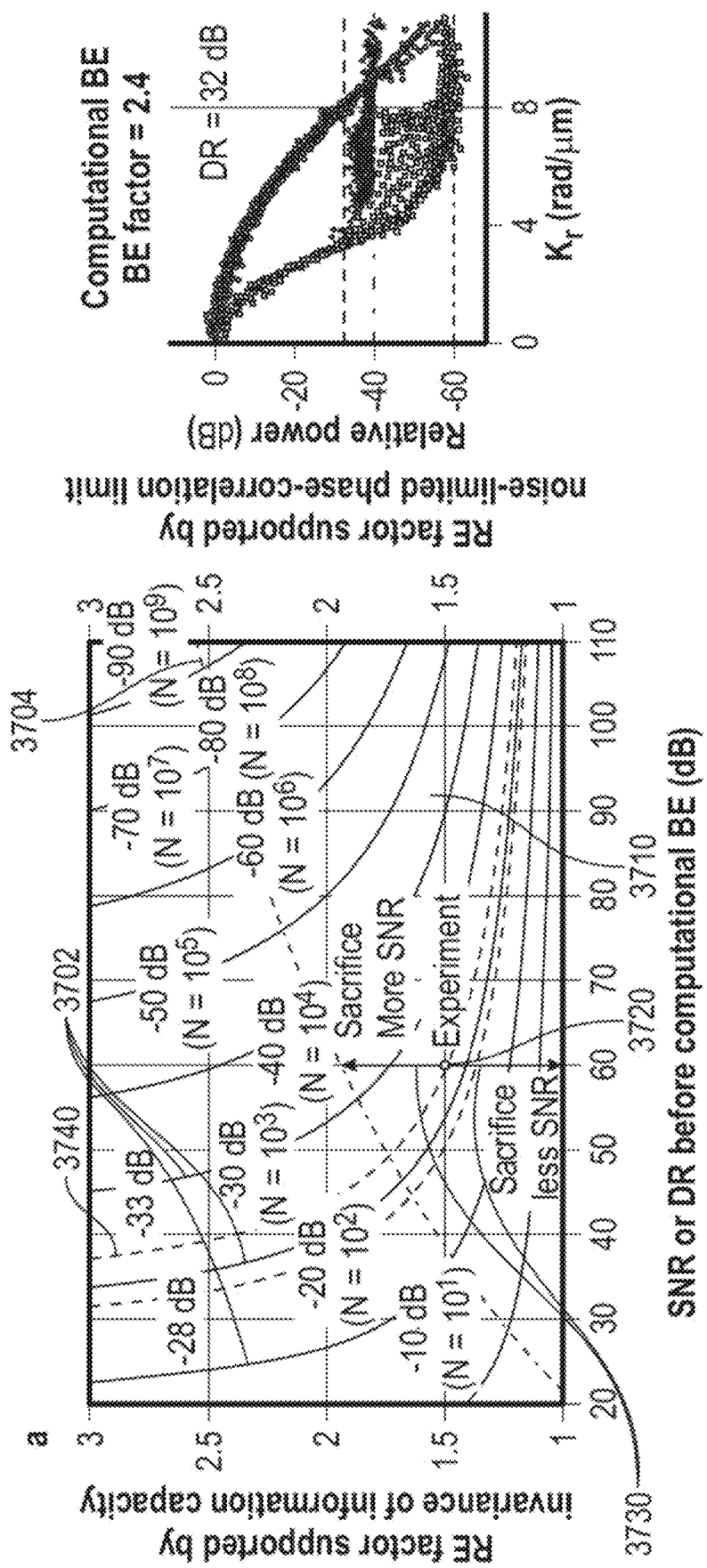
FIG. 37 shows fundamental limits to resolution enhancement in RE-OCT.

The image signal power and phase in the spatial-frequency domain (FIGS. 26C-26E) discussed in this patent document can be used to further understand the role of system noise, background, and optical aberrations on RE-OCT resolution. In the spatial-frequency domain, an increase in system noise will 'bury' the signal at higher spatial frequencies first, leading to a reduced DR and an effective reduction in the supported spatial-frequency bandwidth (FIG. 26D); this corresponds to an optimal PSF that is broader in the space domain. More fundamentally, this phenomenon can be explained from the perspective of phase correlation. System noise not only limits the available DR of the spatial-frequency-domain image, but—as a consequence of SNR-limited phase noise—also limits the spatial-frequency bandwidth over which signal phase (associated with any given point scatterer in space) remains correlated (FIGS. 26E and 26E and FIG. 37). Phase correlation in the spatial-frequency domain has a direct implication on the spatial resolution of a coherent image—in order to achieve the best localization of signal energy in space, signal at different spatial frequencies must be able to constructively interfere (i.e., be in-phase with each other). Thus, the phase-correlation limit (which is limited by SNR in our experiment) determines how much of the expanded spatial-frequency bandwidth (determined by the BE factor) can support constructive interference and contribute to enhancing the resolution in RE-OCT. Computational BE far beyond the phase-correlation limit only serves to amplify the contribution of phase-decorrelated higher spatial frequencies, which degrades the SBR and the quality of the PSF without further improving the resolution (FIGS. 27D-27F). In this regard, phase correlation in the spatial-frequency domain represents a more fundament (and general) limit to spatial resolution in coherent imaging, where SNR is but one—a predominant one in this case-factor that can disrupt phase correlation.

In contrast to system noise, background is composed of backscattered [single-(SS) and multiple-scattering (MS)]

signal from the sample medium (silicone in this case). The spatial-frequency spectrum of the SS background is bandlimited and obeys the imaging bandwidth support of the system (determined by the illumination beam width in our system). Meanwhile, evidence has shown that frequency content of MS background may extend beyond the imaging bandwidth of the system. (However, this work is different from beam-scanned OCT because it performed incoherent imaging using full-field detection.) In either case, background may exhibit uncorrelated phase as opposed to a flat profile of an ideal PSF (FIG. 36(b)) and contribute to the disruption of phase correlation within (SS case) as well as outside (MS case) of the imaging bandwidth. As a result, resolution may be degraded by the presence of background compared to if the medium is completely transparent. In this respect, the role of background on OCT resolution is similar to that of optical aberrations—while aberrations contribute slowly varying phase inside the pupil, background contributes uncorrelated phase that results in the OCT speckle. Importantly, both effects imply that the sample itself may limit the achievable resolution; there can be contribution from sample-induced aberrations in addition to system aberrations, and the degradation of resolution by uncorrelated background phase becomes more severe when the structure of interest has lower SBR (e.g., due to weak scattering from the structure or strong scattering from the medium, or both). Furthermore, both background and aberrations are factors that cannot be mitigated by coherent-average noise suppression.

Beyond system noise, background, and optical aberrations, RE-OCT is also ultimately limited by the spatial-frequency bandwidth support of the optical components (e.g., objective lens), which define the physical aperture outside of which SNR is exactly zero. Computational BE is only effective over the spatial frequencies at which the coherent-averaged spectrum (i.e., the optical transfer function) has finite values above the suppressed noise floor (which is defined by the phase-correlation limit). In the presented experiments, where the spectrum is a smooth function that under-fills the objective aperture, this limit is imposed by the system noise, which allows RE-OCT to harness additional spatial frequencies via coherent-average noise suppression. However, if the spectrum is to be truncated by the objective aperture (i.e., an aperture-filled system), this limit would be strictly imposed by the physical aperture with no room for further computational BE. That is, RE-OCT can only 'boost' the signal that is originally present (i.e., non-zero SNR), but not 'create' new signal that did not exist. Retrieving the spatial frequencies beyond the physical aperture of the optical system is beyond the scope of RE-OCT; this would require analytic continuation and could potentially be achieved by some super-resolution and/or deep learning approaches.

Expanded framework of information capacity and resolution in coherent imaging. A fundamental limit to resolution enhancement by RE-OCT is governed by the disruption of phase correlation in the spatial-frequency domain-due to system noise, background, aberrations, and other factors (e.g., sample instability, mechanical vibration, etc.). Among other factors, system noise played the most significant role in our experiments by determining the available DR of the image and the phase-correlation limit in the spatial-frequency domain. Notably, system noise is also the only factor that can be suppressed via coherent averaging in our experiments. Thus, the basis of RE-OCT lies in navigating the trade-off between resolution (in the space domain) and DR (in the spatial-frequency domain) of the image via coherent-average noise suppression and computational BE (FIG. 25A), where DR represents the impact on SNR that manifests in the spatial-frequency domain (FIG. 26D). In FIGS. 27A-27C, resolution enhancement is prioritized and a BE factor of 2.4 is applied, sacrificing more DR than the 20 dB earned with coherent averaging (FIG. 38(b)). Alternatively, a BE factor of only 1.4 can be applied to simultaneously improve both resolution and SBR by a smaller margin (FIGS. 27D and 27E), where the SNR penalty is offset by the increased peak PSF intensity as a by-product of improved localization of the PSF in space (note the maxima in FIG. 27E). The optimal choice of the BE factor is very much dependent on the type of samples and the information that needs to be enhanced for a particular application. Image metrics for the selection of the optimal BE factor could be customized for each specific application.

Referring back to FIG. 23 showing expanded framework of information capacity and resolution in coherent imaging, factors that influence elements of the expanded information capacity and ultimately affect resolution in coherent imaging. Phase correlation in the spatial-frequency domain is an important addition to the existing framework of information capacity (green dotted box). Red arrows denote factors that can disrupt phase correlation in the spatial-frequency domain. Green arrows indicate the role of RE-OCT: enhancing DR in the spatial frequency domain via coherent-average noise suppression, then, expanding imaging bandwidth via computation BE. For the sake of simplicity, the depicted framework omits the temporal components and only considers information in the spatial dimensions. Section VII below discusses the relationship between system and imaging bandwidths, illumination NA, and FOV. BW, bandwidth.

In order to reconcile the predictions of information capacity and our experimental RE-OCT results, the disclosed technology can be implemented in some embodiments to provide an expanded framework of information capacity and resolution in coherent imaging (FIG. 23). The expanded framework emphasizes phase correlation in the spatial-frequency domain (in addition to SNR, FOV and spatial-frequency bandwidth in Cox and Sheppard's framework) as an important facet of the information capacity of a coherent imaging system. In theory, resolution is governed by the imaging bandwidth of the optical system. In practice, however, phase-correlation limit in the spatial-frequency domain (FIG. 26E and FIG. 36) must also be considered when determining the best achievable resolution. Supplementary Section VIII computes the resolution enhancement that is theoretically supported by Cox and Sheppard's information capacity framework, and exemplifies the additional practical limit imposed by the SNR-limited phase-correlation limit (FIG. 36(a)). Importantly, any factors-whether associated with the optical system or the sample itself—that can disrupt phase correlation in the spatial-frequency domain may prevent the optimal resolution (determined by the bandwidth support of the optical system) from being experimentally realized. The theorem of invariance of information capacity (Eq. 5) may, in principle, be restated in term of phase correlation rather than SNR, however, this theoretical advance is beyond the scope of this paper. B$_y$ extension, in a time-dependent system whose information capacity includes the time-bandwidth product, the temporal resolution of such a system would also be subjected to the correlation of phase in the temporal-frequency domain.

Beam-scanning is by far the most common mode of acquisition in OCT. Most beam-scanned OCT systems utilize a Gaussian illumination beam that under-fills the physical aperture limit (e.g., objective lens) in the optical system.

This under-filling is required for the widely used telecentric scanning scheme (as opposed to pivoting at the objective aperture), which is implemented to minimize distortions due to coherence gate curvature. (Although ophthalmic OCT systems do not implement telecentric scanning, the typical beam diameter of 1.2 mm in standard clinical systems still under-fills the physical aperture of typical pupil diameters of adult eyes). RE-OCT exploits this ubiquitous design feature in OCT systems to enable resolution enhancement beyond the aberration-free limit achieved by existing aberration correction approaches. In beam-scanned OCT, the aberration-free resolution limit is determined by a combination of the illumination beam width and the objective lens (i.e., the smaller of the Gaussian beam NA or the objective lens NA, see Supplementary Section II); for a telecentric-scanning OCT, the Gaussian beam NA is typically much smaller. Higher resolution is traditionally achieved by increasing the beam width or simply switching to a higher-NA objective (a standard practice in optical microscopy). RE-OCT, on the other hand, offers the flexibility to enhance transverse resolution beyond the aberration-free limit, using a simple computational procedure, without requiring any modification to the optical system or specialized acquisition schemes in existing aperture synthesis techniques. This gives RE-OCT a remarkable potential to have a widespread impact as it can be readily implemented on most OCT systems in the world and immediately unlock information that is beyond the current imaging capability of the system.

Phase stability is vital for achieving optimal performance in RE-OCT, as is the case in other phase-sensitive techniques in coherent imaging such as CAO and OCT angiography, which poses potential challenges for biological (e.g., live-cell imaging) and clinical (e.g., in vivo imaging) applications. In the case of RE-OCT, efficient earning of SNR via coherent-average noise suppression is contingent upon the backscattered signal from multiple acquisitions being phase-registered to each other. Our experiments in ex vivo fresh mouse brain (FIGS. 29A-29C) required an additional image registration procedure (Supplementary Section V) to achieve phase registration before computing the coherent average. Others in OCT have also developed image registration and phase correction methods that successfully enabled phase-sensitive processing in biological samples, including for in vivo settings. Furthermore, advances in high-speed imaging have enabled OCT imaging at MHz-rate, combatting motion artefacts and supporting phase-sensitive imaging in vivo. RE-OCT may be particularly attractive for high-speed systems, some of which already incorporate coherent or incoherent averaging, where the RE-OCT procedure can be easily integrated into the existing imaging workflow with minimal additional effort and imaging time. Thus, RE-OCT can draw from existing and emerging solutions in the field to address the challenges associated with achieving the required phase stability for biological and clinical applications, including in vivo imaging.

Beyond the potential applicability of RE-OCT for OCT systems worldwide, the concept that noise suppression (improved SNR) can be harnessed for resolution enhancement—where efficient noise suppression is key to 'purchasing' greater resolution enhancement—has broad implications for not only OCT but also optical microscopy and imaging science. Traditionally, averaging and noise suppression have been associated with the improvement of image contrast or SBR in optical microscopy. However, the theorem of invariance of information capacity suggests that there are opportunities to exploit the information gained via noise suppression in other facets of optical imaging. RE-OCT applies this concept to improve resolution through an exchange of information between spatial-frequency bandwidth and SNR.

Furthermore, the expanded framework of information capacity and resolution in coherent imaging presented here is broadly relevant and contributes to the theory governing coherent image formation. This includes coherent imaging with an aperture-filled system (e.g., full-field OCT) even though RE-OCT is only applicable when the physical aperture is under-filled. For instance, an image of a sample that generates particularly weak signal may have a very limited DR in the spatial-frequency domain, such that the SNR-limited phase-correlation limit is smaller than the imaging bandwidth of the optical system. Resolution would be limited by the available DR as opposed to the illumination NA (in an under-filled system) or the objective NA (in an aperture-filled system) in such a low-SNR scenario. Alternatively, the detected backscattered signal may be well above the noise floor, but both the object and the surrounding medium contribute comparable signal strength such that the DR spanned by the SS signal level in the sample is low. The disruption of phase correlation by the SS and MS background could limit the ability to resolve the object in such a low-DR scenario. B$_y$ extension, physically increasing the image bandwidth of an optical system (e.g., by using a higher-NA objective or increasing the illumination beam width) would yield the optimal improvement in resolution only if the acquired image had sufficient DR in the spatial-frequency domain to support phase correlation over the increased bandwidth. Thus, our expanded framework highlights important practical considerations (associated with both the optical system and the sample/object) for resolution in all forms of coherent imaging.

Future development may combine RE-OCT with aberration-diverse OCT in order to suppress both the system noise and the MS background. Additionally, RE-OCT may be advantageous for imaging transversely isotropic structures (i.e., spatially invariant along a given spatial dimension) such as aligned muscle fibers or organized collagen fibrils in tendon and cartilage. This could allow for bandwidth along both the temporal and the invariant spatial dimension to be sacrificed to further enhance the resolution along the orthogonal spatial dimension. Furthermore, the same RE-OCT approach can be applied to enhance the axial resolution of an SD-OCT system by 'boosting' the tails of the source spectrum within the spectrometer bandwidth, provided that the broadband light source 'under-fills' the spectrometer.

RE-OCT is an approach that offers the flexibility to enhance resolution in beam-scanned OCT beyond the aberration-free resolution limit of the optical system. RE-OCT can be readily implemented on most OCT systems in the world without requiring any modification to the optical system. Based on the theorem of invariance of information capacity, RE-OCT navigates the information exchange between resolution and SNR by 'earning' SNR via coherent-average noise suppression, in order to 'purchase' superior resolution via computational BE. Coherent averaging increases DR in the transverse spatial-frequency domain, and for the first time, has been harnessed for resolution enhancement in OCT. In silicone phantom, RE-OCT achieved a resolution improvement of 1.5× (NA increase of 0.2 to 0.3), while maintaining comparable SBR to the traditional single-shot image. In collagen gel and ex vivo mouse brain, RE-OCT significantly enhanced the visualization of fine microstructural features, including low-contrast features that are otherwise obscured in the traditional OCT image. The phase-correlation limit represents an additional practical limit to the effective spatial-frequency bandwidth support of a coherent imaging system that can be more restrictive that the theoretical limit imposed by the existing theory of information capacity. Based upon these insights, the disclosed technology can be implemented in some embodiments to provide an expanded framework of information capacity and resolution in coherent imaging to incorporate these factors. This framework emphasizes the fundamental role of phase correlation, which contributes important implications to the theory of coherent imaging.

Methods

Optical system. The optical system can be a standard telecentric beam-scanned spectral-domain (SD)-OCT system (FIG. 31(a)). The SD-OCT system is sourced by a broadband superluminescent diode (SLD) with a central wavelength of 850 nm and a bandwidth of 120 nm. The light from the SLD is split into an optical sampling beam and an optical reference beam by an optical coupler implemented by a fiber coupler (FC). The optical reference beam is directed to a mirror in the optical reference arm to return back to the fiber coupler (FC). Spectral data is detected by detecting a portion of the returned reference beam by a spectrometer with a bandwidth of 180 nm and a 2048-pixel line-scan camera. The sample arm for illuminating a sample for OCT imaging includes a double-pass illumination/collection configuration with an inverted 20× microscope objective with an NA of 0.45. Telecentric beam-scanning can be accomplished with a 2-axis galvanometer and a zero-magnification telescope, which imaged the galvanometer to the back focal plane of the objective. Th objective lens collects light from the illuminated sample so that the collected sample light is directed backwards in the optical reference arm back to the fiber coupler (FC) to spatially overlap with the returned reference beam for OCT imaging. The illumination beam diameter can be about 2-3 mm, which under-filled the objective back aperture diameter of 8.1 mm. The native transverse resolution can be 2.1 µm at the focal plane and the axial resolution can be 1.9 µm in air. The system sensitivity can be about 90 dB at the implemented acquisition rate (see RE-OCT image acquisition procedure) with a fall-off of—5 dB/mm. The system can be controlled by a custom-built acquisition software.

Sample preparation. All samples are prepared in glass coverslip-bottomed petri dishes, where the OCT beam interrogated the sample from the bottom through the coverslip (FIG. 31(c)). The "noise image" for measuring the system noise in FIGS. 26B and 26D can be acquired by imaging the empty sample dish (FIG. 31(c)).

Silicone phantom (FIGS. 25A-25B and 26A-26E) can be prepared with a mixture of polydimethylsiloxane (PDMS) fluid and 2-part RTV silicone at a weight ratio of 100:10:1 PDMS to RTV A to RTV B. Titanium dioxide particles with diameter of 0.5 µm are dispersed as scattering particles. Silicone mixture can be baked at 70° C. for at least 8 h to complete the polymerization process. The sample can be stored room temperature, where the temperature is allowed to stabilize, prior to imaging.

Collagen gel (FIGS. 28A-28C) can be prepared with type I collagen at a final collagen concentration of 2.0 mg/mL. Collagen can be polymerized at 4° C. for 15 min., 20° C. for 15 min., and finally 37° C. for 15 min. to promote formation of heterogeneous fiber architecture with thick collagen fibers. The sample is removed from incubation 1-2 h before imaging to allow the temperature to stabilize at room temperature.

Ex vivo mouse brain (FIGS. 29A-29C) can be harvested post-mortem from a C57BL/6 mouse. Euthanasia is induced by an intraperitoneal injection of pentobarbital (150 µL of 39 mg/mL solution in saline) and then perfused via intracardiac puncture with 30-mL phosphate-buffered saline (PBS) at 4° C. The harvested brain can be stored in PBS at 4° C. before embedded in 1% agarose in the sample dish without fixation. The sample can be kept at room temperature for 1-2 h to allow the temperature to stabilize at room temperature before imaging. All animal procedures are approved by the Cornell Institutional Animal Care and Use Committee and are performed under the guidance of the Cornell Center for Animal Resources and Education.

RE-OCT image acquisition procedure. Images are acquired in CM mode, where 3D OCT volumes are acquired successively to allow sufficient decorrelation of noise (see Section III below). Each volume is acquired with a line scan rate of 70 kHz, an exposure time of 10 µs, and a transverse spatial sampling of 0.4 µm/pixel. In order to maximize the dynamic range spanned by the signal from the sample, image is acquired in the conjugated configuration by adjusting the reference arm such that the coverslip-bottom of the sample dish is positioned at larger pixel depths near the bottom of the B-scan (see Section II below).

RE-OCT image reconstruction procedure. RE-OCT image reconstruction from the acquired CM-mode volumes followed the procedure described in Section IV below. Briefly, space-domain OCT volumes are obtained from the raw tomograms via standard OCT image reconstruction, then, corrected for defocus via computational image formation procedures based on previously described methods. For ex vivo mouse brain, an additional image registration procedure is required to correct bulk sample shift and phase drift in order to ensure that backscattered signal is spatially- and phase-registered across CM-mode volumes, as described in Section V below. Then, coherent average across processed OCT volumes is computed and its magnitude spectrum is obtained from the 2D transverse Fourier transform. A BE mask is computed from the magnitude spectrum at a given BE factor and applied to the coherent-average OCT volume in the transverse spatial-frequency domain. Finally, the BE spectrum is zero-padded to upsample (in space) before returning to the space domain. The spatial upsampling is implemented to facilitate resolution measurement via curve-fitting to the PSF. All OCT images shown has undergone defocus correction and represent the traditional aberration-free imaging capability before computational BE.

Calculations of OCT intensity. The OCT intensity of the scattering particles, silicone background, and noise in FIG. 26B are computed as follows. Scattering particle intensity is obtained from the 99th percentile of the OCT scattering intensity (i.e., square of OCT magnitude) of the space-domain image at the focal plane. Silicone background intensity is obtained from the median of the OCT scattering intensity of the particle-removed space-domain image at the focal plane. The scattering particles are removed from the en face image via magnitude thresholding followed by a dilatation of the binary mask. Noise intensity is obtained from the standard deviation of the OCT scattering intensity of the "noise image" at the same pixel depth as the focal plane of the silicone phantom image. The "noise image" is obtained by imaging an empty blank sample dish (FIG. 32(c)), placing the coverslip at the same pixel depth as in the silicone phantom.

Calculation of dynamic range and phase-correlation limit. The dynamic range in FIG. 26D and FIG. 37 is computed as follows. First, the noise power spectrum is obtained from the square of the magnitude of the 2D transverse Fourier transform of the "noise image" at the same pixel depth as the focal plane of the silicone phantom image. Then, the relative noise power is computed with regard to the signal power at DC (i.e., $k_r=0$ rad/µm) of the silicone phantom image at the focal plane. DR value in decibels is obtained from the mean of the relative noise power spectrum (uniformly distributed) across the entire transverse spatial-frequency domain.

The phase-correlation limit in FIG. 26E and FIG. 37 is computed as follows. First, a window of size 243×243 pixels centered on a single scattering particle is cropped from the silicone phantom image at the focal plane. Then, the phase spectrum of the PSF is obtained from the angle of the 2D transverse Fourier transform of the window-out region. Next, local standard deviation of the phase spectrum is computed over a sliding kernel of size 3×3 pixels to obtain the "phase-decorrelation spectrum." The "phase-decorrelation spectrum" is divided into spatial-frequency bins, ranging from $k_r=0$ rad/µm to $k_r=7.85$ rad/µm (the Nyquist limit) at bin width of 0.1 rad/µm. Phase-correlation limit is obtained from the $k_r$ value at the center of the bin at which the mean of the "phase-decorrelation spectrum" exceeded 0.2 rad.

Measurements of resolution and SBR. Resolution and SBR values in FIGS. 27A, 27D-27F are obtained from the Gaussian curve-fit to the PSFs (i.e., scattering particles) located at the focal plane. First, maximum intensity projection across 3 pixel-depths about the focal plane is computed from the OCT magnitude image. Scattering particles at the focal plane with peak magnitude>5×10$^4$ are manually identified and the PSF images (a window of size 73×73 pixels centered on each particle) are cropped out. Then, a total of 32 radial cross-sectional profiles of the PSF images (i.e., 1D PSF profiles at 32 different angular cross sections) are extracted for linear least-square curve fitting to a 1D Gaussian function. The fit parameters from the 32 cross-sectional profiles are averaged to obtain the peak magnitude and full width at half-maximum (FWHM) of each particle. At this stage, particles with FWHM>2.4 µm measured from the coherent-average OCT volume (i.e., noise-suppressed but not bandwidth-expanded) are excluded for being either air bubbles or aggregates of multiple particles. A total of 11 particles remained after the exclusion.

Resolution is obtained directly from the mean FWHM of the 11 remaining particles. SBR is obtained from the mean "peak SBR" of the 11 particles. The "peak SBR" in decibels of each particle is computed from the ratio of the peak PSF intensity (square of peak magnitude from the Gaussian fits described above) to the silicone background intensity (computed as described in Calculations of OCT intensity).

Section I: Information Capacity and Resolution Enhancement Via Exchange of Information Cox and Sheppard derived an expression for the information capacity (in bits) of an optical system (Eq. 5), which is restated here:

$$C=(2L_xB_x+1)(2L_yB_y+1)(2L_zB_z+1)(2TB_T+1)\log_2(1+s/n) \quad (\text{Eq. S1})$$

where L, T, and B denote the spatial field-of-view (FOV), temporal duration, and bandwidth in the associated dimension, respectively. The first three terms represent the space-bandwidth product (SBP) along the three spatial dimensions. The fourth term represents the time-bandwidth product (TBP). The last term represents the signal-to-noise ratio (SNR) in the logarithmic scale, where s and n denote the average signal power and additive noise power, respectively. For an imaging configuration where SBP, TBP and SNR>>1, the information capacity of a single acquired volume simplifies to:

$$C_{single}=(2L_xB_x)(2L_yB_y)(2L_zB_z)(2TB_T)\log_2(s/n_{single}) \quad (\text{Eq. S2})$$

Consider repeatedly acquiring an image of a 'static' object N times. Since an object that is known a priori to be invariant in time possesses effectively zero temporal bandwidth (i.e., $B_T=0$), the factor of N increase in T does not result in an increase in the information capacity—the gain in the temporal information is essentially redundant. In other words, although N repeated acquisitions provide the capacity to support N times more information, no additional information is directly derived from each subsequent image-essentially a replica of the previous image in a 'static' sample—to actually 'occupy' this expanded capacity. Now consider coherently averaging the N acquired images of the 'static' object. This process "encodes" the originally redundant increase in T in the finite SNR term in the new coherent-averaged system. In other words, if the object is known a priori to be invariant in time, the object can be successively imaged N times (increasing T by a factor of N) and the OCT datasets coherently averaged (reducing BT by factor of N), which keeps the time-bandwidth product unchanged but suppresses the system noise by a factor of 1/N-creating a system with larger information capacity resulting from the enhanced SNR. The gain in information capacity via the SNR term of the coherent-average volume relative to the single-shot volume is given by:

$$C_{avg} = (2L_xB_x)(2L_yB_y)(2L_zB_z)(2TB_T)\log_2(s/n_{avg}); n_{avg} = n_{single}/N \quad (S3)$$

$$\frac{C_{avg}}{C_{single}} = \frac{\log_2(s/n_{avg})}{\log_2(s/n_{single})} = 1 + \frac{\log_2(N)}{\log_2(s/n_{single})} \quad (S4)$$

In this case, the redundant N times increase in T is instead transformed into a finite increase in SNR—a lossy transformation, since the information gain in Eq. S4 is less than N—that 'occupies' the expanded capacity. Based on the theorem of invariance of information capacity, the extra information capacity earned via coherent-average noise suppression can be distributed to the SBP terms (e.g., by equally increasing $B_x$ and $B_y$) in order to enhance the resolution along those dimensions. According to the information capacity $C_{avg}$ given in Eq. S3, the allowable bandwidth expansion (BE) factor, $\varepsilon_{BE}$, that can be achieved without penalty to the SNR with regard to the original single-shot volume is given by:

$$\varepsilon_{BE}^2 = \frac{B_{x,RE}B_{y,RE}}{B_xB_y} = \frac{\log_2(s/n_{avg})}{\log_2(s/n_{single})}, \quad (S5)$$

where $B_{x,RE}$, and $B_{y,RE}$ are the expanded spatial-frequency bandwidths in the x and y dimensions, respectively. Note that it is the square of BE factor that scales with the factor of log-scale SNR gain (RHS of Eq. S5) because the extra SNR is equally distributed between the two spatial dimensions in this scenario. The resolution enhancement (RE) factor, $\varepsilon_{RE}$, supported by this information exchange-process is then given by:

$$\varepsilon_{RE} = \frac{Res}{Res_{RE}} = \frac{B_{x,RE}}{B_x} = \frac{B_{y,RE}}{B_y} = \varepsilon_{BE}, \quad (S6)$$

where Res and $Res_{RE}$ denote the original and the enhanced transverse resolution, respectively. Note that since the $\varepsilon_{RE}$ is a function of the ratio of log-scale SNR, the base of the log does not influence the supported resolution enhancement (i.e., although log base 2 for SNR and information capacity in bits is used in Eq. S1-5, the same $\varepsilon_{RE}$ prediction could be obtained with log base 10 for SNR in dB scale). The factor of log-scale SNR gain and the corresponding supported RE factor are shown as a function of N in FIG. 30. Section VIII deals with more general cases where an arbitrary amount of SNR, not limited to the amount earned via coherent average, may be sacrificed to enhance resolution, as done in the silicone phantom experiment (FIG. 2).

Figure 30:
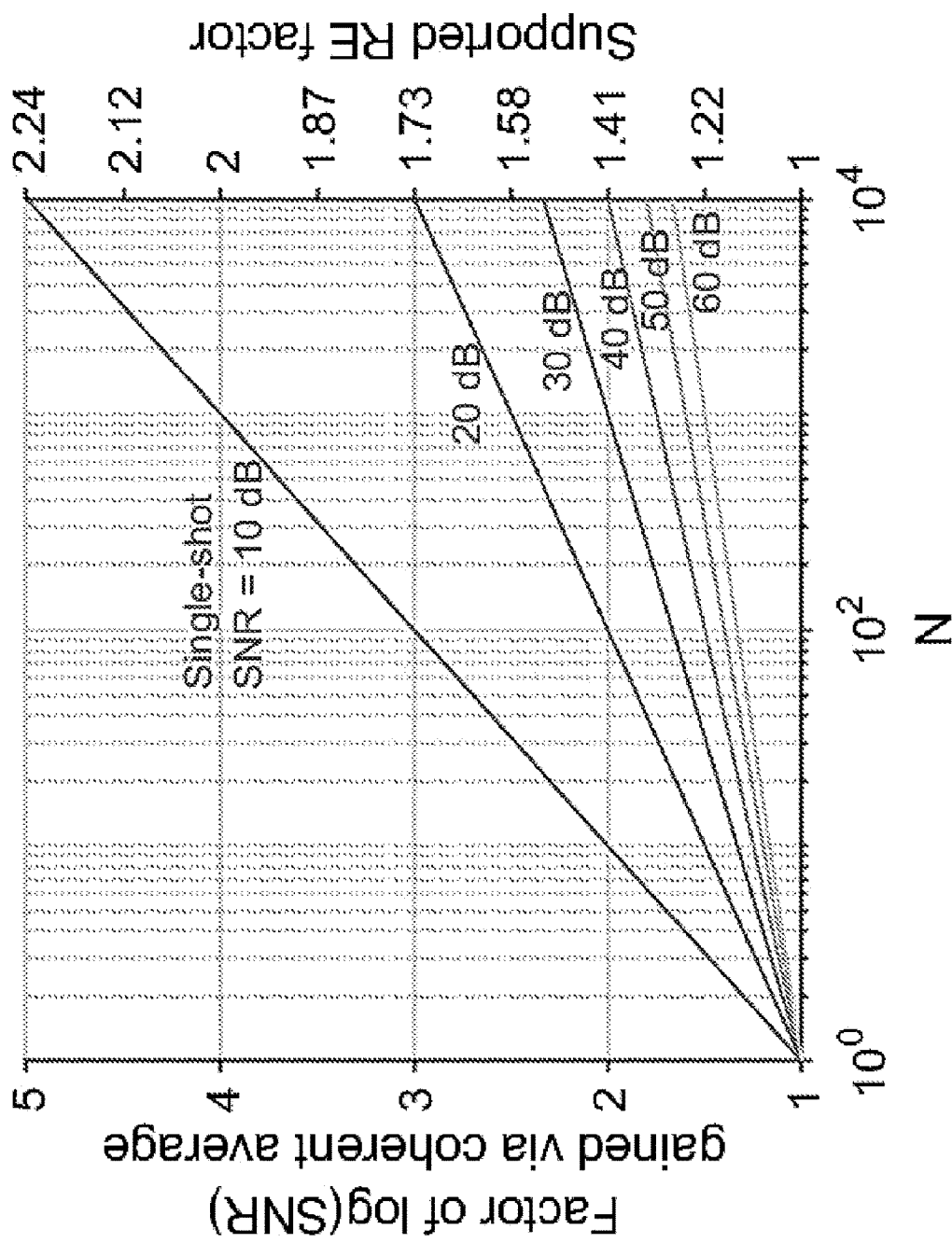
FIG. 30 shows resolution enhancement supported by coherent-average noise suppression.

FIG. 30 shows resolution enhancement supported by coherent-average noise suppression. Gain in logarithmic-scale SNR and the corresponding RE factor supported by the invariance of information capacity as a function of N. Curves are shown for different original SNR of the single-shot volume. See Section VIII for general cases where more SNR than earned may be sacrificed to enhance resolution.

Section II: System Diagram, Conjugated Imaging Configuration, and Telecentric Scanning The spectral-domain (SD)-OCT system diagram is shown in FIG. 31(a). Details of the optical components are provided in Methods. Imaging is performed in an inverted setup where the OCT beam interrogated the sample through the coverslip-bottom of the sample dish. The coverslip is essential for phase registration of individual OCT volumes (see Section IV).

FIG. 31 shows an experimental setup. FIG. 31(a) shows SD-OCT system diagram. SLD, superluminescent diode. CAM, spectrometer and line-scan camera. PC, polarization controller. FC, 50/50 fiber coupler. M, mirror. XY, 2-axis galvanometer mirrors. OBJ, objective lens. FIG. 31(b) shows under-filling of objective aperture for telecentric scanning. FIG. 31(c) shows sample configuration and example cross-sectional OCT image demonstrating imaging in the conjugated configuration. $z_f$ indicates the focal plane of the sample image.

In this setup, the coverslip would appear closer to the 0 optical path difference (OPD) if it are imaged with the reference mirror positioned for imaging in the traditional imaging configuration, causing the signal at the camera to be dominated by the strong reflection at the glass-air and glass-sample interfaces of the coverslip. In other words, the actual signal of interest from the sample would only be able to occupy a small portion of the available dynamic range of the camera as the reference arm power is adjusted to avoid saturation at the coverslip interfaces. In order to maximize the dynamic range coverage of the signal from the sample, imaging is actually performed in the conjugated configuration where the reference mirror position is adjusted to wrap the coverslip toward higher pixel depths and placed the focal plane inside the sample closer to the 0 OPD (FIG. 31(c)). This configuration exploited the spectrometer roll-off to maximize signal from the focal plane while suppressing strong reflection from the coverslip.

The SD-OCT system in FIG. 31(a) utilized telecentric beam-scanning to acquire 3D tomograms. Telecentric scanning is the preferred beam-scanning scheme in OCT in order to minimize coherence gate curvature. In such a system, the physical aperture of the objective lens is underfilled by the illumination beam in order to allow for telecentric scanning—by imaging the galvanometer mirror to the objective back focal plane—'across' the objective lens (FIG. 31(b)). Thus, the numerical aperture (NA) of the system is determined by the width of the illumination Gaussian beam (typically the $1/e^2$ width) rather than the objective aperture diameter, which sets a physical limit to the system bandwidth. The transverse resolution of the system can often be adjusted (to a certain extent) by changing the width of the illumination beam (by modifying the collimating or telescope optics) without switching the objective lens. However, there is a tradeoff between beam width and the FOV that can be supported without clipping the beam. Alternatively, an objective lens with a higher NA (e.g., shorter focal length) can be used to achieve better transverse resolution. However, there is also a tradeoff between the physical system bandwidth (i.e., objective aperture) and the supported FOV and working distance in a typical microscope.

Section III: Signal Averaging in the Space Domain and Caveats for Achieving Theoretical Noise Suppression Performance FIG. 25B shows the signal intensity of the scattering particles, silicone background, and noise after incoherent and coherent average over N acquisitions. Signal intensity (i.e., OCT magnitude-square) of the scattering particles remained unchanged in both incoherent- and coherent-average images, indicating that the signal is dominated by phase-stable backscattering from the particles. In contrast, signal intensity in the silicone background is reduced by coherent average before stabilizing after N>10 acquisitions, suggesting that the silicone medium generated phase-stable in time (albeit low-magnitude) backscattering signal that is initially 'hidden' by noise and later revealed by coherent average. Faint scattering signal from the silicone background can be at the focal plane of the coherent-average, but not the traditional single-shot image (FIG. 25A, cross-sectional image). Meanwhile, the incoherent average failed to suppress the average background intensity. Noise images of an empty sample dish are acquired to quantify the system noise (FIG. 31(c)), defined as the standard deviation of signal intensity across the transverse FOV. Both incoherent and coherent averages suppressed the noise, but the coherent average is more efficient. Noise reduction followed the theoretical trends of 1/NN and 1/N for incoherent and coherent averages, respectively, demonstrating a factor of N superior efficiency in noise suppression by coherent over incoherent average.

The theoretical coherent-average noise suppression efficiency with a factor of 1/N under is based on the premise that different realizations of noise, a circularly symmetric complex random variable, are uncorrelated. For the system implemented based on some embodiments of the disclosed technology, this condition is achieved when successive OCT volumes, acquired with a CM-mode acquisition scheme (see Methods above), are coherently averaged (FIG. 25B and FIG. 32(a), solid lines). However, noise suppression failed to reach the theoretical 1/N efficiency when successive B-scans, acquired with a BM-mode acquisition scheme (i.e., acquiring multiple B-scans at a slow-axis position, then, step to the next slow-axis position), are coherently averaged (FIG. 32(a), dashed lines). These results suggest that acquisition of multiple B-scans is required to ensure decorrelation between different realizations of noise being averaged. Notably, when nonconsecutive B-scans from the same BM-mode datasets are coherently averaged (i.e., averaging every ΔT>1 B-scans), the noise suppression performance approached the theoretical efficiency with increasing ΔT (FIG. 32(a), light dashed lines).

The distribution of noise power in the spatial-frequency domain provides additional insights into the results in FIG. 32(a). A circular Gaussian noise is expected to be uniformly distributed across spatial frequencies. This is observed in the single-shot images acquired with both CM-mode acquisition scheme (3210) and BM-mode acquisition scheme (3220)

(FIG. 32(b), left). The suppressed noise remained uniformly distributed after coherent average of successive OCT volumes (CM-mode) (3230), but not successive B-scans (BM-mode) (3240) (FIG. 32(b), right), where noise is suppressed more efficiently at higher spatial frequencies. This result suggests that only the rapidly changing noise at higher spatial frequencies became decorrelated between successive B-scans. In other words, over the shorter time scale associated with frame averaging, there is likely systematic contributions to the system noise (e.g., resulting from fluctuations of laser intensity).

Figure 32:
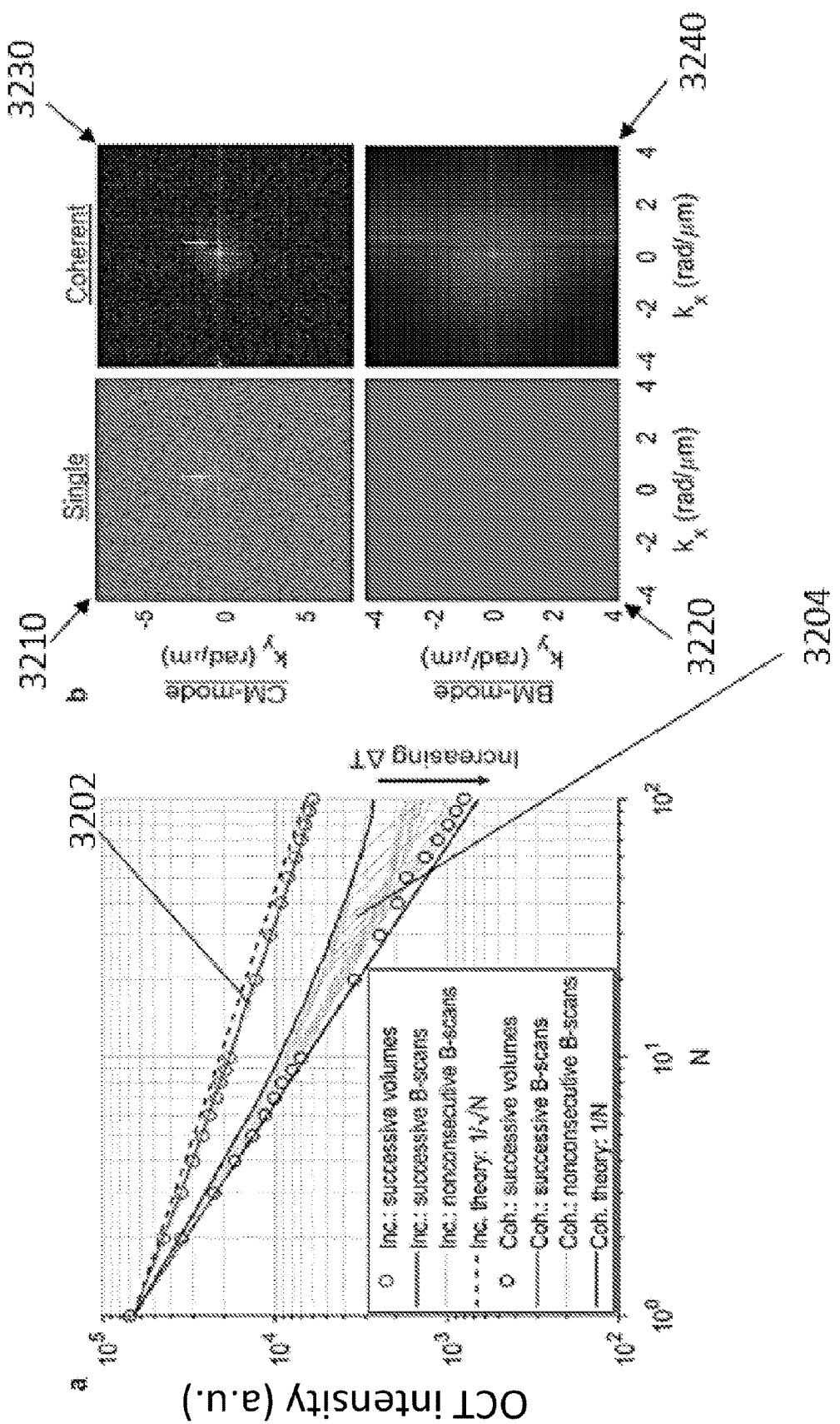
FIG. 32 shows a comparison of averaging schemes for noise suppression.

FIG. 32 shows a comparison of averaging schemes for noise suppression. FIG. 32(a) shows noise reduction as a function of N for successive-volumes (circle), successive-B-scans (solid), and nonconsecutive-B-scans (light dotted) averaging schemes for incoherent (red, 3202) and coherent (blue, 3204) average. Coherent-average noise reduction with nonconsecutive B-scans approached the optimal efficiency of successive-volumes averaging scheme as $\Delta T$ increased. FIG. 32(b) shows single-shot and coherent-average noise power in transverse spatial-frequency domain for CM- and BM-mode acquisition schemes. For FIGS. 32(a) and (b), noise data is obtained from an en face plane located inside a glass coverslip.

Section IV: RE-OCT Reconstruction Procedure

Figure 33:
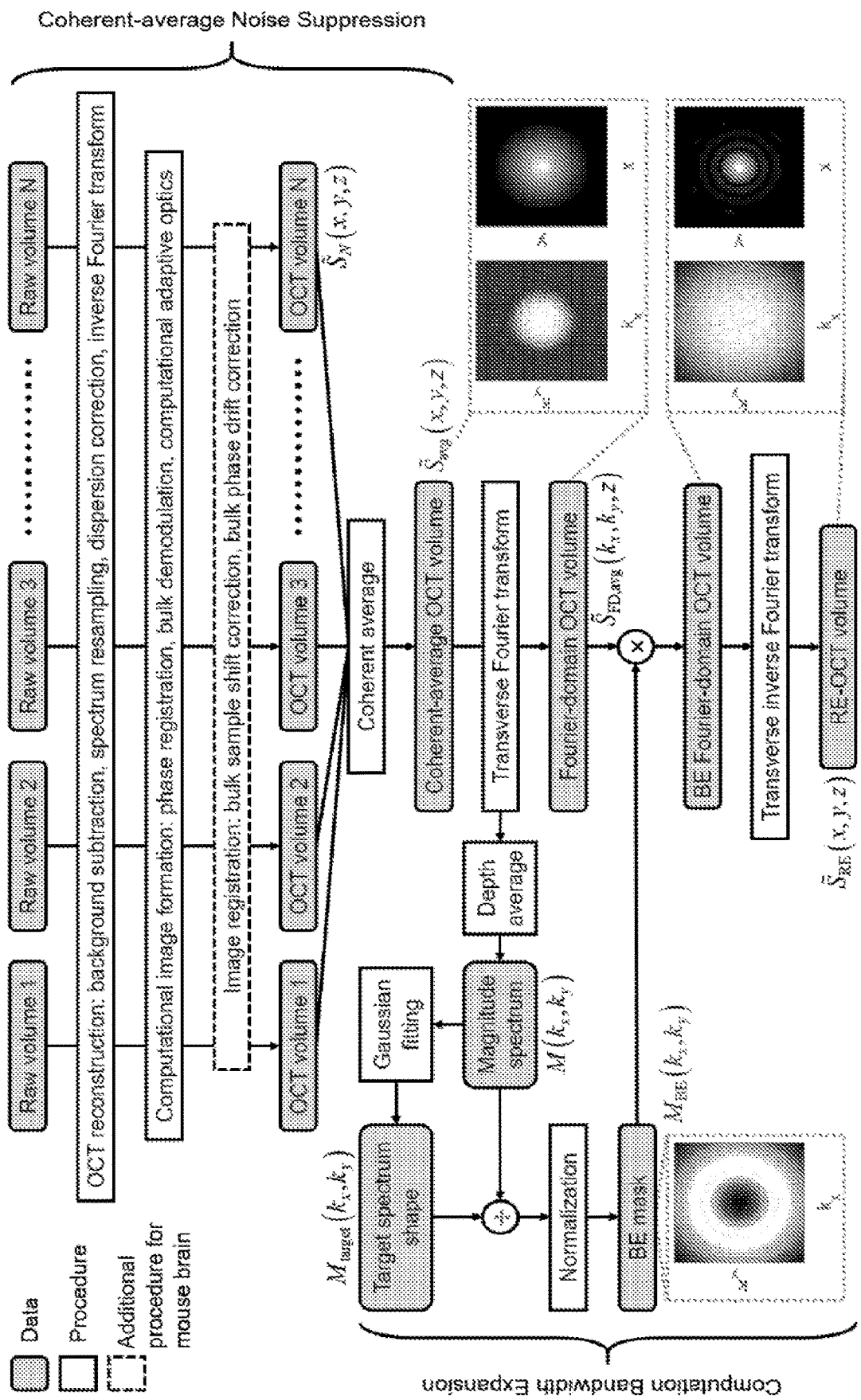
FIG. 33 shows RE-OCT reconstruction procedure.

The RE-OCT reconstruction procedure implemented in all experiments is illustrated in a flowchart in FIG. 33. First, the space-domain OCT volume from each acquisition is reconstructed by standard procedure (background subtraction, spectrum resampling, dispersion correction, and inverse Fourier transform). Defocus correction is performed on each reconstructed volume via computational image formation procedure (phase registration, bulk demodulation, and computational adaptive optics) as previously described. As a result, each OCT volume has depth-invariant transverse spatial-frequency bandwidth and resolution. For ex vivo mouse brain, additional image registration procedure is necessary in order to ensure that individual volumes are phase registered to each other in the presence of sample instability during CM-mode acquisitions (Section V).

The phase-registered OCT volumes are coherently averaged to obtain the coherent-average OCT volume via:

$$\tilde{S}_{avg}(x, y, z) = \frac{1}{N}\sum_{i=1}^{N}\tilde{S}_i(x, y, z) \quad (S7)$$

Then, the computational bandwidth expansion (BE) procedure began with computing of the Fourier-domain OCT volume via:

$$\tilde{S}_{FD,avg}(k_x, k_y, z) = FT_{x,y}[\tilde{S}_{avg}(x,y,z)], \quad (S8)$$

where $FT_{x,y}$ denotes 2D Fourier transform along the x and y dimensions, followed by a magnitude-average across depths about the focal plane $z_f$ to obtain the magnitude spectrum:

$$M(k_x, k_y) = \frac{1}{21}\sum_{i=-10}^{10}|\tilde{S}_{FD,avg}(k_x, k_y, z_{f+i})|. \quad (S9)$$

The depth averaging served to minimize the rapid noisy fluctuations in the magnitude spectrum that are present at a single plane.

FIG. 33 shows RE-OCT reconstruction procedure. Individual space-domain OCT volumes are reconstructed and processed for coherent-average noise suppression. Computational BE is performed on the coherent-average OCT volume via magnitude-based deconvolution to obtained the resolution-enhanced RE-OCT volume.

The depth-average magnitude spectrum is fit to a Gaussian curve as a function of the radial spatial frequency, $k_r = \sqrt{k_x^2 + k_y^2}$, then, the fit parameters a, c, and d are used to compute the bandwidth-expanded target spectrum shape with a given BE factor, $\varepsilon_{BE}$, via:

$$M_{fit}(k_r) = \alpha\exp(-k_r^2/c^2) + d, \quad (S10)$$

$$M_{target}(k_x, k_y) = \alpha\exp(-(k_x^2+k_y^2)(\varepsilon_{BE}C)^2) + d. \quad (S11)$$

The BE mask is computed from the target spectrum shape and the magnitude spectrum, then, normalized to ensure that the total signal power would be conserved after computational BE, as follows:

$$M_{BE}(k_x, k_y) = \frac{1}{\varepsilon_{BE}^2}\frac{M_{target}(k_x, k_y)}{M(k_x, k_y)}. \quad (S12)$$

Finally, the resolution-enhanced RE-OCT volume is obtained via magnitude-based deconvolution in the spatial-frequency domain:

$$\tilde{S}_{RE}(x,y,z) = FT_{x,y}^{-1}[M_{BE}(k_x,k_y)\tilde{S}_{FD,avg}(x,y,z)], \quad (S13)$$

where $FT_{x,y}^{-1}$ denotes 2D inverse Fourier transform along the x and y dimensions.

Section V: Image Registration Procedure for Ex Vivo Mouse Brain

The ex vivo mouse brain experienced both bulk sample shift and bulk phase drift, likely due to the temperature stabilization of the cold mouse brain and the warm mounting agarose (see Methods). In such case, image registration procedure is required to ensure that the scattering signal from different OCT volumes are phase-registered to each other prior to computing the coherent average. First, the bulk sample shift in 3D space is corrected via a Fourier transform-based image translation registration algorithm. Each OCT volume is conjugated to the $1^{st}$ volume in the spatial-frequency domain, before its bulk spatial shifts relative to the $1^{st}$ volume along x, y, and z dimensions are estimated from the peak position of space-domain impulse response via:

$$\tilde{S}_{FD,i}(k_x, k_y, k_z) = FT_{x,y,z}[\tilde{S}_i(x, y, z)]; i = 1, 2, \ldots, N, \quad (S14)$$

$$(\Delta x_i, \Delta y_i, \Delta z_i) = \underset{(x,y,z)}{\operatorname{argmax}}(FT_{x,y,z}^{-1}[\tilde{S}_{FD,i}^*(k_x, k_y, k_z)\tilde{S}_{FD,1}(k_x, k_y, k_z)]), \quad (S15)$$

where $FT_{x,y,z}$ and $FT_{x,y,z}^{-1}$ denote the 3D forward and inverse Fourier transform, and $\tilde{S}_{FD,j}^*$ denotes the complex conjugate of $\tilde{S}_{FD,j}$, respectively. Then, the bulk spatial shifts $\Delta x_i$, $\Delta y_i$, and $\Delta z_i$ are applied back to the $i^{th}$ volume as phase ramps to spatially register it to the $1^{st}$ volume via:

$$\tilde{S}_{i,shift-corrected}(x,y,z) = FT_{x,y,z}^{-1}[\tilde{S}_{FD,i}(k_x,k_y,k_z)\exp(-j2\pi(k_x\Delta x_i+k_y\Delta y_i+k_z\Delta z_i))], \quad (S16)$$

where $j=\sqrt{-1}$.

Figure 34:
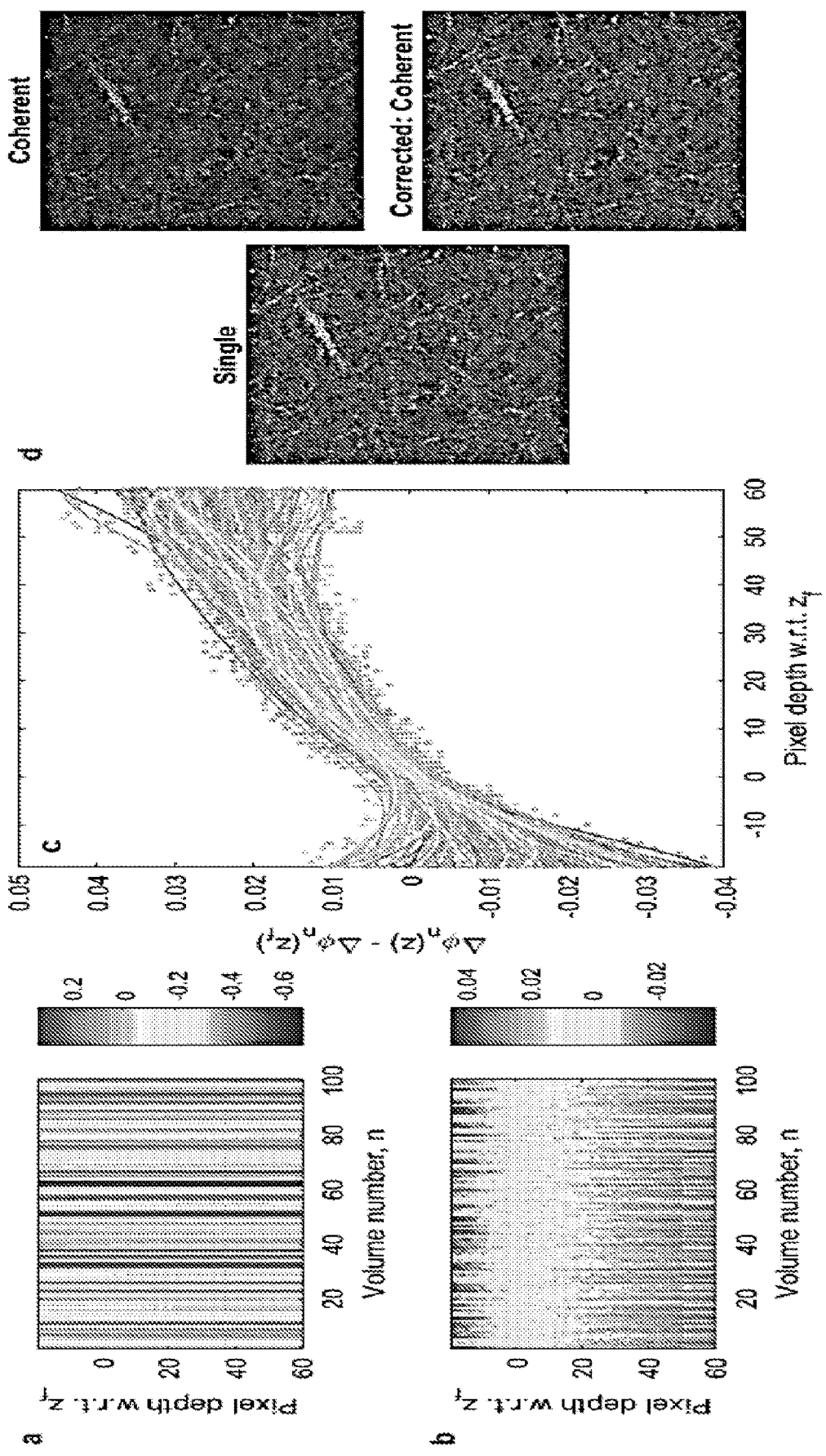
FIG. 34 shows bulk phase drift correction in ex vivo mouse brain.

FIG. 34 shows bulk phase drift correction in ex vivo mouse brain. FIG. 34(a) shows a bulk phase difference between adjacent volumes $\Delta\phi_i(z)$ at each pixel depth. FIG. 34(b) shows a bulk phase difference in the focal plane, $\Delta\phi_i(z)-\Delta\phi_i(z^f)$, to show the depth dependence. FIG. 34(c) shows depth-dependent polynomial curve fits of bulk phase difference for different volumes in b. FIG. 34(d) shows single-shot and coherent-average images with and without image registration (same colormap range).

After correcting for the bulk sample shift, a bulk phase difference between adjacent volumes is estimated at each pixel depth k via:

$$\Delta\phi_i(z_k) = \angle\left(\sum_{x,y}[\tilde{S}_{i,shift-corrected}(x, y, z_k)\tilde{S}^*_{i-1,shift-corrected}(x, y, z_k)]\right); \quad (S17)$$

$$i = 2, 3, \ldots, N,,$$

which represents the magnitude-weighted average phase difference across each en face plane (FIG. 34(a)). Each of the $i^{th}$ phase difference is fit to a $6^{th}$-order polynomial function as a function of z via linear least-square curve fitting to obtain a depth-dependent phase shift between adjacent volumes (FIG. 34(c)). The cumulative depth-dependent phase drift up to the $i^{th}$ volume is removed from each subsequent volume to phase-register it to the $1^{st}$ volume via:

$$\tilde{S}_{i,phase-registered}(x, y, z) = \tilde{S}_{i,shift-corrected}(x, y, z)\exp\left(-j\sum_{n=1}^{i}\Delta\phi_n(z)\right); \quad (S17)$$

$$i = 2, 3, \ldots, N.$$

FIG. 34(d) shows the comparison between the coherent-average images of the ex vivo mouse brain with and without image registration.

Section VI: Simulation of RE-OCT in Silicone Phantom

In order to understand the factors that limit achievable resolution enhancement in RE-OCT, a set of simulated en face planes are generated with the same number of pixels (450×450 pixels), transverse FOV (180 µm×180 µm) and spatial sampling (0.4 µm/pixel) as the silicone phantom datasets in FIGS. 1 and 2. The simulated en face planes consisted of three components: scattering particles (FIG. 34(a)), silicone background (FIG. 34(b)), and system noise (FIG. 34(c)).

Figure 35:
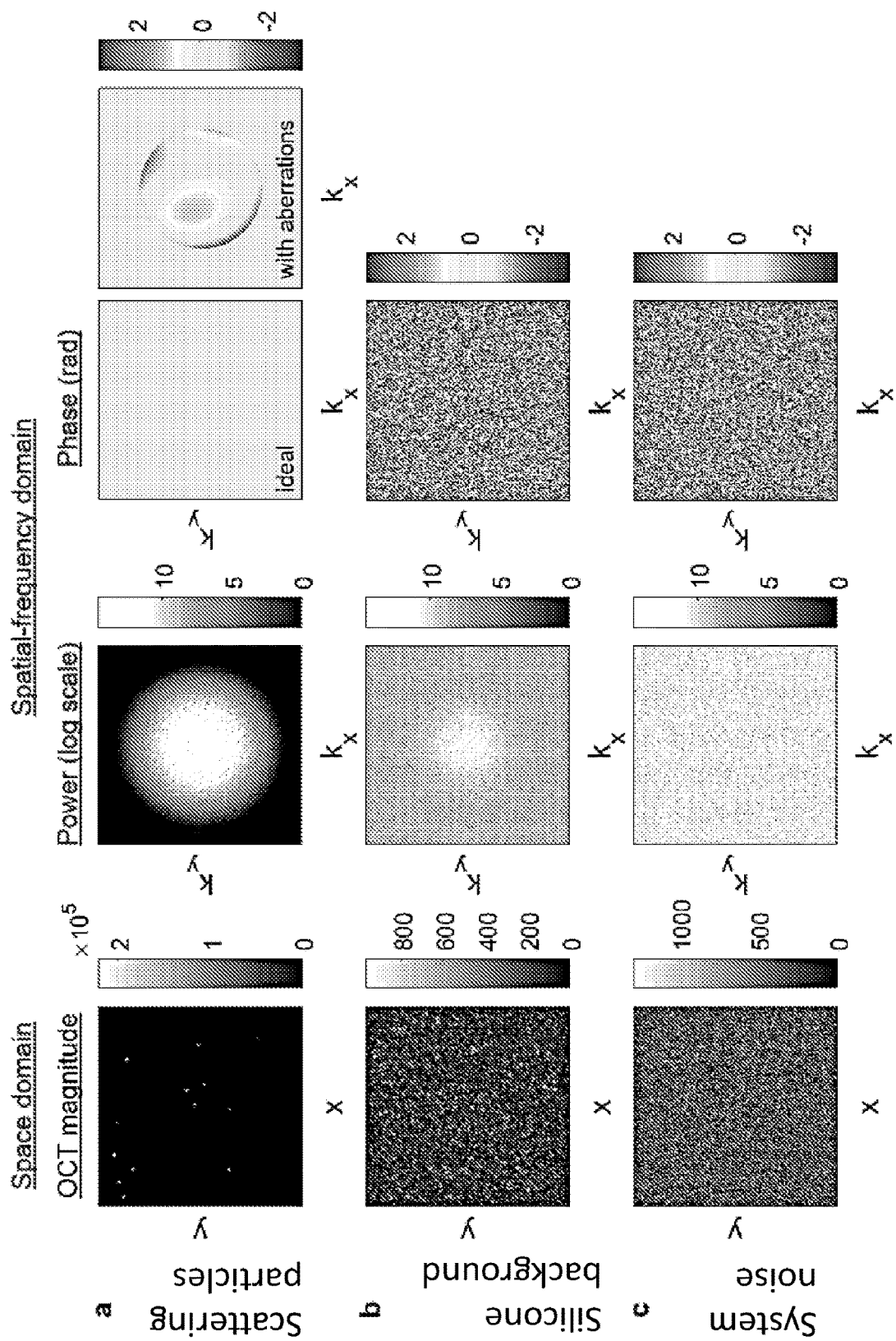
FIG. 35 shows components of simulated en face planes.

FIG. 35 shows components of simulated en face planes, including space-domain OCT magnitude image (left), and spatial-frequency-domain power (middle) and phase (right) spectra of simulated scattering particles, silicone background, and system noise, respectively. Phase spectra in a show the pupil phase applied to the simulated Gaussian PSFs. Note the power spectrum shape of the silicone background, in contrast to the uniformly distributed spectrum of the random system noise.

Each component is generated as follows:
Scattering particles. 2D symmetric Gaussian point spread functions (PSF) with full width at half-maximum (FWHM) of 2.1 µm, matching the native transverse resolution of the system, and peak magnitudes matching the OCT signal magnitudes of the scattering particles from the focal plane of the silicone phantom datasets (FIG. 35(a)). For the simulated case with optical aberrations, an aberrated phase profile computed with Zernike polynomials are added to the Gaussian PSFs (FIG. 35(a), right).
Silicone background. Complex OCT signal of the silicone medium from the focal plane of the silicone phantom datasets. First, the scattering particles are removed from the en face image via a magnitude threshold. Then, the gaps left behind at the particle locations are "filled in" by a patch of silicone image from another region (FIG. 35(b)).
System noise. A 450×450 array of circularly symmetric complex random variable with a mean intensity (i.e., magnitude$^2$) equivalent to that of the single-shot noise intensity from the focal plane of the silicone phantom datasets in FIG. 25B (FIG. 35(c)). For a coherent-average image across N acquisitions, the array of complex random variable is repeatedly generated for N iterations and coherently averaged.

A total of six simulated en face planes are generated: noise only (scattering particles+system noise), noise with background (scattering particles+silicone background+system noise), and noise-free limit (scattering particles only), each of the three cases with and without optical aberrations. The RE-OCT procedure is performed on each of the simulated en face planes as described in Section IV. The resolution and SBR results are computed as described in Methods. Although physical aperture imposed by the objective lens has not been included in the simulations, the relevant spatial frequencies in our simulations remain within the double-pass pupil of the OCT system used for the presented experimental results (maximum spatial frequency of 6.67 rad/um for our 0.45 NA objective lens).

Section VII: Noise, Dynamic Range, and Phase Correlation in the Spatial-Frequency Domain System noise limits not only the available DR of the image, but also the spatial-frequency bandwidth over which signal phase remains correlated in spatial frequency. In order to investigate the results observed in FIGS. 1c-e over a wider range of noise levels, simulated en face planes containing scattering particles and system noise (i.e., noise only case described in Section VI above) are generated for coherent average over a range of N=1 (FIG. 36(a)) through N=10$^5$ (FIG. 36(b)) acquisitions. DR and phase-correlation limit, $k_{phase-corr}$, in the spatial-frequency domain are computed for each simulated en face plane as described in Methods.

Figure 36:
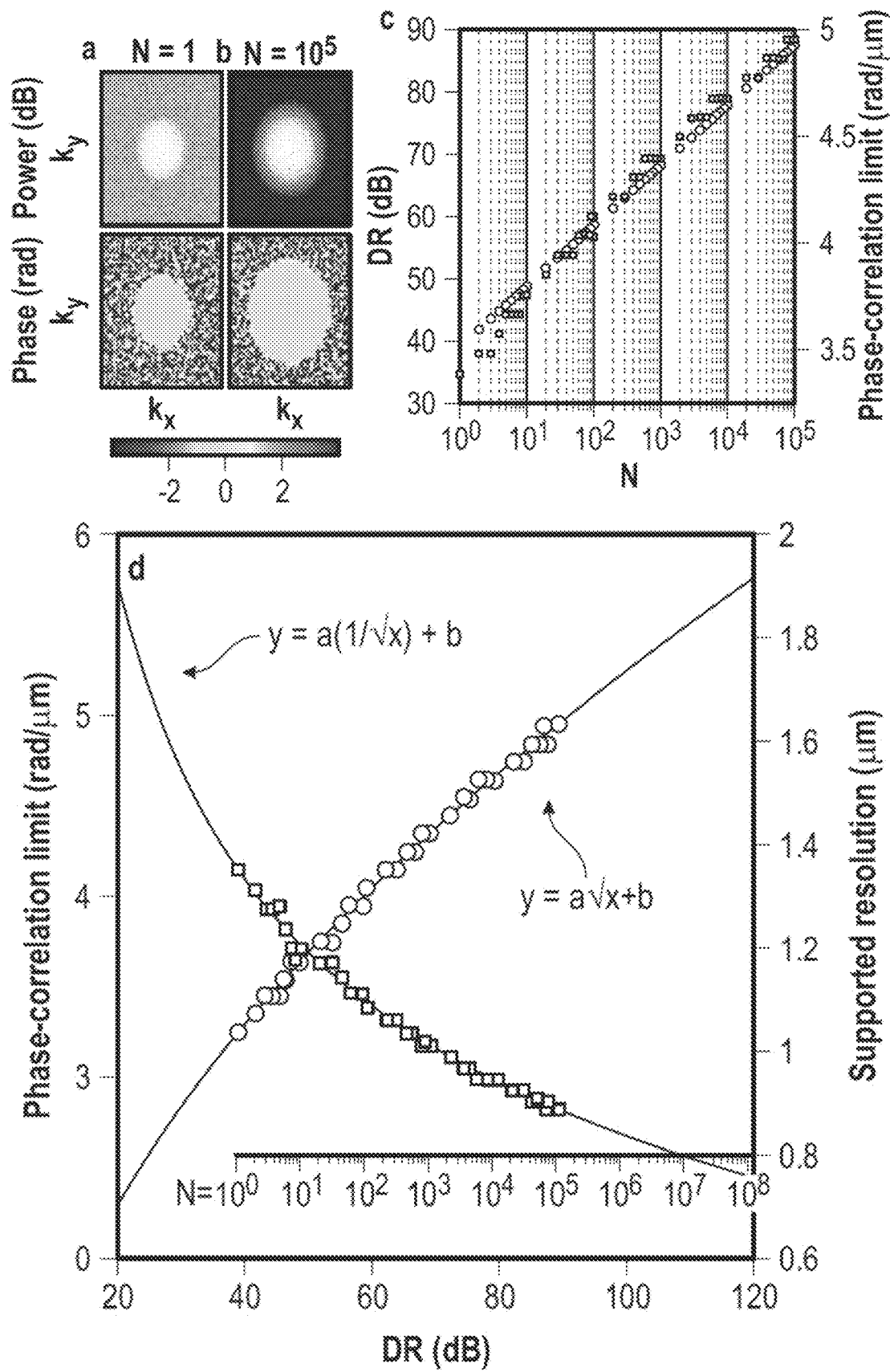
FIG. 36 shows noise-limited dynamic range and phase-correlation limit.

FIG. 36 shows noise-limited dynamic range and phase-correlation limit. FIG. 36, at (a) and (b), shows power and phase of simulated single-shot (N=1) and coherent-average (N=10$^5$) image in transverse spatial-frequency domain. FIG. 36(c) shows DR (black) and phase-correlation limit (blue) as a function of N. FIG. 36(d) shows phase-correlation limit (blue) and the supported resolution (red) as a function of DR. Both simulation results (marker) and curve-fits (line) are shown. Inset shows corresponding N required for the DR values.

Both DR and phase-correlation limit increases as the system noise is further suppressed via coherent average over larger N (FIG. 36(c)). For the definition of the phase-correlation limit implemented here (see "Methods"), the phase-correlation limit corresponds to the spatial frequency at which the signal power is roughly 16 dB above the system noise floor. Given the quadratic drop of the Gaussian spectrum tail on the logarithmic scale, the increase in phase-correlation limit from coherent-average noise suppression becomes less efficient at increasing N, even though DR increases linearly with N on the logarithmic scale (i.e., noise suppression factor of 1/N). This diminishing efficiency can be seen on the plot of phase-correlation limit as a function of DR, where the phase-correlation limit scales with square root of DR (FIG. 36(d), blue). The phase-correlation limit also provides an estimate of the best possible resolution that the system can support (FIG. 36(d), red)—given by $\lambda/(2NA_{max})$ and $kNA_{max}=k_{phase-corr}$, where k is the wave number—under the premise that signal from higher spatial frequencies beyond the phase-correlation limit cannot constructively interfere, thus, cannot contribute to the localization of PSF energy in the space domain.

Section VIII: Fundamental Limits to Resolution Enhancement in RE-OCT

RE-OCT utilizes the framework for resolution enhancement based on gaining extra SNR via coherent-average noise suppression and the theorem of invariance of information capacity presented in Section I above. However, the amount of resolution enhancement in RE-OCT need not be limited to that of the SNR gain obtained through coherent averaging. In fact, the BE factor can be selected to achieve the most optimal combination of DR and resolution, depending on the SNR penalty that can be tolerated in an application. In a general case where any BE factor may be applied, the theoretically achieved RE factor and the accompanying SNR penalty based on Cox an $$\frac{Res_{native}}{Res_{RE-OCT}} = \frac{B_{RE}}{B_{native}} = \sqrt{\frac{\log_2(s/n_{avg})}{\log_2(s/n_{RE})}}, \quad (S19)$$

where $B_{native}$ and $B_{RE}$ denote the isotropic spatial-frequency bandwidth in both x and y dimensions before and after computational BE, respectively. In principle, the resolution is enhanced by as much as the bandwidth is expanded (i.e., RE factor=BE factor), and the bandwidth can be expanded by as much as one is willing to sacrifice the SNR (according to the theorem of invariance of information capacity). The SNR penalty (in dB) in exchange for a given BE factor is 10 $\log_{10}(n_{avg}/n_{RE})$, where $n_{RE} \geq n_{avg}$ for BE factor≥1. This is the minimum SNR that must be 'earned' via coherent average if one are to maintain the original single-shot SNR in the final RE-OCT image.

FIG. 37 shows fundamental limits to resolution enhancement in RE-OCT. FIG. 37(a) shows RE factor as a function of initial SNR (or DR in the spatial-frequency domain) before computational BE supported by the theorem of invariance of information capacity at different amount of SNR penalty (blue, 3702) and the additional practical limit imposed by the noise-limited phase-correlation limit (red, 3704). Each blue curve 3702 is labeled with the SNR penalty and the number of acquisitions N required in coherent-average noise suppression to fully compensate for the loss. Shaded region 3710 under the red curve represents the practical "RE-OCT operating range." Black marker 3720 indicates the experimental performance in silicone phantom in FIGS. 25 and 26, where in principle, the performance may be adjusted up or down within the operating range to prioritize resolution or SNR, respectively. b, Relative power as a function of radial spatial frequency of the single-shot (light blue, DR=40 dB), coherent-average (dark blue, DR=60 dB), and RE-OCT (green, DR=32 dB) images of the silicone phantom (FIG. 26A). An estimate of −28 dB in SNR has been sacrificed during the computational BE procedure to produce the RE-OCT image in FIG. 26.

The resolution enhancement supported by Cox and Sheppard's information capacity framework (See Eq. 3 and Eq. 5 above) with different amounts of SNR penalty is shown as a function of the initial SNR before computational BE (FIG. 37(a), blue 3702). Ironically, starting with a lower initial SNR supports larger RE factor for a given dB sacrificed (i.e., each individual curve has a decreasing trend). However, starting with a higher SNR means there is more SNR to sacrifice by computational BE before the final SNR of the bandwidth-expanded image drops below 0 dB. More importantly, this fundamental limit based on the theorem of invariance of information capacity does not account for the implication of noise on the phase correlation in the spatial-frequency domain—that is, the impact of phase decorrelation on disrupting the constructive interference that is required to produce the optimal resolution in space. The SNR-limited phase-correlation limit, $k_{phase-corr}$, in the spatial-frequency domain imposes another upper limit to the best possible resolution that the system can support, based on the spatial-frequency bandwidth over which phase remains correlated (FIG. 36(d) in Section VII). Taking the simulation results in FIG. 36(d) and $Res_{native}$=2.1 µm, the resolution enhancement supported by the noise-limited phase-correlation limit is shown (in red) on top of the theoretical information-capacity limit in FIG. 37(a). Note that the simulation results in FIG. 36(d) only account for the effects of system noise; there are other factors that can disrupt phase correlation in the spatial-frequency domain, thus, further limiting the achievable resolution enhancement, in practice (as discussed in the main manuscript).

The red shaded region (3710 in FIG. 37(a)) under the curve 3704 represents the practical "RE-OCT operating range." The experimental performance in silicone phantom (i.e., a coherent-average DR of 60 dB going into computational BE with a BE factor of 2.4, resulting in an RE factor of 1.5) is indicated by a black marker (3720 in FIG. 37(a)). In principle, this asterisk (3720 in FIG. 37(a)) can be flexibly moved up (to achieve better resolution improvement while sacrificing more SNR) or down (to preserve more SNR while achieving less resolution improvement) within the shaded region (3710 in FIG. 37(a)), at a given initial coherent-average SNR going into computational BE (FIG. 37(a), black arrows 3730). The experimental performance suggests that roughly 33 dB in SNR is sacrificed during the computational BE procedure, where the −33 dB dashed curve (3740 in FIG. 37(a)) intersects the black marker (3720 in FIG. 37(a)). This SNR penalty is slightly more than the −28 dB estimate based on the relative power spectrum of the bandwidth-expanded versus coherent-average image (FIG. 37(b)). These results suggest that there may be slight discrepancies between the true SNR in the space domain of the RE-OCT image and the estimated DR in the spatial-frequency domain.

Resolution-enhanced (RE)-OCT in silicone phantom with increasing bandwidth expansion (BE) factor. a, Single-shot, coherent-average, BE single-shot, and RE-OCT power spectrums (log scale) and space-domain en face OCT image with zoomed PSF (linear scale). Resolution and SBR represent mean±standard deviation of measurements from 11 particles. Scale bars, 40 µm (en face image) and 2 µm (zoomed PSF). b and c, Cross-sectional profiles of zoomed PSF in a on peak-normalized linear and log scales.

Resolution-enhanced (RE)-OCT in fibrous collagen gel with increasing bandwidth expansion (BE) factor. a, Single-shot and RE-OCT en face OCT images with zoomed insets regions indicated by boxes. Scale bars, 40 µm (full) and 20 µm (zoomed). b and c, Cross-sectional profiles of a line connecting from small to larger green dots in the green zoomed insets in a on linear and peak-normalized log scales.

Resolution-enhanced (RE)-OCT in the cortex of ex vivo mouse brain with increasing bandwidth expansion (BE) factor. a, Single-shot and RE-OCT en face OCT images with zoomed insets regions indicated by boxes. Images are taken in the first cortical layer at approximately 100 m below surface.× markers in the green zoomed insets indicate one of the neurons, which appear as darker circles due to weak OCT scattering. Green inset shows that neuron in BE single-shot image is barely discernible due to the SNR penalty without coherent-average noise suppression. Scale bars, 40 µm (full) and 20 µm (zoomed). b and c, Cross-sectional profiles of a line connecting from small to large green dots in the green zoomed insets in a on linear and peak-normalized log scales. The green ×marker indicates its corresponding position on the image.

Figure 38A:
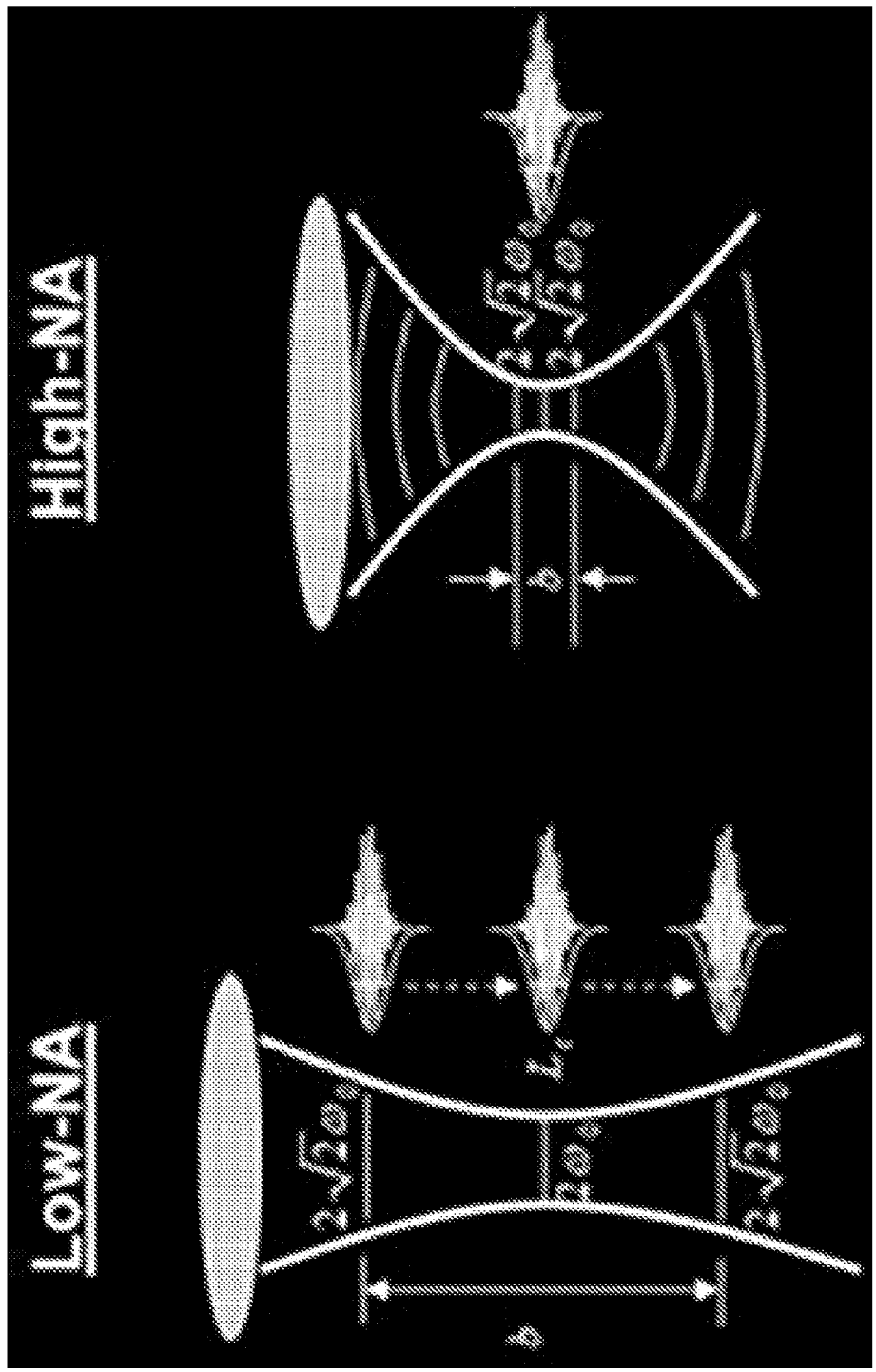
FIG. 38A shows a computational defocus correction.
Figure 38B:
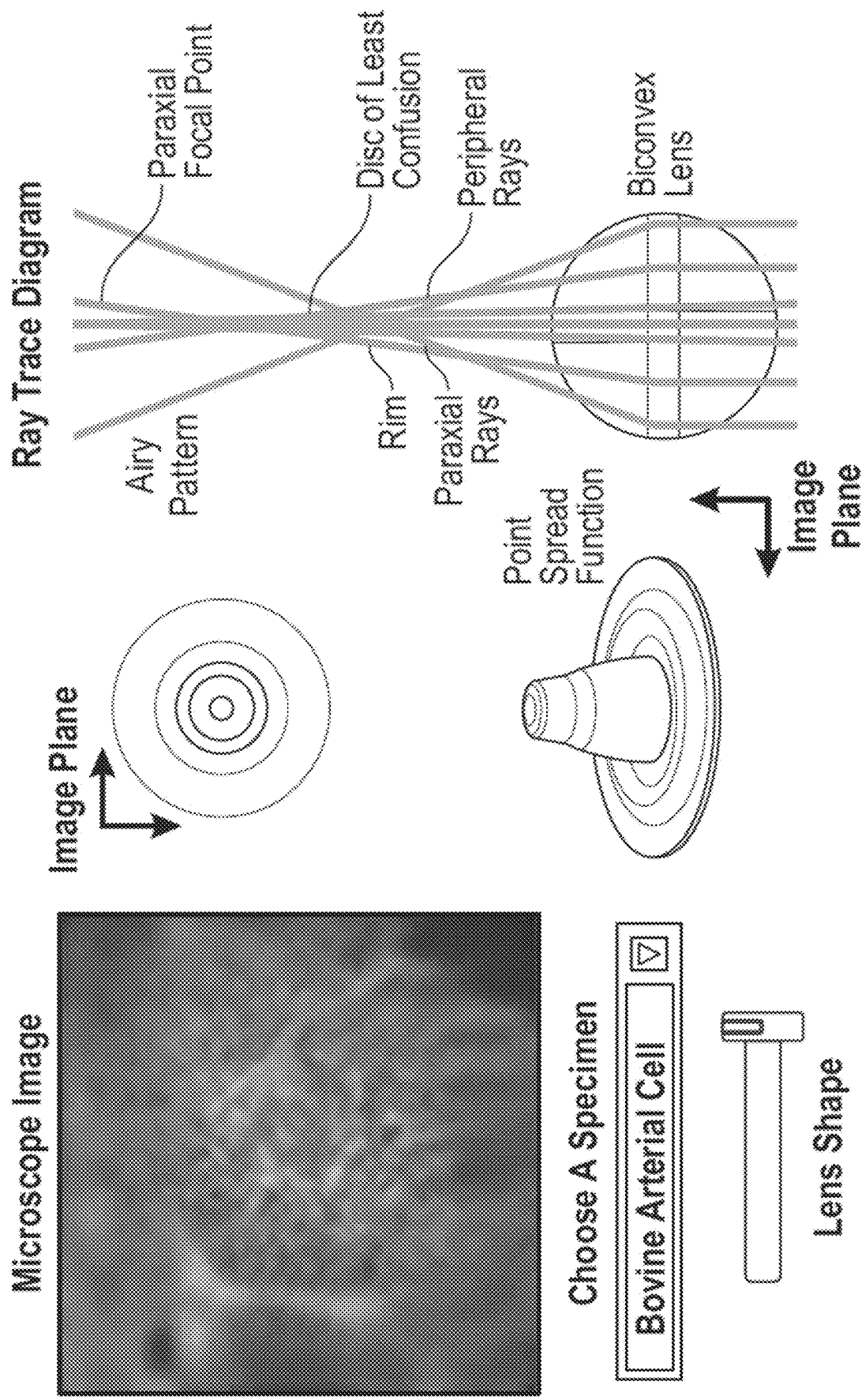
FIG. 38B shows a computational aberration correction.
Figure 38C:
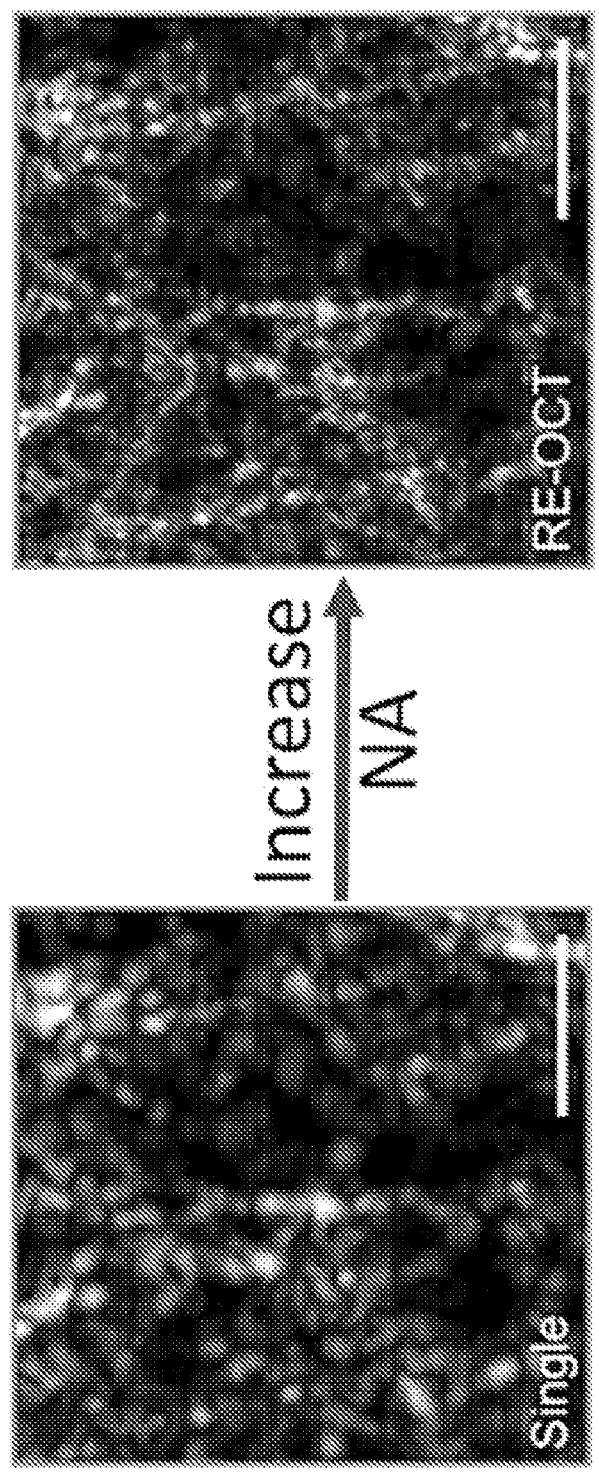
FIG. 38C shows a computational bandwidth expansion.

FIG. 38A shows a computational defocus correction, where the depth-of-field and resolution trade-off in a high-NA optical system can be overcome in post-processing to restore the diffraction-limited focal-plane resolution across depths. FIG. 38B shows a computational aberration correction, where optical aberrations induced by the sample and/or optical system can be corrected in post-processing to restore the diffraction-limited image quality. FIG. 38C shows a computational bandwidth expansion in RE-OCT, effectively increasing the NA to enhance the visualization of fine microstructural features in the image.

Figure 39:
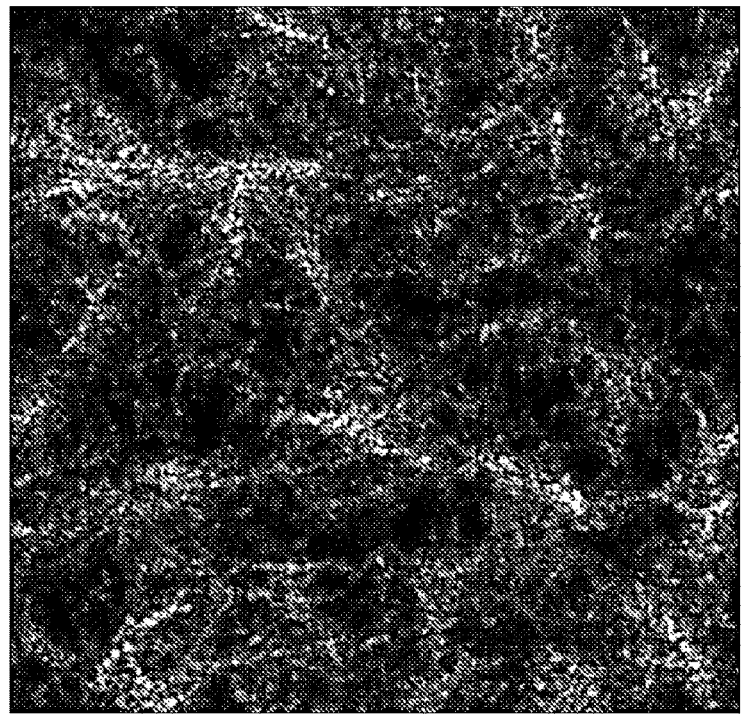
FIG. 39 shows a comparison between traditional OCT and resolution-enhanced OCT.
Figure 39:
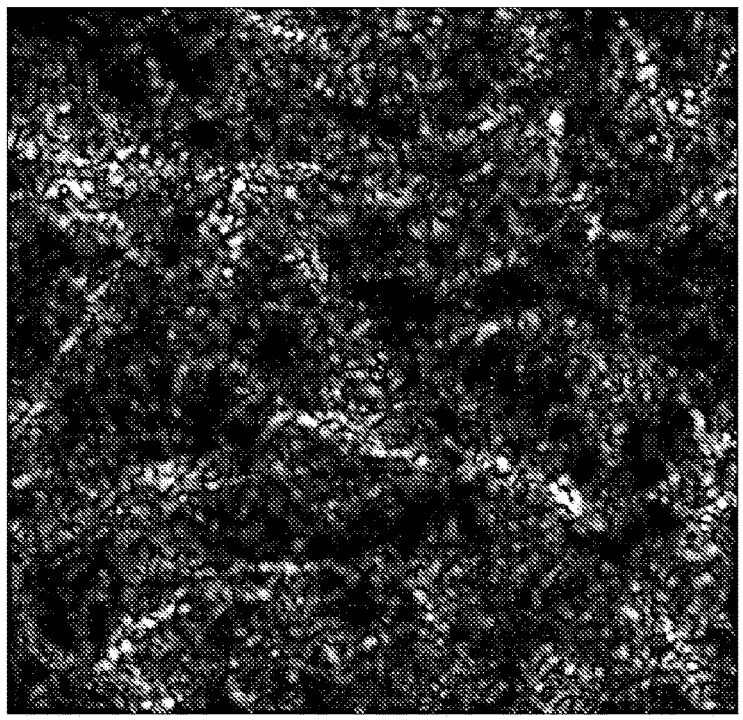

FIG. 39 shows a comparison between traditional OCT and resolution-enhanced OCT. As discussed above, the disclosed technology can be implemented in some embodiments to enhance the resolution of a beam-scanned OCT system without modifying the optical system.

Figure 40:
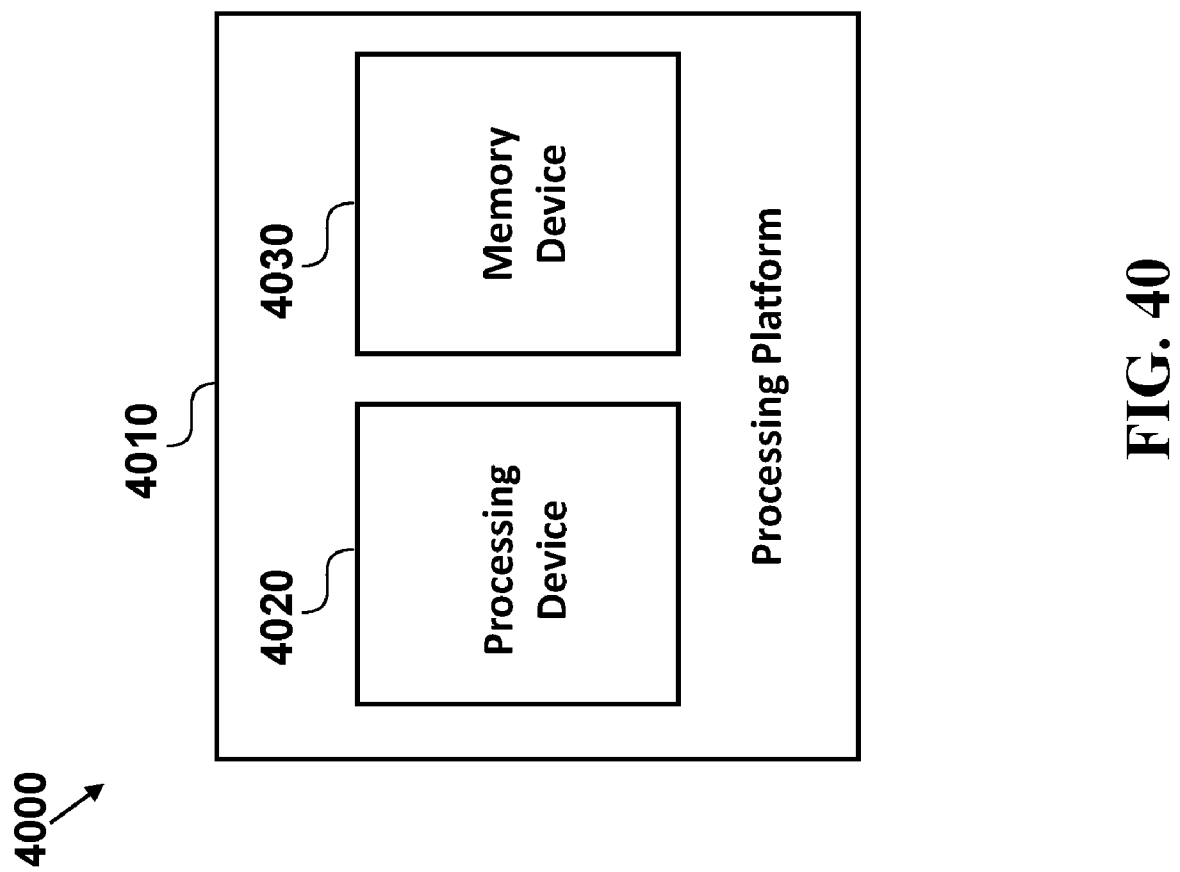
FIG. 40 shows an example system based on some embodiments of the disclosed technology.

FIG. 40 shows an example system based on some embodiments of the disclosed technology. In some implementations, a system 4000 includes a processing platform 4010. In some implementations, the processing platform 4010 includes one or more processing devices 4020 and one or more memory devices 4030. In some implementations, the processing platform is configured to perform methods disclosed in this patent document, such as the resolution-enhanced optical coherent tomography (RE-OCT) procedure discussed above.

Figure 41:
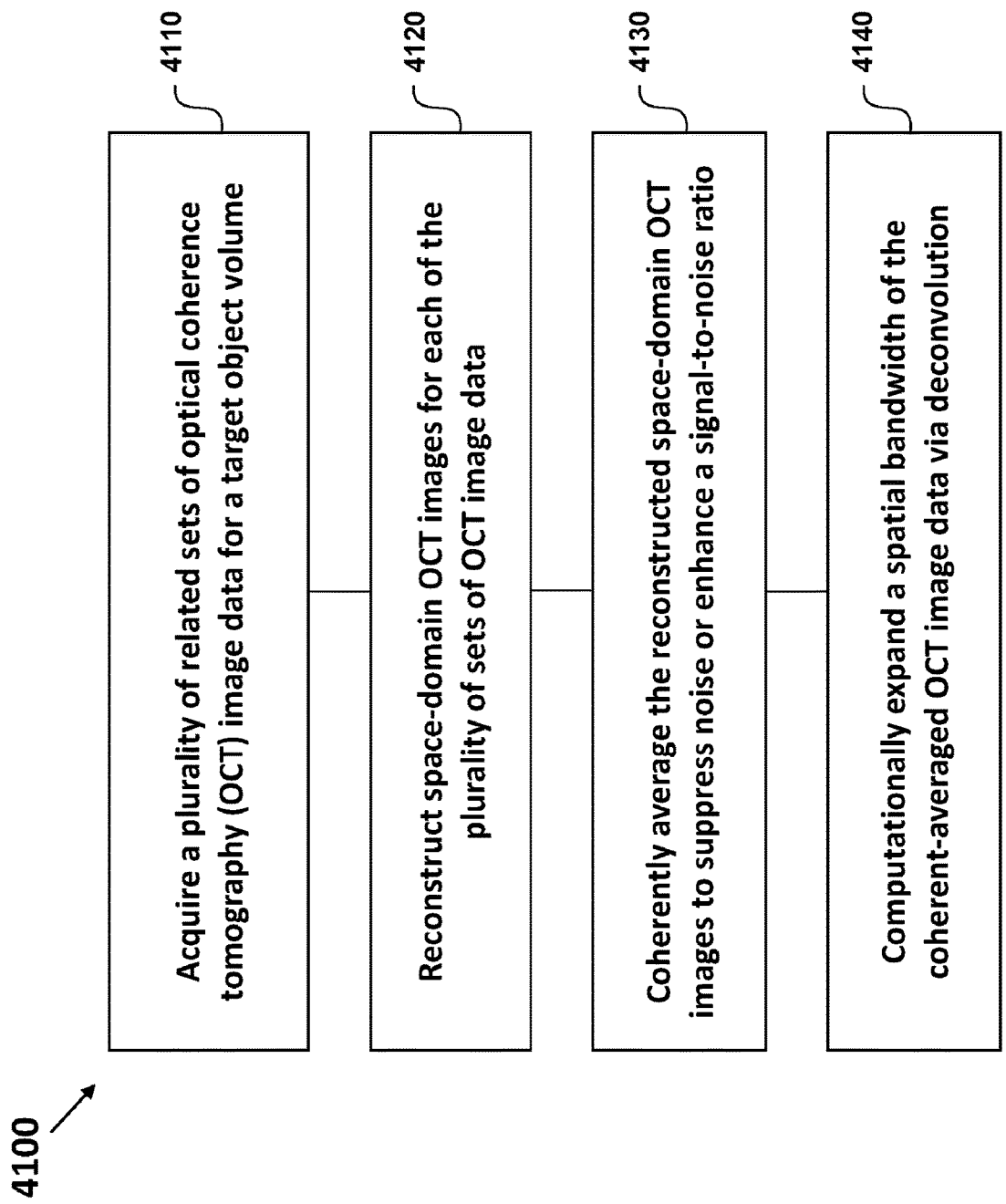
FIG. 41 shows an example of a resolution-enhanced optical coherent tomography (RE-OCT) procedure based on some embodiments of the disclosed technology.

FIG. 41 shows an example of a resolution-enhanced optical coherent tomography (RE-OCT) procedure based on some embodiments of the disclosed technology.

In some implementations, an RE-OCT procedure 4100 includes, at 4110, acquiring a plurality of related sets of optical coherence tomography (OCT) image data for a target object volume, at 4120, reconstructing space-domain OCT images for each of the plurality of sets of OCT image data, at 4130, coherently averaging the reconstructed space-domain OCT images to suppress noise or enhance a signal-to-noise ratio, and, at 4140, computationally expanding a spatial bandwidth of the coherent-averaged OCT image data via deconvolution.

Therefore, various implementations of features of the disclosed technology can be made based on the above disclosure, including the examples listed below.

Example 1. A system comprising: a processing platform comprising one or more processing devices operatively coupled to one or more memory devices; the processing platform being configured to: acquire a plurality of related sets of optical coherence tomography (OCT) image data for a target object volume; reconstruct space-domain OCT images for each of the plurality of sets of OCT image data; coherently average the reconstructed space-domain OCT images to suppress noise or enhance a signal-to-noise ratio; and computationally expand a spatial bandwidth of the coherent-averaged OCT image data via deconvolution.

Example 2. The system of example 1, wherein the processing platform is further configured to computationally expand a spatial bandwidth of the coherent-averaged OCT image data via a magnitude-based deconvolution.

Example 3. The system of example 1 or example 2, wherein the processing platform is further configured to register the plurality of sets of OCT image data relative to the target object volume or volumes prior to the reconstructing of the space-domain OCT images for each of the plurality of sets of OCT image data and to then coherently average the reconstructed registered OCT image data to suppress noise or to enhance a signal-to-noise ratio.

Example 4. The system of example 1 or example 2, wherein the processing platform is further configured to phase-register the plurality of sets of OCT image data relative to the target object volume or volumes prior to the reconstructing of the space-domain OCT images for each of the plurality of sets of OCT image data and to then coherently average the reconstructed phase-registered OCT image data to suppress noise or to enhance a signal-to-noise ratio.

Example 5. The system of any of examples 1-4, wherein the reconstructing of the space-domain OCT images for each of the plurality of sets of OCT image data comprises background subtraction, spectrum resampling, dispersion correction, and/or inverse Fourier transformation.

Example 6. The system of any of examples 1-5, wherein the processing platform is further configured to implement image processing and/or image registration following the reconstructing of the space-domain OCT images for each of the plurality of sets of OCT image data.

Example 7. The system of example 6, wherein the image processing comprises coherence-gate curvature correction, coherence-gate curvature removal, defocus correction, and/or computational adaptive optics.

Example 8. The system of example 6 or example 7, wherein the image registration comprises correction for movement of the target volume as between the plurality of sets of OCT image data.

Example 9. The system of example 6 or example 7, wherein the image registration comprises bulk phase drift correction, elastic image registration, and/or bulk phase drift correction.

Example 10. The system of any of examples 1-9, wherein the processing platform is further configured, in computationally expanding the spatial bandwidth of the coherent-averaged OCT image data via magnitude-based deconvolution, to compute a 2D Fourier transform of a coherent-averaged volume of the coherent-averaged reconstructed space-domain OCT images along a transverse dimension.

Example 11. The system of example 10, wherein the processing platform is further configured to average the magnitude of the 2D Fourier transform across between about 10-30 depths about the focal plane to obtain a magnitude spectrum of an image.

Example 12. The system of example 11, wherein the magnitude spectrum of the image is curve fit to a predetermined curve.

Example 13. The system of example 11, wherein the magnitude spectrum of the image is curve fit to a Gaussian curve.

Example 14. The system of example 11, wherein the processing platform is further configured to identify systematic noise patterns in the magnitude spectrum of the image.

Example 15. The system of any of examples 12-14, wherein the processing platform is further configured to compute a target spectrum shape with expanded bandwidth.

Example 16. The system of example 15, wherein the processing platform is further configured to compute a target spectrum shape with an expanded bandwidth.

Example 17. The system of example 16, wherein the target spectrum shape is a Gaussian spectrum.

Example 18. The system of example 17, wherein the target spectrum shape is a flattop spectrum.

Example 19. The system of any of examples 15-18, wherein the processing platform is further configured to compute a bandwidth expansion mask as the target spectrum shape divided by the original magnitude spectrum.

Example 20. The system of any of examples 15-19, wherein the processing platform is further configured to edit spatial frequencies in the bandwidth expansion mask responsive to systematic noise patterns in the magnitude spectrum of the image.

Example 21. The system of any of examples 19-20, wherein the processing platform is further configured to generate a product by multiplying the 2D Fourier transform and the bandwidth expansion mask.

Example 22. The system of example 21, wherein the processing platform is further configured to compute the 2D inverse Fourier transform of the product to generate a final resolution-enhanced space-domain image.

Example 23. The system of any of examples 1-22, wherein the plurality of related sets of optical coherence tomography (OCT) image data for a target object volume comprises at least one set of resolution enhanced (RE-OCT) image data and at least one set of aberration-diverse (AD-OCT) image data.

Example 24. The system of any of examples 1-23, wherein the plurality of related sets of OCT image data for a target object volume comprises acquire multiple repeated OCT volumes of the target object volume successively.

Example 25. A computer program product comprising a non-transitory processor-readable storage medium having stored therein an instruction set for execution by at least one processing device of a processing platform to cause the at least one processing device to perform acts comprising: acquiring a plurality of related sets of optical coherence tomography (OCT) image data for a target object volume; reconstructing space-domain OCT images for each of the plurality of sets of OCT image data; coherently averaging the reconstructed space-domain OCT images to suppress noise or enhance a signal-to-noise ratio; and expanding a spatial bandwidth of the coherent-averaged OCT image data via deconvolution.

Example 26. The computer program product of example 25, wherein the instruction set is to further cause the at least one processing device to computationally expand a spatial bandwidth of the coherent-averaged OCT image data via a magnitude-based deconvolution.

Example 27. The computer program product of example 25 or example 26, wherein the instruction set is to further cause the at least one processing device to register the plurality of sets of OCT image data relative to the target object volume or volumes prior to the reconstructing of the space-domain OCT images for each of the plurality of sets of OCT image data and to then coherently average the reconstructed registered OCT image data to suppress noise or to enhance a signal-to-noise ratio.

Example 28. The computer program product of example 25 or example 26, wherein the instruction set is to further cause the at least one processing device to phase-register the plurality of sets of OCT image data relative to the target object volume or volumes prior to the reconstructing of the space-domain OCT images for each of the plurality of sets of OCT image data and to then coherently average the reconstructed phase-registered OCT image data to suppress noise or to enhance a signal-to-noise ratio.

Example 29. The computer program product of any of examples 25-28, wherein the instruction set is to further cause the at least one processing device to reconstruct the space-domain OCT images for each of the plurality of sets of OCT image data via background subtraction, spectrum resampling, dispersion correction, and/or inverse Fourier transformation.

Example 30. The computer program product of any of examples 25-29, wherein the instruction set is to further cause the at least one processing device to implement image processing and/or image registration following the reconstructing of the space-domain OCT images for each of the plurality of sets of OCT image data.

Example 31. The computer program product of example 30, wherein the instruction set is to further cause the at least one processing device to perform image processing via acts including coherence-gate curvature correction, coherence-gate curvature removal, defocus correction, and/or computational adaptive optics.

Example 32. The computer program product of example 30 or example 31, wherein the instruction set is to further cause the at least one processing device to perform the image registration via acts including correction for movement of the target volume as between the plurality of sets of OCT image data.

Example 33. The computer program product of example 30 or example 31, wherein the instruction set is to further cause the at least one processing device to perform the image registration via acts including bulk phase drift correction, elastic image registration, and/or bulk phase drift correction.

Example 34. The computer program product of any of examples 25-31, wherein the instruction set is to further cause the at least one processing device to computationally expand the spatial bandwidth of the coherent-averaged OCT image data by acts including computing a 2D Fourier transform of a coherent-averaged volume of the coherent-averaged reconstructed space-domain OCT images along a transverse dimension.

Example 35. The computer program product of example 34, wherein the instruction set is to further cause the at least one processing device to obtain a magnitude spectrum of an image by averaging the magnitude of the 2D Fourier transform across between about 10-30 depths about the focal plane.

Example 36. The computer program product of example 35, wherein the instruction set is to further cause the at least one processing device to curve fit the magnitude spectrum of the image a predetermined curve.

Example 37. The computer program product of example 35, wherein the instruction set is to further cause the at least one processing device to curve fit the magnitude spectrum of the image to a Gaussian curve.

Example 38. The computer program product of example 35, wherein the instruction set is to further cause the at least one processing device to identify systematic noise patterns in the magnitude spectrum of the image.

Example 39. The computer program product of any of examples 35-38, wherein the instruction set is to further cause the at least one processing device to compute a target spectrum shape with expanded bandwidth.

Example 40. The computer program product of example 39, wherein the instruction set is to further cause the at least one processing device to compute a target spectrum shape with an expanded bandwidth.

Example 41. The computer program product of example 40, wherein the target spectrum shape is a Gaussian spectrum.

Example 42. The computer program product of example 40, wherein the target spectrum shape is a flattop spectrum.

Example 43. The computer program product of any of examples 39-42, wherein the instruction set is to further cause the at least one processing device to compute a bandwidth expansion mask as the target spectrum shape divided by the original magnitude spectrum.

Example 44. The computer program product of any of examples 39-43, wherein the instruction set is to further cause the at least one processing device to edit spatial frequencies in the bandwidth expansion mask responsive to systematic noise patterns in the magnitude spectrum of the image.

Example 45. The computer program product of any of examples 43-44, wherein the instruction set is to further cause the at least one processing device to generate a product by multiplying the 2D Fourier transform and the bandwidth expansion mask.

Example 46. The computer program product of example 45, wherein the instruction set is to further cause the at least one processing device to compute the 2D inverse Fourier transform of the product to generate a final resolution-enhanced space-domain image.

Example 47. The computer program product of any of examples 25-46, wherein the instruction set is to further cause the at least one processing device to acquire a first image data set comprising resolution enhanced (RE-OCT) image data and to acquire a second image data set comprising aberration-diverse (AD-OCT) image data.

Example 48. The computer program product of any of examples 25-47, wherein the instruction set is to further cause the at least one processing device to acquire multiple repeated OCT volumes of the target object volume successively.

Example 49. A method for measuring a target sample based on optical coherent tomography (OCT) imaging, comprising: operating an OCT device to successively acquire multiple volumes of OCT images from the target sample; performing a reconstruction operation on each volume of the acquired OCT images in a space domain to generate reconstructed volumes of the acquired OCT images; performing an image registration operation to generate phase-registered volumes of the acquired OCT images by registering the reconstructed volumes of the acquired OCT images; coherently averaging the phase-registered volumes of the acquired OCT images to generate coherent-averaged volumes of the acquired OCT images; and generating a resolution-enhanced space-domain image by performing a computational operation to expand a spatial bandwidth of the coherent-averaged OCT volumes using a magnitude-based deconvolution procedure.

Example 50. The method as in example 49, wherein the reconstruction operation includes at least one of background subtraction, spectrum resampling, dispersion correction, or inverse Fourier Transform.

Example 51. The method as in example 49, wherein the reconstruction operation includes at least one of coherence-gate curvature correction operation, computational defocus correction operation, or computational adaptive optics operation.

Example 52. The method as in example 49, wherein the reconstructed volumes of the OCT images are registered such that structures of interest in the target sample are phase-registered Example 53. The method as in example 49, further comprising correcting phase shifts of individual volumes to register all volumes.

Example 54. The method as in example 49, wherein the coherent-averaged volumes of the OCT images are generated to suppress noise in the OCT images by enhancing a signal to noise ratio (SNR).

Example 55. The method as in example 54, wherein the magnitude-based deconvolution procedure is performed after suppressing noise in the OCT images.

Example 56. The method as in example 49, wherein the computational operation includes computing a two-dimensional Fourier transform of the coherent-averaged volume along a transverse dimension.

Example 57. The method as in example 56, wherein the computational operation includes obtaining a magnitude spectrum of the OCT images by averaging the magnitude of the two-dimensional Fourier transform.

Example 58. The method as in example 57, wherein the computational operation includes fitting the magnitude spectrum to a Gaussian curve.

Example 59. The method as in example 58, wherein the computational operation includes computing a target spectrum shape with an expanded bandwidth.

Example 60. The method as in example 59, wherein the computational operation includes computing a bandwidth expansion mask as the target spectrum shape divided by the magnitude spectrum.

Example 61. The method as in example 60, wherein the computational operation includes multiplying the two-dimensional Fourier transform by the bandwidth expansion mask.

Example 62. The method as in example 61, wherein the computational operation includes computing the two-dimensional Fourier transform of the product of the two-dimensional Fourier transform and the bandwidth expansion mask to generate the resolution-enhanced space-domain image.

Example 63. An optical coherent tomography (OCT) imaging method, comprising: operating an OCT device to successively acquire multiple volumes of OCT images from a target sample; performing a noise suppression operation by using a coherent averaging process on the multiple volumes of OCT images to generate multiple coherent-averaged OCT volumes; and generating resolution-enhanced OCT volumes by performing a computational bandwidth expansion operation to expand a spatial bandwidth of the multiple coherent-averaged OCT volumes.

Example 64. The method as in example 63, further comprising, before performing the noise suppression operation, performing an OCT reconstruction operation including at least one of background subtraction, spectrum resampling, dispersion correction, or inverse Fourier Transform.

Example 65. The method as in example 64, further comprising, before performing the noise suppression operation, performing at least one of image processing, coherence-gate curvature removal, defocus correction, or computational adaptive optics.

Example 66. The method as in example 63, wherein the coherent-average noise suppression operation includes at least one of image registration, bulk shift correction or elastic image registration, or bulk phase drift correction.

Example 67. The method as in example 66, wherein the computational bandwidth expansion operation includes two-dimensional Fourier Transform, depth averaging operation to generate an original magnitude spectrum, spectrum curve-fitting to generate a target spectrum shape, mathematical operations on the original magnitude spectrum and the target spectrum shape to generate a bandwidth expansion mask, mathematical operations on the original magnitude spectrum and the bandwidth expansion mask to generate an expanded magnitude spectrum, and 2D inverse Fourier Transform to generate a resolution-enhanced OCT volumes.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a," "an" and "the" are intended to include the plural forms as well, unless the context clearly indicates otherwise. Additionally, the use of "or" is intended to include "and/or," unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A system comprising:
    a processing platform comprising one or more processing devices operatively coupled to one or more memory devices;
    the processing platform being configured to:
        acquire a plurality of sets of optical coherence tomography (OCT) image data for a target object volume;
        reconstruct space-domain OCT images for each of the plurality of sets of OCT image data;
        generate coherent-averaged OCT image data having at least two dimensions by coherently averaging the space-domain OCT images to suppress noise or enhance a signal-to-noise ratio; and
        computationally expand a spatial-frequency bandwidth of the coherent-averaged OCT image data, at higher frequencies, via a magnitude-based deconvolution using a multi-dimensional bandwidth expansion mask.

2. The system of claim 1, wherein the processing platform is further configured to register the plurality of sets of OCT image data relative to the target object volume or volumes prior to the reconstructing of the space-domain OCT images for each of the plurality of sets of OCT image data and to then coherently average the reconstructed registered OCT image data to suppress noise or to enhance a signal-to-noise ratio.

3. The system of claim 1, wherein the processing platform is further configured to phase-register the plurality of sets of OCT image data relative to the target object volume or volumes prior to the reconstructing of the space-domain OCT images for each of the plurality of sets of OCT image data and to then coherently average the reconstructed phase-registered OCT image data to suppress noise or to enhance a signal-to-noise ratio.

4. The system of claim 1, wherein the reconstructing of the space-domain OCT images for each of the plurality of sets of OCT image data comprises background subtraction, spectrum resampling, dispersion correction, and/or inverse Fourier transformation.

5. The system of claim 1, wherein the processing platform is further configured to implement image processing and/or image registration following the reconstructing of the space-domain OCT images for each of the plurality of sets of OCT image data.

6. The system of claim 5, wherein the image processing comprises coherence-gate curvature correction, coherence-gate curvature removal, defocus correction, and/or computational adaptive optics.

7. The system of claim 5, wherein the image registration comprises correction for movement of the target volume as between the plurality of sets of OCT image data.

8. The system of claim 5, wherein the image registration comprises bulk phase drift correction, elastic image registration, and/or bulk phase drift correction.

9. The system of claim 1, wherein the processing platform is further configured, in computationally expanding the spatial bandwidth of the coherent-averaged OCT image data via magnitude-based deconvolution, to compute a 2D Fourier transform of a coherent-averaged volume of the coherent-averaged OCT image data along a transverse dimension.

10. The system of claim 9, wherein the processing platform is further configured to average the magnitude of the 2D Fourier transform across between about 10-30 depths about a focal plane to obtain a magnitude spectrum of an image.

11. The system of claim 10, wherein the magnitude spectrum of the image is curve fit to a predetermined curve.

12. The system of claim 11, wherein the processing platform is further configured to compute a target spectrum shape with expanded bandwidth.

13. The system of claim 12, wherein the processing platform is further configured to compute the multi-dimensional bandwidth expansion mask as the target spectrum shape divided by the magnitude spectrum.

14. The system of claim 13, wherein the processing platform is further configured to edit spatial frequencies in the multi-dimensional bandwidth expansion mask responsive to systematic noise patterns in the magnitude spectrum of the image.

15. The system of claim 13, wherein the processing platform is further configured to generate a product by multiplying the 2D Fourier transform and the multi-dimensional bandwidth expansion mask.

16. The system of claim 15, wherein the processing platform is further configured to compute a 2D inverse Fourier transform of the product to generate a final resolution-enhanced space-domain image.

17. The system of claim 10, wherein the processing platform is further configured to identify systematic noise patterns in the magnitude spectrum of the image.

18. The system of claim 1, wherein the plurality of related sets of optical coherence tomography (OCT) image data for a target object volume comprises at least one set of resolution enhanced (RE-OCT) image data and at least one set of aberration-diverse (AD-OCT) image data.

19. The system of claim 1, wherein the plurality of sets of OCT image data for a target object volume comprises acquire multiple repeated OCT volumes of the target object volume successively.

20. The system of claim 1, further comprising:
an optical coherence tomography (OCT) imaging system that includes a light source to produce light, a reference arm that receives a portion of the light as an optical reference beam and a sample arm that receives another portion of the light as an optical sample beam to illuminate a sample to be measured, wherein the optical sample arm includes an objective lens for directing the optical sample beam to the sample and for collecting returned light from the sample, wherein the optical sample arm is structured to underfill the objective lens when directing the optical sample beam to the objective lens to illuminate the sample,
wherein the processing platform receives the plurality of sets of optical coherence tomography (OCT) image data for a target object volume of the sample illuminated by the OCT imaging system.

21. The system of claim 1, wherein the expanded spatial-frequency bandwidth and the multi-dimensional bandwidth expansion mask are associated with two spatial dimensions or three spatial dimensions.

22. The system of claim 1, wherein processing platform is configured to generate coherent-averaged OCT image data having two dimensions or three dimensions.

* * * * *